United States Patent [19]

Lecka-Czernik

[11] Patent Number: 5,905,146
[45] Date of Patent: May 18, 1999

[54] DNA BINDING PROTEIN S1-3

[75] Inventor: Beata Lecka-Czernik, Little Rock, Ark.

[73] Assignee: University of Arkansas, Little Rock, Ark.

[21] Appl. No.: 08/616,857

[22] Filed: Mar. 15, 1996

[51] Int. Cl.$^6$ .............................. C07H 21/04; C12N 1/21; C12N 15/12; C12N 15/85
[52] U.S. Cl. .................. 536/23.5; 435/252.3; 435/320.1; 435/325; 536/24.31
[58] Field of Search ............................... 536/24.31, 23.1, 536/23.5; 435/320.1, 240.1, 6, 325, 252.3

[56] References Cited

PUBLICATIONS

Hillier L, et al. EST Database Accession No. T89209, Mar. 20, 1995.

Kaziro, Y.; The role of Guanosine 5'–Triphosphate in Polypeptide Chain Elongation; *Biochimica et Biophysica Acta,* 505:95–127 (1978).

Arber, S., Halder, et al.; Muscle LIM protein, a novel essential regulator of myogenesis, promotes myogenic differentiation. *Cell,* 79:221–231 (1994).

Argaves, W. S., Tran, et al.; Fibulin is an extracellular matrix and plasma glycoprotein with repeated domain structure *J. Cell Biol.,* 111:3155–3164 (1990).

Ausubel, F.M., et al.; DNA protein interactions. In: *Current Protocols in Molecular Biology,* vol. II, Greene Publishing Associates and John Wiley and Sons (1991).

Chalfie, M., Tu, Y., Euskirchen, G., Ward, W.W., and Prasher, D.C.; Green fluorescent protein as a marker for gene expression. *Science,* 263:802–805 (1994).

Call, K.M., Glaser, T., Ito, C.Y., Buckler, A.J., Pelletier, J., Haber, D.A., Rose, E.A., Kral, A., Yeger, H., Lewis, W.H., Jones, C., and Housman, D.E.; Isolation and characterization of a zinc finger polypeptide gene at the human chromosome 11 Wilms' tumor locus. *Cell,* 60:509–520 (1990).

Cristofalo, V.J. and Pignolo, R.J.; Replicative senescence of human fibroblast–like cells in culture. *Physiol. Rev.,* 73:617–638 (1993).

Dice, F.J.; Cellular and molecular mechanisms of aging. *Physiol. Rev.,* 73:149–159 (1993).

Dje, K.J., Mazabraud, A., Viel, A.L., le Maire, M., Denis, H.I., Crawford, E., and Brown, D.D.; Three genes under different developmental control encode elongation factor 1–α in *Xenopus laevis. Nucleic Acids Res.,* 18:3489–3493 (1990).

Duguid, J.R., Rohwer, R.G., and Seed, B.; Isolation of cDNAs of scrapie–modulated RNAs by subtractive hybridization of a cDNA library. *Proc. Natl. Acad. Sci. USA,* 85:5738–5742 (1988).

Dulic, V., Drullinger, L.F., Lees, E., Reed, S.I., and Stein, G.H.; Altered regulation of $G_1$ cyclins in senescent human diploid fibroblasts: accumulation of inactive cyclin E–Cdk2 and cyclin D1–Cdk2 complexes. *Proc. Natl. Acad. Sci. USA* 90:11034–11038 (1993).

Dulic, V., Kaufmann, W.K., Wilson, S.J., Tisty, T.D., Lees, E., Harper, J.W., Elledge, S.J., and Reed, S.I.; p53–dependent inhibition of cyclin–dependent kinase activities in human fibroblasts during radiation–induced G1 arrest. *Cell,* 76:1013–1023 (1994).

El–Deiry, W.S., Tokino, T., Velculescu, V.E., Levy, D.B., Parson, R., Trent, J.M., Lin, D., Mercer, W.E., Kinzler, K.W., and Vogelstein, B.; WAF1, a potential mediator of p53 tumor suppression. *Cell,* 75:817–825 (1993).

Epstein, C.J., Martin, G.M., Schultz, A.L., and Motulski, A.G.; Werner syndrome: A review of its symptomatology, natural history, pathologic features, genetics and relationship to the natural aging process. *Medicine,* 45:177–221 (1966).

Gilles, A.M., Presecan, E., Vonica, A., and Lascu, I.; Nucleoside diphosphate kinase from human erythrocytes. *J. Biol. Chem.,* 266:8784–8789 (1991).

Goldstein S.; The Biology of Aging, in *Textbook of Internal Medicine,* Section Editor, W.R. Hazzard. Editor–in–Chief, W.N. Kelly, J.B. Lippincott, Philadelphia, 2nd edition, pp. 2336–2342 (1992).

Goldstein S.; Replicative senescence: The human fibroblast comes of age. *Science,* 249:1129–1133 (1990).

Goldstein S. and Lin C.C.; Rescue of senescent human fibroblasts by hybridization with hamster cells in vitro. *Exp. Cell Res.* 70:436–439 (1971).

Goldstein, S., Murano, S., Benes, H., Moerman, E.J., Jones, R.A., Thweatt, R., Shmookler Reis, R.J., and Howard, B.H.; Studies on the molecular genetic basis of replicative senescence in Werner syndrome and normal fibroblasts. *Exp. Gerontol,* 24:461–468 (1989).

Goldstein, S., Moerman, E.J., Fujii, S., and Sobel, B.E.; Overexpression of plasminogen activator inhibitor type–1 in senescent fibroblasts from normal subjects and those with Werner syndrome. *J. Cell Physiol.,* 161:571–579 (1994).

Goldstein, S., Moerman, E.J., and Baxter, R.C.; Accumulation of insulin–like growth factor binding protein–3 in conditioned medium of human fibroblasts increases with chronological age of donor and senescence in vitro. *J. Cell Physiol.,* 156:294–302 (1993).

Goto, J., Rubenstein, J., Weber, J., Woods, K., and Drayna, D.; Genetic linkage of Werner's syndrome to file markers on chromosome. 8. *Nature,* 355:735–738 (1992).

Grigoriev, V.G., Moerman, E.J., and Goldstein, S.; Overexpression of insulin–like growth factor binding protein–3 by senescent human fibroblasts: Attenuation of the mitogenic response to IGF–1. *Exp. Cell Biol.,* 219:315–321 (1995).

(List continued on next page.)

*Primary Examiner*—Douglas W. Robinson
*Assistant Examiner*—Amy J. Nelson
*Attorney, Agent, or Firm*—Benjamin Aaron Adler

[57] ABSTRACT

A substantially pure S1-3 protein (a) being a DNA binding protein containing three zinc finger domains, (b) whose mRNA is overexpressed in senescent human diploid fibroblasts or human diploid fibroblasts derived from a patient with Werner Syndrome, and (c) whose mRNA is not expressed in fetal human diploid fibroblasts.

10 Claims, 19 Drawing Sheets

OTHER PUBLICATIONS

Grigoriev, V.G., Moerman, E.J., and Goldstein, S., Senescence and cell density of human diploid fibroblasts influence metabolism of insulin–like growth factor binding proteins. *J. Cell Physiol.* 160:203–211 (1994).

Grigoriev, V.G., Tweatt, R., Moerman, E.J., and Goldstein, S.; Expression of senescence–induced protein WS3–10 in vivo and in vitro. *Exp. Gerontol,* 31:145–157 (1996).

Gyuris, J., Golemis, E., Chertkov, H., and Brent, R.; Cdil, a human G1 and S phase protein phosphatase that associates with Cdk2. *Cell,* 75:791–803 (1993).

Hara, E., Yamaguchi, T., Nojima, H., Ide, T., Campisi, J., Okayama, H., and Oda, K.; Id–related genes encoding helix–loop–helix proteins are required for $G_1$ progression and are repressed in senescent human fibroblasts. *J. Biol. Chem.* 269:2139–2145 (1994).

Hall, C., Sin, W.C., Teo, M., Michael, P., Smith, P., Dong, J.M., Lim, H.H., Manser, E., Spurr, N.K., Jones, T.A., and Lim, L.; α2–chimerin, an SH2–containing GTYPase–activating protein for the ras–related protein $p21^{rac}$ derived by alternative splicing of the human n–chimerin gene, is selectively expressed in brain regions and testes. *Mol. Cell Biol.,* 13:4986–4998 (1993).

Harley, C.V., and Goldstein, S.; Cultured human fibroblasts: Distribution of cell generations and a critical limit. *J. Cell. Physiol.,* 97:509–516 (1978).

Harper, J.W., Adami, G.R., Wei, N., Keyomarsi, K., and Elledge, S.J.; The p21 Cdk–interacting protein Cip1 is a potent inhibitor of G1 cyclin–dependent kinases. *Cell,* 75:805–816 (1993).

Iwahana H.; A Rapid and Efficient Nonradioactive Method for Screening Recombinant DNA Libraries. *Biotechniques,* 16:98–102 (1994).

Jarvis, W.D., Kolesnick, R.N., Fornari, F.A., Traylor, R.S., Gerwirtz, D.A., and Grant, S.; Induction of apoptotic DNA damage and cell death by activation of the sphingomyelin pathway. *Proc. Natl. Acad. Sci. USA,* 91:73–77 (1994).

Joseph, L.J., Le Beau, M.M., Jamieson, Jr., G.A., Acharya, S., Shows, T.B., Rowley, J.D., and Sukhatme, V.P.; Molecular cloning, sequencing, and mapping of EGR2, a human early growth response gene encoding a protein with "zinc–binding finger" structure. *Proc. Nat'l. Acad. Sci., U.S.A.,* 85:7164–7168 (1988).

Kadonaga, J.T., Carner, K.R., Masiarz, F.R., and Tijan, R.; Isolation of cDNA encoding transcription factor Sp1 and functional analysis of the DNA binding domain. *Cell,* 51:1079–1090 (1987).

Kanzaki, T., Olofsson, A., Moren, A., Wernstedt, C., Hellman, U., Miyazono, K., Claesson–Welsh, L., and Heldin, C.; TGF–β1 binding protein: a component of the large latent complex of TGF–β1 with multiple repeat sequences. *Cell,* 61:1051–1061 (1990).

Kiess, M., Scharm, B., Aguzzi, A., Hajnal, A., Klemenz, R., Schwarte–Waldhoff, I., and Schafer, R.; Expression of ril, a novel LIM domain gene, is down–regulated in HRAS–transformed cells and restored in phenotypic revertants. *Oncogene,* 10:61–68 (1995).

Koff, A., Ohtsuki, M., Polyak, K., Roberts, J.M., and Massague, J.; Negative regulation of G1 in mammalian cells: inhibition of cyclin E–dependent kinase by TGF–beta. *Science,* 260:536–539 (1993).

Kolesnick, R. and Golde, D.W.; The sphingomyelin pathway in tumor necrosis factor and interleukin–1 signaling. *Cell,* 77:325–328 (1994).

Lecka–Czernik, B., Lumpkin, C.K., and Goldstein, S.; An overexpressed gene transcript in senescent and quiescent human fibroblasts encoding a novel protein in the EGF–like repeat family stimulates DNA synthesis. *Mol. Cell Biol.,* 15:120–128 (1995).

Lecka–Czernik, B., Moerman, E.J., Jones, R.A., and Goldstein, S.; Identification of gene sequences overexpressed in senescent and Werner syndrome fibroblasts. *Exp. Gerontology,* 31:159–174 (1996).

Lew, D.J., Dulic, V., and Reed, S.I.; Isolation of three novel human cyclins by rescue of G1 cyclin (Cln) function in yeast. *Cell,* 66:1197–1206 (1991).

Liu, S., Thweatt, R., Lumpkin, C.K., and Goldstein, S.; Suppression of calcium–dependent membrane currents in human fibroblasts by replicative senescence and forced expression of a gene sequence encoding a putative calcium–binding protein. *Proc. Natl. Acad. Sci. USA,* 91:2186–2190 (1994).

Maslen, C.L., Corson, G.M., Maddox, B.K., Glanville, R.W., and Sakai, L.Y.; Partial sequence of a candidate gene for the Marfan syndrome. *Nature,* 352:334–337 (1991).

Moerman, E.J., Thweatt, R., Moerman, A.M., Jones, R.A., and Goldstein, S.; Insulin–like growth factor binding protein–3 is overexpressed in senescent and quiescent human fibroblasts. *Exp. Gerontology,* 28:361–370 (1993).

Morris, J.F., Hromas, R., and Rauscher, F.J., III; Characterization of the DNA–binding properties of the myeloid zinc finger protein MZF1: Two independent DNA–binding domains recognize two DNA consensus sequences with a common G–rich core. *Mol. Cell. Biol.,* 14:1786–1795 (1994).

Murano, S., Thweatt, R., Shmookler Reis, R.J., Jones, R.A., Moerman, E.J., and Goldstein, S.; Diverse gene sequences are overexpressed in Werner syndrome fibroblasts undergoing premature replicative senescence. *Mol. Cell Biol.,* 11:3905–3914 (1991).

Nevins, J.R.; A closer look at E2F. *Nature,* 358:375–376 (1992).

Noda, A., Ning, Y., Venable, S.F., Pereira–Smith, O.M., and Smith, J.R.; Cloning of senescent cell–derived inhibitors of DNA synthesis using an expression screen. *Exp. Cell Res.,* 211:90–98 (1994).

Norwood, T.H., Pendergrass, W.R., Sprague, C.A., and Martin, G.M.; Dominance of the senscent phenotype in heterokaryons between replicative and post–replicative human fibroblast–like cells. *Proc. Natl. Acad. Sci. USA,* 71:2231–2235 (1974).

Norwood, T.H., Smith, J.R., and Stein, G.H.; Aging at the cellular level: the human fibroblastlike cell model. In: *Handbook of Biology of Aging,* E.L. Schneider and J.W. Rowe, eds., 3rd ed., pp. 131–154, (1990).

Obeid, L.M.; Ceramide: an endogenous inducer of cellular senescence. *Clin. Res.,* 42:114A (1994).

Obeid, L.M., Linardic, C.M., Karolak, L.A., and Hannun, Y.A.; Programmed cell death induced by ceramide. *Science,* 259:1769–17771 (1993).

Panayotou, G., End, E., Aumailley, M., Timple, R., and Engel, J.; Domains of laminin with growth–factor activity. *Cell,* 56:93–101 (1989).

Pathak, V.K., Nielsen, P.J., Trachsel, H., and Hershey, J.W.; Strcuture of the β subunit of translation initiation factor eIF–2. *Cell,* 54:633–639 (1988).

Peter, M. and Herskowitz, I.; Joining the complex: cyclin–dependent kinase inhibitory proteins and the cell cycle. *Cell,* 79:181–184 (1994).

Ptashne, M.; How eukaryotic transcriptional activators work. *Nature,* 335:683–689 (1988).

Rasoamanantena, P., Thweatt, R., Labat–Robert, J., and Goldstein, S.; Altered Regulation of fibronectin gene expression in Werner syndrome fibroblasts. *Exp. Cell Res.* 213:121–127 (1994).

Sadler, I., Crawford, A.W., Michelsen, J.W., and Beckerle, M.C.; Zyxin and cCRP: Two interactive LIM domain proteins associated with the cytoskeleton. *J. Cell Biol.,* 119:1573–1587 (1992).

Sakamoto, K., Fordis, C.M., Corsico, C.D., Howard, T.H., and Howard, B.H.; Modulation of HeLa cell growth by transfected 7SL RNA and Alu gene sequences. *J. Biol. Chem.,* 266:3031–3038 (1991).

Salk, D.; Werner's syndrome: a review of recent research with an analysis of connective tissue metabolism, growth control of cultured cells and chromosomal aberrations. *Hum. Genet.,* 62:1–5 (1982).

Sanchez–Garcia, I. and Rabbits, T.H.; The LIM domain: a new structural motif found in zinc–finger–like proteins. *Trends Genet.,* 10:315–320 (1994).

Schmeichel, K.L. and Beckerle, M.C.; The LIM domain is a modular protein–binding interface. *Cell,* 79:211–219 (1994).

Schuchman, E.H., Suchi, M., Takahashi, T., Sandhoff, K., and Desnick, R.J.; Human acid sphingomyelinase. Isolation, nucleotide sequence and expression of the full–length and alternatively spliced cDNAs. *J. Biol. Chem.,* 266:8531–8539 (1991).

Schweinfest, C.W., Henderson, K.W., Gu, J., Kottardis, S.D., Besbeas, S., Panotopoulou, E., and Papas, T.S.; Subtraction hybridization cDNA libraries from colon carcinoma and hepatitic cancer. *Genet Annal. Techn. Appl.,* 7:64–70 (1990).

Serrano, M., Hannon, G.J., and Beach, D.; A new regulatory motif in cell–cycle control causing specific inhibition of cyclin D/CDK4. *Nature* 366:704–707 (1993).

Seshadri, T. and Campisi, J.; Repression of c–fos transcription and an altered genetic program in senescent human fibroblasts. *Science,* 247:205–209 (1990).

Shibanuma, M., Mashimo, J., Koroki, T., and Nose, K.; Characterization of the TGFβ1–inducible hic–5 gene that encodes a putative novel zinc finger protein and its possible involvement in cellular senescence. *J. Biol. Chem.,* 269:26767–26774 (1994).

Shiina, N., Gotoh, Y., Kubomura, N., Iwamatsu, A., and Nishida, B.; Microtubule severing by elongation factor 1α. *Science,* 266:282–285 (1994).

Sive, H.L. and St. John, T.; A simple subtractive hybridization technique employing photactivatable biotin and phenol extaction. *Nucleic Acid Res.,* 16:10937 (1988).

Stahl, J.A., Leone, A., Rosengard, A.M., Porter, L., King, C.R., and Steeg, P.S.; Identification of a second human nm23–H2, *Cancer Res.,* 52:445–449 (1991).

Steeg, P.S., Bevilacqua, G., Kopper, L., Thorgeirsson, U.P., Talmadge, J.E., Liotta, L.A., and Sobel, M.E.; Evidence for a novel gene associated with low tumor metastatic potential. *J. Natl. Cancer Inst.,* 80:200–204 (1988).

Tanaka, K., Nakazawa, T., Okada, Y., and Kumahara, Y.; Roles of nuclear and cytoplasmic environments in the retarded DNA synthesis of Werner syndrome cells. *Exp. Cell Res.,* 127:185–190 (1980).

Tatsuka, M., Mitsui, H., Wada, M., Nagata, A., Nojima, H., and Okayama, H.; Elongation factor–1α gene determines susceptibility to transformation. *Nature,* 359:333–336 (1992).

Tautz, D., Lehmann, R., Schnurch, H., Schuh, R., Seifert, E., Kienlin, A., Jones, K., and Jackle, H.; Finger protein of novel structure encoded by hunchback, a second member of the gap class of Drosophila segmentation genes. *Nature,* 327:383–389 (1987).

Termin, J.D.; Cellular activity, matrix proteins, and aging bone. *Exp. Gerontol,* 25:217–221 (1990).

Thweatt, R., Lumpkin, C.K., and Goldstein, S.; A novel gene encoding a smooth muscle protein is overexpressed in senescent human fibroblasts. *Biochem. Biophys. Res. Commun.,* 187:1–7 (1992).

Thweatt, R. and Goldstein S.; Werner syndrome and biological aging: a molecular genetic hypothesis. *BioEssays,* 15:421–426 (1993).

Uetsuki, T., Naito, A., Nagata, S., and Kaziro, Y.; Isolation and characterization of the human chromosomal gene for polypeptide chain elongation factor 1–α. *J. Biol. Chem.,* 264:5791–5798 (1989).

Wang, A.M., Doyle, M.V., and Mark, D.F.; Quantitation of mRNA by the polymerase chain reaction. *Proc. Nat'l. Acad. Sci., U.S.A.,* 86:9717–9721 (1989).

Wang, L., Patel, U., Ghosh., L., Chen, H.C., and Banerjee, S.; Mutation in the nm23 gene is associated with metastasis in colorectal cancer. *Cancer Res.,* 53:717–720 (1993).

Wharton, K.A., Johansen, K.M., Xu T., and Artavanis–Tsakonas, S.; Nucleotide sequence from the neurogenic locus Notch implies a gene product that shares homology with proteins containing EGF–like repeats. *Cell,* 43:567–581 (1985).

Xiong, Y., Hannon, G.J., Zhang, H., Casso, D., Kobayashi, R. and Beach, D.; p21 is a universal inhibitor of cyclin kinases. *Nature,* 366:701–704 (1993).

Benn, A., Antoine, M., Beug, H., and Niessing, J.; Primary structure and expression of a chicken cDNA encoding a protein with zinc–finger motifs. *Gene,* 106:207–212 (1991).

Bernard, O., Ganiatsas, S., Kannourakis, G., and Dringen, R.; Kiz–1, a protein with LIM zinc finger and kinase domains, is expressed mainly in neurons. *Cell Growth Differ.,* 5:1159–1171 (1994).

Bevilacqua, G., Sobel, M.E., Liotta, L.A., and Steeg, P.S.; Association of low nm23 RNA levels in human primary inflitrating ductal breast carcinomas with lymph node involvement and other histopathological indicators of high mestatic potential. *Cancer Res.,* 49:5185–5190 (1989).

Chomczynski, P. and Sacchi, N.; Single–step method of RNA isolation by acid guanidinium thiocyanate–phenol–chloroform extraction. *Anal. Biochem.,* 162:156–159 (1987).

Chowdhury, K., Rohdewohld, H., and Gruss P.; Specific and ubiquitous expression of different Zn finger protein genes in the mouse. *Nucleic Acids Res.,* 16:9995–10011 (1988).

Christy, B. and Nathans, D.; DNA binding site of the growth factor–inducible protein Zif268. *Proc. Nat'l. Acad. Sci, U.S.A.,* 86:8737–8741 (1989).

Church, G.M. and Gilbert, W.; Genomic sequencing. *Proc. Natl. Acad. Sci. USA,* 81:1991–1995 (1984).

Czernik P.J., Shin D.S. and Hurlburt B.K. Functional selection and characterization of DNA–binding sites for trp repressor of *E.coli. J. Biol. Chem.* 269:27869–27875 (1994).

DeTata, V., Ptasznik, A., and Cristofalo, V.J.; Effect of the tumor promoter phorbol 12–myristate 13–acetate (PMA) on proliferation of young and senescent W1–38 human diploid fibroblasts. *Exp. Cell Res.*, 205:261–269 (1993).

Dimri, G.P. and Campisi, J.; Altered profile of transcription factor–binding activities in senescent human fibroblasts. *Exp. Cell Res.*, 212:132–140 (1994).

Dimri, G.P., Hara, E., and Campisi, J.; Regulation of two E2F–related genes in presenescent and senescent human fibroblasts. *J. Biol. Chem.*, 269:16180–16186 (1994).

Doolittle, R.F., Feng, D.F., and Johnson, M.S.; Computer based characterization of epidermal growth factor precursor. *Nature*, 307:558–560 (1984).

Fett, R. and Knippers, R.; The primary structure of human glutaminyl–tRNA synthetase: A highly conserved core, amino acid repeat regions, and homologies with translation elongation factors. *J. Biol. Chem.*, 266:1448–1455 (1991).

Flemington, E.K., Speck, S.H., and Kaelin, W.G., Jr.; E2F–1–mediated transactivation is inhibited by complex formation with the retinoblastoma susceptibility gene product. *Proc. Natl. Acad. Sci. USA*, 90:6914–6918 (1993).

Freyd, G., Kim, S.K., and Horvitz, H.R.; Novel cysteine–rich motif and homeodomain in the product of the Caenorhabditis elegans cell linage gene lin–11. *Nature*, 344:876–879 (1990).

Funk, S.E. and Sage, H.E.; The $Ca^{2+}$–binding glycoprotein SPARC modulates cell cycle progression in aortic endothelial cells. *Pro. Natl. Acad. Sci. USA*, 88:2648–2652 (1991).

Goldstein S.; Cellular senescence. In: Endocrinology, 2nd Ed., L.J. DeGroot, F.G. Cahill, Jr., W.D. Odell, L. Martini, J.T. Potts Jr., D.H. Nelson, E. Steinberger and A.I. Winegrad, eds. Grune and Stratton, New York, pp. 2525–2549 (1989).

Hayflick L.; The limited in vitro lifetime of human diploid cell strains. *Exp. Cell Res.*, 37:614–636 (1965).

Hunter T.; Braking the cycle. *Cell*, 75:839–841 (1993).

Hurlburt, B.K. and Yanofsky, C.; trp repressor/trp operator interaction. Equilibrium and kinetic analysis of complex formation and stability. *J. Biol. Chem.*, 267:16783–16789 (1992).

Inoue, S., Orimo, A., Hosoi, T., Kondo, S., Toyoshima, H., Kondo, T., Ikegami, A., Ouchi, Y, Orimo, H., and Maramatsu, M.; Genomic binding–site cloning reveals an estrogen–responsive gene that encodes a Ring finger protein. *Proc. Natl. Acad. Sci.*, 90:11117–11121 (1993).

Jelinek, W.R. and Schmid, C.W.; Repetitive sequences in eukaryotic DNA and their expression. *Annu. Rev. Biochem.*, 51:813–844 (1982).

Karlsson, O., Thor, S., Norberg, T., Ohlsson, H., and Edlund, T.; Insulin gene enhancer binding protein Isl–1 is a member of a novel class of proteins containing both homeo– and Cys–His domain. *Nature*, 344:879–882 (1990).

Kenyon, K., Contente, S., Trackman, P.C., Tang, J., Kagan, H.M., and Friedman, R.M.; Lysyl oxidase and rrg messenger RNA. *Science*, 253:802 (1991).

Kenyon, K., Modi, W.S., Contente, S., and Friedman, R.M.; A novel human cDNA with a predicted protein similar to lysyl oxidase maps to chromosome 15q24–q25. *J. Biol. Chem.*, 268:18435–18437 (1993).

Kinzler, K.W. and Vogelstein, B. The GLI gene encodes a nuclear protein which binds specific sequences in the human genome. *Mol. Cell Biol.* 10:634–642 (1990).

Klug, A. and Rhodes, D.; Zinc fingers: a novel protein fold for nucleic acid recognition. *Cold Spring Harbor Symposia on Quantitative Biology*, 52:473–482 (1987).

Kornblihtt, A.R., Vibe–Pedersen, K., and Baralle, F.E.; Isolation and characterization of cDNA clones for human and bovine fibronectins. *Proc. Natl. Acad. Sci. USA*, 80:3218–3222 (1983).

Koths, K., Taylor, E., Halenbeck, R., Casipit, C., and Wang, A.; Cloning and characterization of a human Mac–2–binding protein a new member of the superfamily defined by the macrophage scavenger receptor cysteine–rich domain. *J. Biol. Chem.*, 268:14245–14249 (1993).

Kozak, M.; An analysis of vertebrate mRNA sequences: Intimations of translational control. *J. Cell Biol.*, 115:887–903 (1991).

Krieg, P.A. and Melton, D.A.; Functional messenger RNAs are produced by SP6 in vitro transcription of cloned cDNAs. *Nucleic Acid Res.*, 12:7057–7070 (1984).

Lee, S., Wolfraim, L.A., and Wang, E.; Differential expression of S1 and elongation factor–1α during rat development. *J. Biol. Chem.*, 268:24453–24459 (1993).

Letovsky, J. and Dynan, W.; Measurement of the binding of transcription factor Sp1 to a single GC box recognition sequence. *Nucleic Acids Res.*, 17:2639–2653 (1989).

Liotta, L.A. and Steeg, P.S.; Clues to the function of Nm23 and Awd proteins in development, signal transduction, and tumor metastasis provided by studies of *Dictyostelium discoideum*. *J. Natl. Cancer Instit.*, 82:1170–1173 (1990).

Lumpkin, C.K., Jr., McClung, J.K., Pereira–Smith, O.M., and Smith, J.R.; Existence of high abundance antiproliferative mRNAs in senescent human diploid fibroblasts. *Science*, 232:393–395 (1986).

Mann, K., Deutzman, R., Aumailley, M., Timpl, R., Raimondi, L., Yamada, Y., Pan, T., Conway, D., and Chu, M.; Amino acid sequence of mouse nidogen, a multidomain basement membrane protein with binding activity for laminin, collagen IV and cells. *EMBO J*, 8:65–72 (1989).

Moldave, K.; Eukaryotic protein synthesis. *Annu. Rev. Biochem.*, 54:1109–1149 (1985).

Moses, H.L., Yang, E.Y., and Pietenpol, J.A.; TGFβ stimulation and inhibition in cell proliferation: new mechanistic insights. *Cell*, 63:245–247 (1990).

Nada, S., Chang, P.K.K., and Digman, J.D.; Primary structure of the gene for glycyl–tRNA synthetase from Bombyx mori. *J. Biol. Chem.*, 268:7660–7667 (1993).

Ohashi, K., Toshima, J., Tajinda, K., Nakamura, T., and Mizuno, K.; Molecular cloning of a chicken lung cDNA encoding a novel protein kinase with N–terminal two LIM/double zinc finger motifs. *J. Biochem.*, 116:636–642 (1994).

Okayama, H., Kawaichi, M., Brownstein, J., Lee, F., Yokota, T., and Arai, K.; High–efficiency cloning of full–length cDNA: Construction and screening of cDNA expression libraries for mammalian cells. *Methods Enzymology*, 154:3–29 (1987).

Penttinen, R.P., Kobayashi, S., and Bornstein, P.; Transforming growth factor β increases mRNA for matrix proteins both in the presence and in the absence of changes in mRNA stability. *Proc. Natl. Acad. Sci. USA*, 85:1105–1108 (1988).

Pines, J. and Hunter, T.; Isolation of human cyclin cDNA: Evidence for cyclin mRNA and protein regulation in the cell cycle and for interaction with $p34^{cdc2}$. *Cell*, 58:833–846 (1989).

Polyak, K., Kato, J.Y., Solomon, M.J., Sherr, C.J., Messague, J., Roberts, J.M., and Koff A.; $p27^{Kip1}$, a cyclin–Cdk inhibitor, links transforming growth factor–β and contact inhibition to cell cycle arrest. *Genes & Development*, 8:9–22 (1994).

Polyak, K., Lee, M.H., Erdjument–Bromage, H., Koff, A., Roberts, J.M., Tempst, P. and Massague, J.; Cloning of p27$^{Kip1}$, a cyclin–dependent kinase inhibitor and a potential mediator of extracellular antimitogenic signals. *Cell*, 78:59–66 (1994).

Ponte, P., Ng, S.Y., Engel, J., Gunning, P., and Kedes, L.; Evolutionary conservation in the untranslated regions of actin mRNAs: DNA sequence of human beta–actin cDNA. *Nucleic Acids Res.*, 12:1687–1696 ((1984).

Quantitative RT–PCR. In: *Methods and Application,* Book 3, ed., Clontech Laboratories, Inc. (1993).

Rauscher, F.J., III, Morris, J.F., Tournay, O.E., Cook, D.M., and Curran, T.; Binding of the Wilms' tumor locus zinc finger protein to the EGR–1 consensus sequence. *Science*, 250:1259–1262 (1990).

Reed, M.J., Vernon, R.B., Abrass, I.B., and Sage, E.H.; TGF–β 1 induces the expression of type I collagen and SPARC, and enhances contraction of collagen gels, by fibroblasts from young and aged donors. *J. Cell Physiol.*, 158:169–179 (1994).

Riabowol, K., Schiff, J., and Gilman, M.Z.; Transcription factor AP–1 activity is required for inhibition of DNA synthesis and is lost during cellular aging. *Proc. Natl. Sci. Acad. USA*, 89:157–161 (1992).

Richter, K.H., Afshari, C.A., Annab, L.A., Burkhart, B.A., Owen, R.D., Boyd, J., and Barrett, J.C.; Down–regulation of cdc2 in senescent human and hamster cells. *Cancer Res.*, 51:6010–6013 (1991).

Ridley, A.J., Paterson, H.F., Johnston, C.L., Dickmann, D., and Hall, A.; The small GTP–binding protein rac regulates growth factor induced membrane ruffling. *Cell*, 70:401–410 (1992).

Riggs, A.D., Suzuki, H., and Bourgeois, S.; lac repressor–operator interaction I. Equilibrium studies. *J. Mol. Biol.*, 48:67–83 (1970).

Roberts, C.J., Birkenmeier, T.M., McQuillan, J.J., Akiyama, S.K., Yamada, S.S., Chen, W.T., Yamada, K.M., and McDonald, J.A.; Transforming growth factor δ stimulates the expression of fibronectin and of both subunits of the human fibronectin receptor by cultured human lung fibroblasts. *J. Biol. Chem.*, 263:4586–4592 (1988).

Rooney, B.C., Horne, C.H., and Hardman, N.; Molecular cloning of a cDNA for human pregnancy–specific β1–glycoprotein: homology with human carcinoembryonic antigen and related proteins. *Gene*, 71:439–449 (1988).

Ruoslahti, E. and Yamaguchi, Y.; Proteoglycans as modulators of growth factor activities. *Cell*, 64:867–869 (1991).

Sanger, F., Nicklen, S., and Coulson, A.R.; DNA sequencing with chain terminating inhibitors. *Proc. Natl. Acad. Sci, USA*, 74:5463–5467 (1977).

Schellenberg, G.D., MArtin, G.M., Wijsman, E.M., Nakura, J., Miki, T., and Ogihara, T.; Homozygosity mapping and Werner's syndrome. *Lancet*, 339:1002 (1992).

Shutze, S., Potthoff, K., Machleidt, T., Berkovic, D., Wiegmann, K., and Kronke, M.; TNF activates Nf–KB by phosphatidylcholine–specific phospholipase C–induced "Acidic" sphingomyelin breakdown. *Cell*, 71:765–776 (1992).

Shaw, G. and Kamen, R.; A conserved AU sequence from the 3' untranslated region of GM–CSF mRNA mediates selective mRNA degradation. *Cell*, 46:659–667 (1986).

Stein, G.H., Beeson, M., and Gordon, L.; Failure to phosphorylate the retinoblastoma gene product in senescent human fibroblasts. *Science*, 249:666–669 (1990).

Stein, G.H., Drullinger, L.F., Robetorye, R.S., Pereira–Smith, O.M., and Smith, J.; Senescent cells fail to express cdc2, cycA and cycB in response to mitogen stimulation. *Proc. Natl. Acad. Sci. USA* 88:11012–11016 (1991).

Stein, G.H. and Yanishevsky, R.M.; Quiescent human diploid cells can inhibit entry into S phase in replicative nuclei in heterodikaryons. *Proc. Natl. Acad. Sci. USA*, 78:3025–3029 (1981).

Sukhatme, V.P., Cao, X., Chang, L.C., Tsai–Morris, C., Stamenkovich, D., Ferreira, P.C.P., Cohen, D.R., Edwards, S.A., Shows, T.B., Curran, T., Le Bau, M.M., and Adamson, E.D.; A zinc finger–encoding gene coregulated with c–fos during growth and differentiation, and after cellular differentiation. *Cell*, 53:37–43 (1988).

Swaroop, A., Hogan, B.L.M., and Francke, U.; Molecular analysis of the cDNA for human SPARC/osteonectin/BM–40: sequence, expression, and localization of the gene to chromosome 5q31–q33. *Genomics*, 2:37–47 (1988).

Symington, B.E.; Fibronectin receptor modulates cyclin–dependent kinase activity. *J. Biol. Chem.*, 267:25744–25747 (1992).

Taylor, J.M., Davies, J.D., and Peterson, C.A.; Regulation of the myoblast–specific expression of the human δ–enolase gene. *J. Biol. Chem.*, 270:2535–2540 (1995).

Toyoshima, H. and Humter, T.; p27, a novel inhibitor of G1 cyclin–Cdk protein kinase activity, is related to p21. *Cell*, 78:67–74 (1994).

Venable, M.E., Lee, J.Y., Symth, M.J., Bielawska, A., and Obeid, L.M.; Role of ceramide in cellular senescence. *J. Biol. Chem.*, 270:30701–30708 (1995).

Walldorf, U., Fleig, R., and Gehring, W.J.; Comparision of homeobox–containing genes of the honeybee and Drosophila. *Proc. Nat'l. Acad. Sci., U.S.A.*, 86:9971–9975 (1989).

Wang, X., Lee., G., Liebhaber, S.A., and Cooke, N.E.; Human cysteine–rich protein: A member of the LIM/double–finger family displaying coordinate serum induction with c–myc. *J. Biol. Chem.*, 267:9176–9184 (1992).

Way, J.C. and Chalfie, M.; mec–3, a homeobox–containing gene that specifies differentiation of the touch receptor eurons in *C. elegans. Cell*, 54:5–16 (1988).

Witzgall, R., O'Leary, E., Gessner, R., Ouellette, A.J., and Bonventre, J.V.; Kid–1, a putative renal transcription factor. Regulation during ontogeny and in response to ischemia and toxic injury. *Mol. Cell. Biol.*, 13:1933–1942 (1993).

Yanishevsky, R.M. and Stein, G.H.; Ongoing DNA synthesis continues in young human diploid cells (HDC) fused to senescent HDC, but entry into S phase is inhibited. *Exp. Cell Res.*, 126:469–472 (1980).

Yu, C, Oshima, J., Fu, Y., Wijsman, E.M., Hisama, F., Alisch, R., Matthews, S., Nakura, J., Miki, T., Ouais, S., Martin, G.M., Mulligan, J., and Schellenberg, G.D.; Positional Cloning of the Werner's Syndrome Gene. *Science*, 272:258–262 (1996).

Hirsch–Behnam, A., Delius, H. and de Villiers, E.; A comparative sequence analysis of two human papillomavirus (HPV) tpes 2a and 57, *Virus Research*, 18:81–98 (1990).

FIGURE 2A

```
      cccattgaagtttgccggtccaaactgtccaaatacttgcagggagtagttttccgctg
  1   ---------+---------+---------+---------+---------+---------+  60
      ggggtaacttcaaacggccaggtttgacaggtttatgaacgtccctcatcaaaaggcgac

P  I  E  V  C  R  S  K  L  S  K  Y  L  Q  G  V  V  F  R  C tgataagtgtaccttcacctgctccagtgatgagagcctccagcaacatatagaaaagca
 61   ---------+---------+---------+---------+---------+---------+ 120
      actattcacatggaagtggacgaggtcactactctcggaggtcgttgtatatcttttcgt

D  K  C  T  F  T  C  S  S  D  E  S  L  Q  Q  H  I  E  K  H caatgaactgaaaccttacaaatgccagctctgctactatgagaccaagcacacggagga
121   ---------+---------+---------+---------+---------+---------+ 180
      gttacttgactttggaatgtttacggtcgagacgatgatactctggttcgtgtgcctcct

N  E  L  K  P  Y  K  C  Q  L  C  Y  Y  E  T  K  H  T  E  E actggacagccaccttcggaatgagcataaggtaagccgtaactttgagctggttggacg
181   ---------+---------+---------+---------+---------+---------+ 240
      tgacctgtcggtggaagccttactcgtattccattcggcattgaaactcgaccaacctgc

L  D  S  H  L  R  N  E  H  K  V  S  R  N  F  E  L  V  G  R agttaacttggatcagctggaacagatgaaggagaaaatggagagctccagcagcgatga
241   ---------+---------+---------+---------+---------+---------+ 300
      tcaattgaacctagtcgaccttgtctacttcctcttttacctctcgaggtcgtcgctact

V  N  L  D  Q  L  E  Q  M  K  E  K  M  E  S  S  S  S  D  D tgaggacaaggaagaagaaatgaacagcaaggctgaagacagagagctgatgagattttc
301   ---------+---------+---------+---------+---------+---------+ 360
      actcctgttccttcttctttacttgtcgttccgacttctgtctctcgactactctaaaag

E  D  K  E  E  E  M  N  S  K  A  E  D  R  E  L  M  R  F  S tgaccacggggctgctcttaacactgagaagcgttttccatgtgaattttgtggacgggc
361   ---------+---------+---------+---------+---------+---------+ 420
      actggtgccccgacgagaattgtgactcttcgcaaaaggtacacttaaaacacctgcccg

D  H  G  A  A  L  N  T  E  K  R  F  P  C  E  F  C  G  R  A gttttcacagggctctgagtgggaaagacatgtgctgagacacggcatggcattgaatga
421   ---------+---------+---------+---------+---------+---------+ 480
      caaaagtgtcccgagactcccctttctgtacacgactctgtgccgtaccgtaacttact

```
     caccaagcaggtgagcagagaagaaatccacccaaaagagatcatggagaacagtgttaa
481  ---------+---------+---------+---------+---------+---------+ 540
     gtggttcgtccactcgtctcttctttaggtgggttttctctagtacctcttgtcacaatt

T  K  Q  V  S  R  E  E  I  H  P  K  E  I  M  E  N  S  V  K aatgccctccatagaggaaaaggaagatgacgaggccattgggatagacttttccctaaa
541  ---------+---------+---------+---------+---------+---------+ 600
     ttacgggaggtatctccttttccttctactgctccggtaaccctatctgaaagggattt

M  P  S  I  E  E  K  E  D  D  E  A  I  G  I  D  F  S  L  K  - gaatgaaacagtagccatctgtgtagtaactgccgacaaatctctcctggagaatgcaga
601  ---------+---------+---------+---------+---------+---------+ 660
     cttactttgtcatcggtagacacatcattgacggctgtttagagaggacctcttacgtct

N  E  T  V  A  I  C  V  V  T  A  D  K  S  L  L  E  N  A  E  - ggccaaaaaagaatgagcgtttggtgaaattcttaatcaaaccttacttgaacagtgatg
661  ---------+---------+---------+---------+---------+---------+ 720
     ccggttttttcttactcgcaaaccactttaagaattagtttggaatgaacttgtcactac

A  K  K  E  * aaaaagtgggagggctggcttgggctgagaagggagggacagaaaagagaagacagaaca
721  ---------+---------+---------+---------+---------+---------+ 780
     ttttcaccctcccgaccgaacccgactcttccctccctgtcttttctcttctgtcttgt aagctgctttttaggactgaacaatctattttcaaagcactggtacctgtgtgagtgagt
781  ---------+---------+---------+---------+---------+---------+ 840
     ttcgacgaaaaatcctgacttgttagataaaagtttcgtgaccatggacacactcactca atgtaaattaaagttatttaaatggttggaatatgtggctccttttccatcactacatct
841  ---------+---------+---------+---------+---------+---------+ 900
     tacatttaatttcaataaatttaccaaccttatacaccgaggaaaaggtagtgatgtaga tttcttccggatcttcatcatggaagtttcatttgttgcggaatatggaagcacctccca
901  ---------+---------+---------+---------+---------+---------+ 960
     aaagaaggcctagaagtagtaccttcaaagtaaacaacgccttataccttcgtgagggt atggtacggtgcaccctgtggtggtcttggacagtatgtggaaacagaagctccatgacg
961  ---------+---------+---------+---------+---------+---------+ 1020
     taccatgccacgtgggacaccaccagaacctgtcatacacctttgtcttcgaggtactgc
```

FIGURE 2C

```
      gtagaagacttctcattgggggagcaacttttgacgcacaacttttggtgcgttttttc
1021  ---------+---------+---------+---------+---------+---------+ 1080
      catcttctgaagagtaaccccctcgttgaaaaactgcgtgttgaaaaccacgcaaaaaag tagttttaataccttaagcttttcaagacctaactgcagccgctttgggaaaaaaaaac
1081  ---------+---------+---------+---------+---------+---------+ 1140
      atcaaaattatggaattcgaaaaagttctggattgacgtcggcgaaaccctttttttttg aaaaaacaaaaaacagaaaac
1141  ---------+---------+- 1161
      ttttttgttttttgtcttttg
```

FIGURE 3B

|  |  |  |  |  |  |  |  |  |  |  |  |  |  |  |  |  |  |  |  |  |  |  |  |  |  |  |  | | |
|---|---|---|---|---|---|---|---|---|---|---|---|---|---|---|---|---|---|---|---|---|---|---|---|---|---|---|---|---|---|
| V | F | R | C | D | K | C | T | F | T | C | S | S | D | E | S | L | Q | Q | H | I | E | K | H | N | E | L | K | | (a) |
| P | Y | K | C | Q | L | C | E | Y | Y | E | T | K | H | T | Q | E | L | D | R | L | H | R | N | E | H | V | S | R | (b) |
| R | F | P | C | E | F | C | K | R | S | Y | T | H | Q | N | K | S | M | L | N | W | E | R | H | V | L | R | H | G | M | A | L | (c) |
| P | F | Q | C | R | V | C | H | I | C | G | S | A | G | R | S | L | W | S | Y | L | G | V | R | N | K | H | S | H | S | V | Y |
| P | Y | H | C | P | Y | C | D | Y | A | G | K | K | G | E | T | E | H | S | G | L | N | K | R | H | K | K | H | T | G | E | K |
| S | H | R | C | P | C | G | L | Q | G | F | A | W | K | A | S | H | A | Q | L | Q | R | H | Q | H | T | R | P | E | R |
| P | F | P | C | E | P | C | G | L | G | E | R | E | A | F | S | Q | G | K | A | H | L | T | K | H | R | R | S | H | G | P | K | A |
| P | Y | E | C | P | E | C | G | K | A | F | S | Q | G | S | H | L | T | K | H | R | R | S | H | G | P | K | A |

S1-3, hunchback, mkr3, cKr1

```
        BamHI                                    EcoRI
5' AGAC GGATCC ATTGCANNNNNNNNNNNNNNNCTGTAG GAATTC GGA 3'
3' TCTG CCTAGG TAACGTNNNNNNNNNNNNNNNGACATC CTTAAG CCT 5'
```

Primer A:                              Primer B:
5' AGACGGATCCATTGCA                    GACATCCTTAAGCCT 5'

FIGURE 11

```
Clone         Group I
16            ttacaGATGACTCAGCTAC
17            ACACAGATGCCTCA
12            TACCAACACCAGATGCtgcaa
53            TTGCGGATGCCCGT
10            TACACAGATGGCA
44            CAGAGACAGTGGAtgcaa
35            tacagGATGGGAACATTCT
47            attgcaCGATGTCATGCCTA
46            GTCTGAGACCGCTGAtgcaa
              PuGATGPy Group II
50            ACTAGAGGATAGGG
18            ATACCTCACTGGGGATACtgtaag
7             catcagGATACGCGCCATGG
21            GTTGGATATGCAGA
39            CTACAGAGATACCTAAGCTT
24            TTGATATACGACGT
15            GGTCACATGATAAGTG
              PuGATAPy Group III
43            ATATAGGCATCCCG
49            GGGACCGCTAATAGtgcaa
13            TTCATAGACGCCTCTT
26            CATATCATAGCCGTG
              ATAG Group IV
22            AGCGTTGGATTCTA
23            TTCGCTAGTAATGCtgcaa
9             AGAGCAATATGATC
5             TTATTAGCCTCGCT
27            GTTAGTGTGCCA
36            CTCGCAGGGTTAGTtgc
19            TCTTCGCCAACTAGctg
```

FIGURE 12

S1-3 consensuses         GATAGATG
                         GATGATAG

*origins of replication:*

| | |
|---|---|
| ColA (1) | GTAACGATAGATGATGGT |
| ColA (2) | CTCAAGATGATAGTTACC |
| R. meliloti | CTTACGATAGATGCCAAT |
| C. crescentus (1) | ACCAGGATAGATGTGCTC |
| S. pombe | TTTGTGATAGATGTAGAG |
| Monkey ORS24 (1) | ATAGAGATAGATGTAGTT |
| Monkey ORS8 | ATTAAGATAGATGGTAAT |
| Monkey ORS (2) | ATAGAGATAGATGTATAT |
| C. crescentus (2) | TTGGGGATGATAGGCGAG |
| Human ARS1 | GGGAAGATGATAGAAAAT |

*transcription factors:*

| | |
|---|---|
| GATA-1 | $^A/_T$GATA$^A/_C$$^G/_C$ |
| NF-E1 | $^A/_G$$^A/_T$GAT$^A/_T$$^G/_A$$^G/_T$ |
| NF-E1-3 | TGATAG |
| AP-1 | TGA$^C/_G$T$^A/_C$A |
| E2A | $^A/_G$CAGNTG |

DNA BINDING PROTEIN S1-3

STATEMENT AS TO FEDERALLY SPONSORED RESEARCH

This invention was made at least in part with funds from the Federal Government, under Arkansas Experimental Program to Stimulate Competitive Research founded by the National Science Foundation, the Arkansas Science and Technology Authority and the University of Arkansas for Medical Sciences.

BACKGROUND OF THE INVENTION

Replicative senescence, the finite replicative limit of human diploid fibroblasts Biological aging, an inevitable process common to multicellular organisms, involves a progressive physiological decline and associated pathologic degeneration of tissues and organs. The fundamental basis of aging remains enigmatic (Goldstein, 1992; Dice, 1993). The discovery that human diploid fibroblasts (HDF) have a finite proliferative lifespan opened the way to explore aging at the cellular level (Hayflick, 1965). The major feature of senescent HDF is their inability to synthesize DNA due to G1 arrest and failure to traverse the G1/S boundary (Goldstein, 1990; Cristofalo and Pignolo, 1993). A further hallmark of senescence is the dominant effect of the senescent nucleus on DNA synthesis in the young nucleus, as demonstrated in experiments involving somatic cell fusions between young and old cells. Initiation of DNA synthesis in the young HDF nucleus was extinguished, but ongoing DNA synthesis was not (Norwood et al., 1974; Stein and Yanishevsky, 1981). Moreover, this effect is abrogated by blockers of RNA and protein synthesis indicating that inhibition of DNA synthesis depends upon one or more proteins and perhaps on a direct inhibitory action of RNA(s) (Norwood et al., 1990).

Human diploid fibroblast cells (HDF) cultured in vitro provide an excellent model system for the study of biologic aging (Hayflick 1965; Goldstein 1990). These cells possess a limited replicative lifespan ("senescence in vitro"), that can be measured as the $MPD_{max}$, the maximum number of Mean Population Doublings accruing until phaseout. However, the great majority of senescent cells remain viable and capable of carrying out all metabolic and macromolecular functions except semiconservative DNA synthesis.

In several large series of HDF cultures, the $MPD_{max}$ is inversely proportional to the age of the donor (reviewed in Goldstein 1989). Moreover, HDF from subjects with Werner syndrome (WS, see below for discussion) display a sharply curtailed growth capacity compared to age-matched controls (Thweatt, et al. 1993). Thus, physiologic rather than chronologic age determines the $MPD_{max}$, and HDF clearly count cell divisions, rather than calendar or metabolic time, to a critical limit (Goldstein 1990; Goldstein 1989). That the replicative lifespan of cultured fibroblasts from a diversity of animal species is directly proportional to the maximum life expectancy of these species (ranging from two years to 150 years) indicates the presence of powerful genetic determinants of cellular senescence (Goldstein 1990; Goldstein 1992). Taken together, the data suggest a critical connection between senescence of HDF in vitro and biologic aging in vivo.

Dominance of the senescent phenotype in HDF

Cell fusion experiments have guided the search for root causes of HDF senescence. In repeated attempts at forming proliferating cell hybrids, young HDF (yHDF) failed to rescue senescent HDF (SHDF) after cell fusion, but permanent lines were able to do so (Goldstein, 1971). In short-term cell hybrids containing a senescent and a young nucleus within a single cytoplasm, i.e. heterocaryons, initiation of DNA synthesis in the yHDF nucleus was extinguished (Goldstein, 1971) but ongoing DNA synthesis was not (Yanishevsky, et al. 1980; reviewed in Norwood, et al. 1990). Brief post-fusion treatment of such heterocaryons with blockers of RNA and protein synthesis abrogated the inhibition (Norwood, et al. 1990).

Taken together, these data indicate that senescence is a dominant trait mediated by proteins or perhaps RNAs. In strong support of this concept, Lumpkin, Smith and coworkers microinjected polyA$^+$RNA from sHDF into yHDF and were able to inhibit DNA synthesis (Lumpkin, et al. 1986).

Relationship between HDF senescence and negative growth regulation

The primary mechanism by which senescent cells irreversibly lose the ability for transit through the G1/S checkpoint of the cell cycle, which differentiates them from growth arrested (quiescent) cells, is yet to be discovered. It is obvious that quiescence (arrested) and senescence share many proteins in common whose activity lead to the inhibition of DNA synthesis. Recently discovered proteins controlling cell cycle progression belong to this category. Their function is to inhibit activity of cyclin dependent kinase-cyclin (CDK-cyclin) complexes. These proteins are termed CDK inhibitory proteins (CKIs) and appear to be responsible for braking the cell cycle. Some of these proteins are activated in response to extracellular signals, while others appear to function intrinsically during the cell cycle (reviewed in Hunter 1993 and Peters, et al. 1994).

The p21 protein was initially identified by functional cloning of a gene sequence (SDI1) coding for an inhibitor of DNA synthesis and is overexpressed in sHDF at a level approximately 10–20 times the level seen in yHDF (Noda, et al. 1994). The identical protein was discovered virtually simultaneously by three other laboratories investigating systems unrelated to senescence, p21 and CIPI were isolated by their ability to bind and inhibit Cdk2-cyclin A and Cdk2-cyclin E complexes activities (Xiong, et al. 1993; Harper 1993), and WAF1 was induced by p53 protein in response to DNA damage, leading to transient cell cycle arrest by inhibiting CDKs (El-Deiry, et al. 1993; Dulic, et al. 1994).

Another negative regulator of cell cycle transit named p16, identified by its association with Cdk4 in the yeast two-hybrid protein interaction system, appears to specifically inhibit Cdk4-cyclin D kinase activity in vitro (Serrano, et al. 1993). A major target of this kinase seems to be the retinoblastoma product (Rb), which must be phosphorylated for proper progression through GI phase. Available data support the proposal that p16 prevents phosphorylation of Rb (Serrano, et al. 1993). Closely related studies, primarily by Stein and co-workers, have analyzed the role of Rb in HDF senescence. Following serum stimulation Rb remains underphosphorylated in sHDF, in contrast, phosphorylated Rb is abundant following serum stimulation of quiescent (arrested) yHDF (Stein, et al. 1990). Moreover, underphosphorylated Rb in sHDF is associated with the failure to express Cdc2, cyclin A and cyclin B (Stein, et al. 1991; Richter, et al. 1991), the inability to phosphorylate the Cdk2-cyclin E complex (despite its elevated protein level), and the attenuation of Cdk2-cyclin D1 and Cdc2-cyclin A complexes activities (Dulic, et al. 1993). The intrinsic cell cycle machinery is controlled by external signals such as growth factors and antimitogens which allows for coordination of cell division with environmental and developmental stimuli. TGF-β which can exhibit antimitogenic activity (Moses, et al. 1990) is known to play a role in expression of certain mRNAs and proteins like fibronectin, α(I)collagen, thrombospondin and SPARC/osteonectin (Penttinen, et al. 1988; Reed, et al. 1994), which are overexpressed in sHDF and WS HDF (Murano, et al. 1991), and also has been associated with the inhibition of the Cdk2-cyclin E complex kinase activity (Koff, et al. 1993). The protein responsible for this inhibition, p27, recently has been identified as associated with the Cdk2-cyclin E complex in cells arrested by TGF-β (Polyak, et al. 1994; Polyak, et al. 1994; Toyoshima, et al. 1994). p27 also appears to be involved in cell cycle arrest imposed by contact inhibition (Polyak, et al. 1994).

Transcription factors and their role in senescence

Senescing cells undergo changes which suggest altered transcriptional regulation of gene expression. Because transcription factors are attractive candidates which may ultimately specify the senescent phenotype, many studies have been performed to describe the expression and activity of known transcription factors in senescent cells. These studies revealed that E2F transcription factor which is a positive regulator of several late G1 phase genes required for G1/S transition, is underexpressed in senescent cells and its activity is negatively regulated by the unphosphorylated form of Rb (Dimri, et al. 1994; Nevins 1992; Flemington, et al. 1993). Moreover in sHDF genes coding for transcription factors involved in the immediate early response to growth factors such as c-fos, Id-1h and Id-2h, appear to be irreversibly repressed (Dimri, et al. 1994; Seshadri, T. et al. 1990; Riabowol, et al. 1992; DeTata, et al. 1993; Hara, et al. 1994) or their binding activity is changed (Dimri, et al. 1994). However, there is a paucity of information about transcription factors as positive regulators of genes involved in inhibition of DNA synthesis and cell proliferation. Indeed a transcription factor specific for or overexpressed in senescent cells, has yet to be identified.

LIM proteins—a new family of transcription regulators

An important new family of proteins, the LIM protein family, has recently been described with roles in developmental and cell growth regulation. The LIM protein family, named for three of the originally identified protein members, lin-11 (Freyd, et al. 1990), isl-1 (Karlsson, et al. 1990), and mec-3 (way, et al. 1988), is defined by the presence of one to three repeats of a 52-residue segment containing two adjacent zinc binding domains separated by a two-residue linker $(CX_2CX_{17}HX_2C)-X_2-(CX_2CX_{17}CX_2C/H/D)$. Although the LIM domain consists of two "zinc finger" domains, a controversy still remains about its DNA binding activity (Sanchez-Garcia, et al. 1994). Several studies indicate that it serves rather as a protein binding interface (Schmeichel, et al. 1994).

The LIM family consists of a variety of proteins with diverse functions and subcellular distributions; it includes transcription factors, protooncogene products and components of adhesion plaques. Based on the protein structure one can categorize the LIM family into three different groups. First, proteins containing a DNA binding homeodomain and a transcription activation domain adjacent to the LIM domains. This subfamily includes transcription factors involved in cell fate determination and differentiation as lin-11, isl-1 and mec-3. The second group, named "LIM-only" proteins, consists of several members that do not contain any additional known functional domains except LIM domains. LIM-only proteins appear to be involved in the regulation of gene activity even if they do not bind to DNA themselves. This group includes among others the protooncogene rhombotin-1, focal adhesion protein zyxin, cysteine-rich intestinal protein CRIP (Sanchez-Garcia, et al. 1994) and three newly discovered proteins with roles in the control of cell proliferation. MLP—muscle LIM protein plays a role in muscle differentiation by driving undifferentiated cells out of the cell cycle, a crucial step for initiation of the differentiation process (Arber, et al.). The protein ril was isolated from a revertant of ras-transformed cells and seems to be involved in the maintenance of normal cell growth (Kiess, et al. 1995). This gene is expressed in a variety of normal differentiated cells but is down-regulated in ras-transformed cells suggesting its function as a negative growth regulator. Another member of the LIM-only group, hic-5 protein was originally isolated from a mouse osteoblastic cell line whose growth was inhibited by TGF-β1 (Shibanuma, et al. 1994). Hic-5 expression is also repressed in ras-transformed fibroblasts as well as in several cell lines established from human tumors. On the other hand the level of its transcript accumulates during senescence in vitro and its overexpression driven by the cytomegalovirus promoter suggests that hic-5 has a cytostatic effect on cell growth (Shibanuma, et al. 1994).

Third, a recently described group of proteins which in addition to LIM domains also contain a protein kinase activity, is represented by two members: Kiz-1, with a role in cell proliferation and neuron differentiation (Bernard, et al. 1994), and LIMK specific for lung tissue (Ohaski, et al.). The specific function for both proteins is not yet known, but there is evidence for their nuclear localization.

Differential gene expression during cellular senescence

Werner syndrome (WS) provides an excellent model for the study of aging because it is a genetically-determined syndrome with features of premature aging (Thweatt, et al. 1993; Goldstein 1978; Salk 1982). The multifaceted pathology that occurs sporadically during aging of normal persons appears almost universally in WS subjects, which becoming manifest earlier and with greater severity. Without exception, HDF derived from WS subjects display a curtailed replicative lifespan and also yield a dominant inhibition of DNA synthesis in hybrid cell fusions with normal yHDF (Salk 1982; Tanaka, et al. 1980). The in vitro observations lead to the prediction that the genes responsible for inhibition of DNA synthesis should be overexpressed in WS cells (Murano, et al. 1991; Goldstein, et al. 1989).

SUMMARY OF THE INVENTION

In general, a novel polypeptide, designated S1-3, is identified and characterized. The mRNA for this protein is preferentially overexpressed in senescent human fibroblast cells or fibroblast cells derived from a patient with Werner Syndrome and specifically binds to DNA through three zinc finger domains.

S1-3 DNA clone, isolated from cells undergoing a process of premature senescence, codes for a novel DNA-binding "zinc finger" protein. Microinjection of S1-3 antisense or S1-3 partial sense RNA into non-proliferating human fibroblasts stimulates DNA synthesis, which indicates S1-3 role in the inhibition of DNA synthesis. S1-3 protein binds specifically to DNA and its binding site consensus sequence is found in many origins of DNA replication and overlaps a number of defined DNA binding sites for major transcription factors (GATA-1, NF-E1, AP1 and E2A) that have established function in cell proliferation and differentiation. This data indicates that S1-3 protein is an inhibitor of cell growth either as a regulator of DNA replication or regulator of transcriptional activity of other transcription factors.

The invention includes a substantially pure DNA encoding a DNA binding protein, a strand of which DNA will hybridize at high stringency to a probe consisting of 15 nucleotides of FIG. 2 (SEQ ID NO:1; human S1-3). The protein encoded by the DNA of the invention may share at least 80% sequence identity (preferably 85%, more preferably 90%, and most preferably 95%) with the amino acids listed in FIG. 2 (SEQ ID NO:2.)

More preferably, the DNA includes the coding sequence of the nucleotides of FIG. 2 (SEQ ID NO:1; human S1-3 cDNA), or a degenerate variant of such a sequence.

The probe to which the DNA of the invention hybridizes preferably consists of at least 20 nucleotides, more preferably 40 nucleotides, even more preferably 50 nucleotides, and most preferably 100 nucleotides or more (up to 100%) of the coding sequence of the nucleotides listed in FIG. 2 (SEQ ID NO:1) or the complement thereof. Such a probe is useful for detecting expression of S1-3 in a cell by a method including the steps of (a) contacting mRNA obtained from the cell with the labeled hybridization probe; and (b) detecting hybridization of the probe with the mRNA.

This invention also includes a substantially pure DNA containing at least 15 nucleotides (preferably 20, more preferably 30, even more preferably 50, and most preferably all) of the region from nucleotides 2 to 673 of the nucleotides listed in FIG. 2 (SEQ ID NO:1), a region of FIG. 2 (SEQ ID NO:1) which includes three zinc binding domains located between nucleotides 50 and 133 [See amino acids in FIG. 3B(a)], 134 and 220 [See amino acids in FIG. 3B(b)], and 392 and 475 [See amino acids in FIG. 3B(c)].

By "high stringency" is meant DNA hybridization and wash conditions characterized by high temperature and low salt concentration, e.g., wash conditions of 65° C. at a salt concentration of approximately 0.1×SSC. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is free of the genes which, in the naturally-occurring genome of the organism from which the DNA of the invention is derived, flank the gene of interest. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or CDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in FIG. 2 (SEQ ID NO:1) which encodes an alternative splice variant of S1-3.

The DNA may have at least about 70 sequence identity to the coding sequence of the nucleotides listed in FIG. 2 (SEQ ID NO:1), preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The invention also includes a vector containing a DNA encoding a polypeptide which includes the amino acid sequence of FIG. 2 (SEQ ID NO:2), e.g., a construct in which the coding sequence is operably linked to a promoter or other regulatory sequences for expression of the polypeptide, and a cell containing such a vector. The cell may be procaryotic or eukaryotic and preferably expresses the recombinant polypeptide encoded by the nucleotides listed in FIG. 2 (SEQ ID NO:1).

A "vector" is defined as a replicable nucleic acid construct, e.g., a plasmid or viral nucleic acid. Vectors may be used to amplify and/or express nucleic acid encoding S1-3 protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable MRNA ribosomal binding sites, and sequences which control the termination of transcription and translation. Methods which are well known to those skilled in the art can be used to construct expression vectors containing appropriate transcriptional/translational control signals. See for example, the techniques described in Sambrook et al., 1989, Molecular Cloning: A Laboratory Manual (2nd Edition), Cold Spring Harbor Press, N.Y., which are incorporated by reference. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

As stated above, the invention features a cell preferably expressing the recombinant polypeptide encoded by the nucleotides listed in FIG. 2 (SEQ ID NO:1). This cell can be a prokaryotic cell, e.g. an *Escherichia coli* cell, or a eukaryotic cell. Eukaryotic cells that can be used in the invention include, but are not limited to, COS, CHO, HeLa, and Sf9 cells. In the case of a eukaryotic cell, the gene may or may not be integrated into the genome of the cell. Also included in the invention is an essentially homogeneous population of prokaryotic or eukaryotic cells, each of which contains (i.e., is transfected with) a recombinant S1-3 gene. Transfection can be transient or stable, and if desired can be carried out in vivo or ex vivo, using the patient's own cells.

The invention also includes a substantially pure DNA S1-3 protein (a) being a DNA binding protein containing three zinc finger domains, (b) whose mRNA is overexpressed in senescent human diploid fibroblasts or human diploid fibroblasts derived from a patient with Werner Syndrome, and (c) whose mRNA is not expressed in fetal human diploid fibroblasts.

By "DNA binding protein" is meant a protein having the amino acid sequence of a protein that preferentially binds to DNA. Thus, S1-3 protein specifically binds to DNA. The mRNA corresponding to the S1-3 protein is overexpressed in senescent human diploid fibroblasts.

By "zinc finger domain" (1) is meant a member of the $C_2H_2$ zinc finger protein family; (2) is meant a region of S1-3 protein that plays a key role in the ability of S1-3 protein to bind to DNA and this reaction is $Zn^{2+}$ dependent; (3) is meant a region of S1-3 protein that plays a role in regulating expression of S1-3; (4) zinc finger domain #1 is characterized by nucleotides 50–133 of FIG. 2 (SEQ ID NO:3); (5) zinc finger domain #2 is characterized by nucleotides 134–220 of FIG. 2 (SEQ ID NO:4); and (6) zinc finger domain #3 is characterized by nucleotides 392–475 of FIG. 2 (SEQ ID NO:5).

Preferably, the protein includes the amino acid sequence of SEQ ID NO:2 (human S1-3), e.g., in the form of a S1-3 fusion protein. By "protein" is meant any chain of amino acids, regardless of length or post-translational modification (e.g., glycosylation or phosphorylation). The amino acid sequence of the protein preferably differs from SEQ ID NO:2 solely by conservative amino acid substitutions, e.g., substitution of one amino acid for another of the same class (e.g., valine for alanine, arginine for lysine, etc.) or by one or more non-conservative substitutions, deletions, or insertions located at positions of the amino acid sequence where the changes do not destroy the function of the protein (e.g., binding to antibody specific to an epitope corresponding to one of the three zinc finger domains of S1-3). Preferably, the amino acid sequence of the DNA binding protein S1-3 is at least 80%, more preferably 85%, more preferably 90%, and most preferably 95% identical to SEQ ID NO:2.

By a "substantially pure protein" is meant a protein which has been separated from those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure S1-3 protein may be obtained, for example, by extraction from a natural source (e.g., old human diploid fibroblasts); by expression of a recombinant nucleic acid encoding an S1-3 polypeptide; or by chemically synthesizing the protein. Purity can be measured by any appropriate method, e.g., column chromatography such as immunoaffinity chromatography using an antibody specific for S1-3, polyacrylamide gel electrophoresis, or HPLC analysis. A protein is substantially free of naturally associated components when it is separated from those contaminants which accompany it in its natural state. Thus, a protein which is chemically synthesized or produced in a cellular system different from the cell from which it naturally originates will be, by definition, substantially free from its naturally associated components. Accordingly, substantially pure proteins include those derived from eukaryotic organisms but synthesized in E. coli or other prokaryotes.

Also included in this invention is at least 20 nucleotides of substantially pure DNA from the region of nucleotides 2 to 673 of FIG. 2 (SEQ ID NO:1).

Also, this invention includes at least 20 nucleotides of substantially pure DNA encoding zinc finger domain #1. This region is also defined as nucleotides 50 to 133 of FIG. 2 (SEQ ID NO:1). The amino acid sequence of zinc finger domain #1: V F R C D K C T F T C S S D E S L Q Q H I E K H N E L K (See FIG. 3B (a)) (SEQ ID NO:3).

Also, this invention includes at least 20 nucleotides of substantially pure DNA encoding zinc finger domain #2. This region is also defined as nucleotides 134 to 220 of FIG. 2 (SEQ ID NO:1). The amino acid sequence of zinc finger domain #2: P Y K C Q L C Y Y E T K H T E E L D S H L R N E H K V S R. See FIG. 3B (b) (SEQ ID NO:4).

The transactivation domain with the coiled-coil structure as observed between zinc finger domain #2 and zinc finger domain #3 corresponds to amino acids 221 to 391 of FIG. 2 (SEQ ID NO:2). See shadowed box in FIG. 3A.

Also, this invention includes at least 20 nucleotides of substantially pure DNA encoding zinc finger domain #3. This region is also defined as nucleotides 392 to 475 of FIG. 2 (SEQ ID NO:1). The amino acid sequence of zinc finger domain #3: R F P C E F C G R A F S Q G S E W E R H V L R H G M A L (See FIG. 3B (c)) (SEQ ID NO:5).

The chart below lists which nucleotides or amino acids the different SEQ ID NOs correspond to, as well, as which figures these sequences appear in.

COMPARISON CHART

| SEQ ID NO: | CORRESPONDS TO: | AS SHOWN IN FIGURE |
|---|---|---|
| 1 | Nucleotides 1–1161 | FIG. 2 |
| 2 | Amino Acids 1–224 | FIG. 2 |
| 3 | Zinc Finger Domain #1; Nucleotides 50–133 | FIG. 2 and FIG. 3B (a) |
| 4 | Zinc Finger Domain #2; Nucleotides 134–220 | FIG. 2 and FIG. 3B (b) |
| 5 | Zinc Finger Domain #3; Nucleotides 392–475 | FIG. 2 and FIG. 3B (c) |
| 6 | G A T A G A T G | FIG. 12 |
| 7 | G A T G A T A G | FIG. 12 |

In addition to substantially full-length proteins, the invention also includes fragments (e.g., antigenic fragments) of the S1-3 proteins. As used herein, "fragment," as applied to a polypeptide, will ordinarily be at least 10 residues, more typically at least 20 residues, and preferably at least 30 (e.g., 50) residues in length, but less than the entire, intact sequence. Fragments of the S1-3 protein can be generated by methods known to those skilled in the art, e.g., by enzymatic digestion of naturally occurring or recombinant S1-3 protein, by recombinant DNA techniques using an expression vector that encodes a defined fragment of S1-3, or by chemical synthesis. The ability of a candidate fragment to exhibit a characteristic of S1-3 (e.g., binding to an antibody specific for S1-3) can be assessed by methods described herein. Purified S1-3 or antigenic fragments of S1-3 can be used to generate new antibodies or to test existing antibodies (e.g., as positive controls in a diagnostic assay) by employing standard protocols known to those skilled in the art. In one preferred embodiment, a monoclonal antibody is generated using one of the three zinc finger domains which corresponds to an amino acid sequence that is not homologous to the sequence of any other known proteins, to immunize an appropriate laboratory animal, such as a mouse. Also included in this invention are polyclonal antisera generated by using S1-3 or a fragment of S1-3 as the immunogen in, e.g., rabbits. Standard protocols for monoclonal and polyclonal antibody production known to those skilled in this art may be employed. The monoclonal antibodies generated by this procedure can be used to verify the identity of recombinant S1-3 cDNA clones.

Also included in the invention are S1-3 proteins which are encoded at least in part by portions of SEQ ID NO:1, e.g., products of alternative MRNA splicing or alternative protein processing events, or in which a section of S1-3 sequence has been deleted. The fragment, or the intact S1-3 polypeptide, may be covalently linked to another polypeptide, e.g. which acts as a label, a ligand or a means to increase antigenicity.

The invention also includes a polyclonal or monoclonal antibody which specifically binds to S1-3. Preferably, this antibody specifically binds to an epitope in one of the three zinc finger domains of S1-3 which corresponds to a sequence shown is FIG. 3B (a), (b), and (c), respectively (SEQ ID NOs: 3, 4, and 5, respectively). The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In preferred embodiments, the antibody, or a fragment thereof, may be linked to a toxin or to a detectable label, e.g. a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc.

Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) JACC 14, 472–480; Shreve et al., (1986) Magn. Reson. Med. 3, 336–340; Wolf, G. L., (1984) Physiol. Chem. Phys. Med. NMR 16, 93–95; Wesbey et al., (1984) Physiol. Chem. Phys. Med. NMR 16, 145–155; Runge et al., (1984) Invest. Radiol. 19, 408–415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) Clin. Chim. Acta 70, 1–31; and Schurs et al., (1977) Clin. Chim. Acta 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting S1-3 DNA binding protein in a biological sample, which includes the steps of contacting the sample with the labelled antibody, e.g., radioactively tagged antibody specific for S1-3, and determining whether the antibody binds to a component of the sample. Antibody binding indicates that the sample contains a S1-3 polypeptide, and consequently, contains a DNA binding protein with zinc finger domains.

Diagnostic Uses and Advantages

As described herein, the invention provides a number of diagnostic advantages and uses. For example, the DNA binding protein S1-3 may be useful in diagnosing premature senescence.

Antibodies (or antigen-binding fragments thereof) which bind to an epitope specific for S1-3, e.g., one of the three different zinc finger domains, are useful in a method of detecting DNA binding protein S1-3 in a biological sample for diagnosis of premature senescence. This method includes the steps of obtaining a biological sample (e.g., blood, plasma, tissue, etc.) from a patient suspected of having a premature senescence condition, contacting the cells of the sample with a labelled antibody (e.g., radioactively tagged antibody) specific for S1-3, and detecting the S1-3 antibody using standard immunoassay techniques such as an ELISA. Antibody binding to the biological sample indicates that the sample contains a component which specifically binds to an epitope within S1-3, e.g., one of the three different zinc finger domains. This binding would be indicative of a premature senescence condition.

Likewise, a standard Northern blot assay can be used to ascertain the relative amounts of S1-3 mRNA in a cell or tissue obtained from a patient suspected of a premature senescence condition, in accordance with conventional Northern hybridization techniques known to those persons of ordinary skill in the art. This Northern assay uses a hybridization probe, e.g. radiolabelled S1-3 cDNA, either containing the full-length, single stranded DNA having a sequence complementary to SEQ ID NO:1 (FIG. 2) , or a fragment of that DNA sequence at least 20 (preferably at least 30, more preferably at least 50, and most preferably at least 100 nucleotides in length). Most preferably, the DNA hybridization probe would be complementary to a portion of FIG. 2 (SEQ ID NO:1) encoding one, two, or all three identified zinc finger domains, particularly a part which is not homologous to any previously known DNA sequence. The DNA hybridization probe can be labelled by any of the many different methods known to those skilled in this art.

Antibodies to the S1-3 protein can be used immunohistochemically to identify the presence of S1-3 in tissues suspected of a premature aging condition. Also, antibodies to the S1-3 protein can be used in an immunoassay to detect reduced levels of S1-3 protein expression in tissues suspected of neoplastic transformation. This would be useful for testing older patients with an elevated S1-3 expression due to their age progression. These same uses can be achieved with Northern blot assays and analyses.

Therapeutic Uses and Advantages

As described herein, the invention provides a number of therapeutic advantages and uses. The data presented herein demonstrates that the S1-3 gene sequence may play role in regulation of DNA replication, cell growth and differentiation. Thus, as an anti-cancer therapeutic, causing the overexpression S1-3 mRNA in cancer cells could lead to inhibition of cell growth.

This invention also includes a method of treating a patient suspected of having cancer whereby a patient suspected having cancer is identified, and then an effective amount of S1-3 protein is administered to the patient wherein such amount of S1-3 protein will inhibit DNA synthesis.

This invention further includes a method of treating premature senescence condition whereby such a patient is identified and then treated with an effective amount of S1-3 antisense RNA.

Also, therapeutic uses of S1-3 protein can be based on the inhibition of cell division (DNA synthesis) through the overexpression of this protein by transfecting cells with a retroviral vector comprising and expressing the S1-3 gene. This will allow the constant overexpression of S1-3 mRNA and protein in target cells, e.g., neoplastic cells.

For administration to human patients, antibodies specific for S1-3 can be humanized by methods known in the art, e.g, by a commercial service (Scotgene, Scotland; Oxford Molecular, Palo Alto, Calif.). Monoclonal antibodies can be purified using known methods, such as absorption onto immobilized Protein A or immunoaffinity chromatography. Following purification, the MAbs of the invention or immunologically active fragments thereof, e.g., Fab, (Fab)$_2$, or Fv, can be administered to patients in a pharmaceutically acceptable excipient such as physiological saline. The MAbs and/or antibody-based compounds of the invention, e.g., MAbs linked to therapeutic agents, can be administered by any standard route including intraperitoneally, intramuscularly, subcutaneously, intravenously or intra-arterially. It is expected that the preferred route of administration will be intravenous or intra-arterial. These compounds can be administered systemically to the bloodstream as well as locally within the blood vessel at the site of clot formation.

As is well known in the medical arts, the dosage for any one patient will depend on many factors, including the patient's general health, extent of disease, sex, size, body surface area, and age, as well as the particular compound to be administered, time and route of administration, and other drugs being administered concurrently. Dosages for compounds of the invention will vary, but a preferred dosage for intravenous administration is approximately 1 $\mu$g to 500 $\mu$g/ml blood volume. Determination of correct dosage for a given application is well within the abilities of one of ordinary skill in the art of pharmacology.

The therapeutic agents described herein may be linked to an antibody specific for S1-3 using a covalent bond, such as a disulfide bond or a covalent crosslinking agent, by employing standard protocols well known in the art.

For this invention, HDF means human diploid fibroblast cells.

By yHDF is meant young HDF.

By sHDF is meant senescent HDF. By OHDF is meant old HDF. For this invention, old HDF or OHDF and sHDF are used interchangeably.

By MPD$_{max}$ is meant the maximum number of Mean Population Doublings accruing until phaseout.

Other features and advantages of the invention will be apparent from the following detailed description, and from the claims.

BRIEF DESCRIPTION OF THE DRAWINGS

FIGS. 2A, 2B, and 2C shows the nucleotide and deduced amino acid sequence of the largest insert obtained for S1-3. The nucleotides and amino acids are numbered in relation to the first nucleotide of the clone.

FIG. 3B is a comparison of aligned "zinc finger" sequences. FIG. 3B (a) represents zinc finger domain #1; FIG. 3B (b) represents zinc finger domain #2; and FIG. 3B (c) represents zinc finger domain #3. Three S1-3 "zinc finger" domains are aligned with representative domains from transcription factors with highest homology to S1-3 clone. "hunchback": D. melanogaster hunchback; "mkr3": murine Kruppel-like protein; and "ckr1": chicken Kruppel-like protein. The bottom line represents the sequence for the S2-6 "zinc finger", part of LIM domain. Amino acids with involved in zinc binding are boxed by solid lines; highly conserved amino acids are boxed by dotted line.

FIG. 8 is schematic representation of a degenerate oligonucleotide library with 14 degenerate positions (N) containing A, C, G or T. The 5' end of the oligonucleotide contains a BamHI restriction endonuclease site (boxed), and the 3' end contains an ECoRI restriction endonuclease site (boxed). Complementary PCR primers were synthesized for the 5' sense strand (primer A) for the 3' antisense strand (primer B).

FIG. 11 is a comparison of aligned S1-3 DNA binding site consensus sequence Groups I, II, III, and IV observed in different clones. Lower case letters indicate nucleotides that belong to linkers. Bold characters in Group IV indicate conserved bases.

FIG. 12 is a comparison of homologies to S1-3 DNA binding site consensus sequence found in various origins of replication and DNA binding sites for transcription factors.

DETAILED DESCRIPTION

Figure 1:
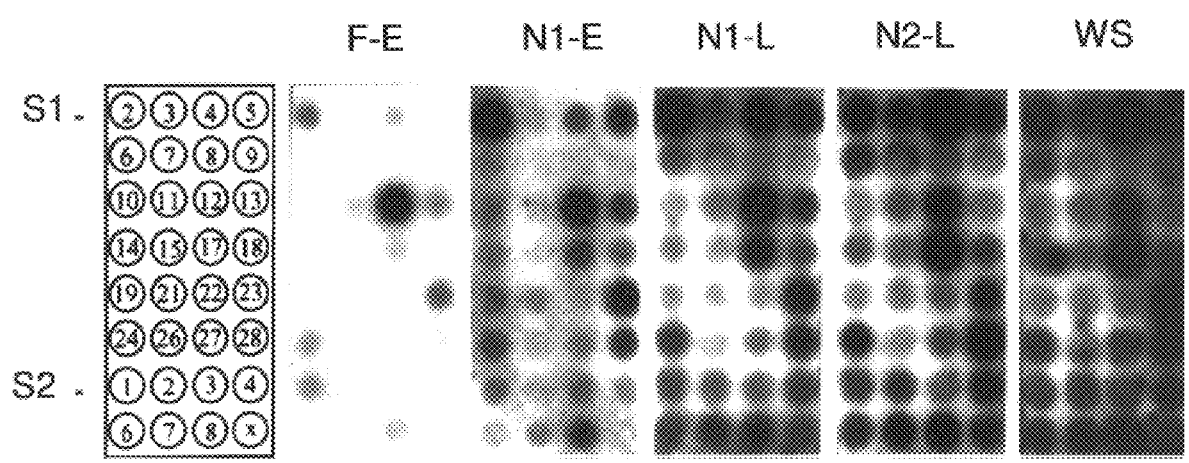
FIG. 1 is a photograph of dot-blots representing mRNA expression of clones, dependent on the cell type, derived from a subtracted WS fibroblast cDNA library.

The construction and screening of a senescent CDNA library provided an initial approach toward determining the identities of genes which may be causally involved in the senescence of HDF. In electing to doubly subtract, it was intended that this strategy would substantially increase the probability of revealing relatively non-abundant RNA transcripts of gene sequences that may play a regulatory role. The majority of cDNA clones isolated from the subtracted library are expressed at a very low level. With this double substraction technique, clones which may play a role in regulation of gene expression can be identified and further studied.

The rationale for using cultured WS cells as model cells is evident from the description on WS provided above.

Identification and Characterization of a Novel Gene Overexpressed in Senescent Cells To uncover transcripts of very low abundance coding for proteins with a possible regulatory function, a second, subtracted WS cDNA library (W8) was constructed in the XZAPII phage system (Stratagene). This system enabled gene inserts to be converted into single-stranded antisense cDNAs complementary to polyA+RNA, which facilitates subsequent subtractive enrichment of senescence-specific cDNAs. Two sequential steps of subtraction were performed on this cDNA library: (1) to deplete cDNAs corresponding to mRNAs common to young and senescent cells, e.g., housekeeping gene transcripts, and then (2) to deplete cDNAs that represented relatively abundant mRNAs, predominantly encoding proteins secreted into the extracellular matrix (ECM) and ECM-associated proteins, which had been identified as overexpressed in the first WS CDNA library.

I. Material and Methods

A. Cell Culture

Table 1 shows a variety of human diploid fibroblast cell lines available for use in these studies. Postnatal strains were derived from forearm skin biopsies. Skin fibroblast cultures from WS8 and WS12, two unrelated patients with classical Werner syndrome, were a generous gift from Dr. S. Murano, Chiba University (Chiba, Japan). HSC172 cells were derived from fetal lung fibroblasts. Cells were cultivated in regular growth medium (RGM) consisting of Eagle's minimum essential medium (MEM) supplemented with a 15% fetal bovine serum (FBS). Young HDF were defined as proliferatively competent cells in the first half of their replicative lifespan, while old HDF were cells with attenuated proliferative capacity in the last 10% of their replicative life span.

B. RNA Isolation

PolyA+RNA was isolated by Fast-Track kit (Invitrogen). Total RNA was isolated according to the acid guanidinium thiocyanate-phenol-chloroform method (Chomczynski and Sacchi, 1997). For Northern analysis, total and polyA+ RNAs were resolved on 1% agarose formaldehyde gels and transferred to ZETA Probe nylon membranes. RNA integrity, equality of loading, and evenness of transfer were assessed by control hybridizations to glyceraldehyde-3-phosphate dehydrogenase (GAPD) or β-actin cDNAs. All hybridizations were performed under high stringency conditions (Church and Gilbert, 1984).

TABLE 1

STRAINS OF HUMAN DIPLOID FIBROBLASTS USED

| Cell Strain | Age | Gender | Cell Type | Maximum Mean Populations Doublings |
|---|---|---|---|---|
| NORMAL | | | | |
| HSC172 | fetal | ♀ | lung | 62 |
| A25 | 9 | ♀ | skin | 48 |
| A2 | 11 | ♂ | skin | 54 |
| A23 | 23 | ♂ | skin | 56 |
| A8 | 31 | ♂ | skin | 56 |
| J065 | 56 | ♂ | skin | 44 |
| A33 | 70 | ♂ | skin | 35 |
| A35 | 76 | ♂ | skin | 33 |
| J088 | 76 | ♀ | skin | 44 |
| WERNER SYNDROME | | | | |
| WS12 | 46 | ♂ | skin | 19 |
| WS8 | 47 | ♂ | skin | 18 |

C. Construction of W8 cDNA Library

A WS CDNA library was constructed as previously described (Lecka-Czernik et al., 1995). Briefly, 5 μg of polyA+RNA isolated from WS8 cells six days after subculture in RGM was used as a template. The W8 CDNA library was constructed in the XZAPII system (Stratagene), which allows for unidirectional cloning, easy conversion of phage to plasmid form, and rescue as a single-stranded cDNA complementary to its mRNA as a Bluescript phagemid. The complexity and quality of the library were checked by screening with a cDNA corresponding to the 3' untranslated region (UTR) of β-actin cDNA (Ponte et al., 1984). The W8 cDNA library, before amplification, consisted of $2.6 \times 10^5$ independent cDNA clones.

D. Biotinylation

PolyA+RNA was biotinylated using Photoprobe-Biotin (Vector Laboratories), a photoactivatable form of biotin (PAB). Ten micrograms of polyA+RNA were resuspended in 10 μL of 0.1 mM EDTA, pH 8.0, mixed with an equal volume of Photoprobe-Biotin stock solution (1 μg/L) and irradiated for 15 min in an ice bath, 10 cm below a sunlamp (wave length 350–370 nm). Following labeling sample volume was increased to 100 μL by the addition of 0.1 M Tris-HCl, pH 9.5, and unreacted PAB was removed by repeated extraction with an equal volume of 2-butanol. RNA was subjected to a second biotinylation reaction, followed by 2-butanol extractions and [PAB]RNA ethanol precipitation.

E. Subtraction

Single-stranded (ss)DNA representing Bluescript phagemid containing CDNA inserts was rescued from the XZAPII W8 library using R408 helper phage according to Schweinfest et al. (1990). Subtractive hybridization was carried out according to Schweinfest et al. (1990), Duguid et al. (1988), and Sive and St. John (1988), with modifications. [PAB]RNA (10 µg) from cell strain HSC172 representing normal fetal HDF was co-precipitated with 1 µg of ssDNA, 1 µg poly(A) and 1 µg poly(C) in the presence of glycogen. The precipitate was dissolved in 5 µL of HE (10 mM Hepes, pH 7.5, 1 mM EDTA) and 5 µL of 2×HB (1×0.5 M NaCl. 50 mM Hepes, pH 7.6, 2 mM EDTA, 0.2% SDS). The hybridization mixture was overlaid with mineral oil, heated at 95° C. for two minutes, and incubated at 65° C. for 45 h to achieve $R_o t \approx 3000$, necessary for promotion of hybridization between rare RNA sequences. To remove ssDNA-[PAB] RNA hybrids and unhybridized [PAB]RNA, hybridization mixture was diluted 10-fold with HB-SDS (without SDS) and 10 mg of avidin D covalently linked to VECTREX matrix (Vector) was added. The mixture was then incubated at 60° C. for 30 min with rotary agitation and centrifuged for 30 s at 3000×g. The supernatant was collected. Resins were washed three times with 100 µL HB-SDS, and combined supernatants were incubated again with 10 mg of VECTREX-Avidin D followed by consecutive washing as above. Collected supernatant was combined, extracted once with phenol:chloroform, once with chloroform, and ethanol precipitated. To rescue ssDNA from the complex with [PAB]RNA, VECTREX-Avidin D resins used for subtraction were incubated for 15 min at 95° C. in the presence of 200 µL HB-SDS, cooled on ice, centrifuged, extracted with phenol:chloroform and chloroform, and precipitated as above. The efficiency of subtraction was examined by dot-blot hybridization of β-actin CDNA probed with [$^{32}$P]-labeled ssDNA present in the collected supernatants. We compared the level of signal achieved using as a probe either DNA remaining as unhybridized fragments or DNA rescued from [PAB]RNA-DNA hybrids. A 100-fold reduction in signal wa seen in blots hybridized to the remaining ssDNA, which indicated a high level of subtraction. The second round of subtraction was performed with in vitro transcribed RNAs (Krieg and Melton, 1984) representing clones previously identified as abundantly expressed in WS cells. RNAs were mixed in a ratio representing their abundance in the W8 cDNA library before subtraction and procedures were performed under the identical conditions as in the first round.

F. Transformation

The subtracted ssDNA was converted to double-stranded DNA prior to transformation into XL1Blue *E.coli*. Synthesis of the second DNA strand was performed using SK primer according to Schweinfest et al. (1990). Clones with cDNA insert were identified by color selection of colonies in the presence of X-Gal and IPTG. Isolated cDNA clones represented the subtracted W8 library referred to as sW8.

G. Differential Screening of sW8 Library

Differential (±) screening was performed with five replicate dot-blots containing 5 µg of immobilized plasmid DNA representing each cDNA clone from the sW8 library (Maniatis et al, 1989). Each blot was probed separately with a [$^{32}$P]-labeled cDNA derived from polyA$^+$RNA of different cell strains. Probes with high specific activity were achieved as follows. Annealing reaction was performed using 0.4 µg polyA$^+$RNA and 0.8 µg of random decamers. The mixture was heated at 70° C. for 10 min and chilled on ice. cDNA synthesis was performed using Superscript II Reverse Transcriptase (Gibco BRL). A typical reaction consisted of: 7 µL annealed polyA$^+$RNA with decamers, 4 µL 5× first strand buffer (Superscript II), 2 µL 0.1 M DTT, 1 µL dNTPs (10 mM of each except dCTP) and 5 µL [α-$^{32}$P]dCTP (spec. activity 3000 ci/mM). The mixture was warmed for two minutes at 37° C., 1 µL (200 U) Superscript II Reverse Transcriptase was added, and incubation continued for one hour at 37° C. Remaining template RNA was digested by 1 µL (1.5 U) RNaseH for 30 min at 37° C. and probes were purified on G-25 Sepharose spin-columns. The efficiency of labeling was ≈7.5×10$^7$ CPM/µg RNA. Hybridization was carried out under high stringency conditions using the same amount of specific radioactivity for each cDNA probe.

H. DNA Sequencing

DNA sequencing of double-stranded insert cDNA was performed with Sequenase (U.S. Biochemical) and synthetic oligonucleotide primers in the chain termination method (Sanger et al., 1977). A search of the GenBank/EMBL databases was conducted for sequence homology and analysis was performed with the Wisconsin Genetics Computer Group software package.

I. Deposit

Under the terms of the Budapest Treaty on the International Recognition of the Deposit of Microorganisms for the Purpose of Patent Procedure, a plasmid containing human S1-3 (S1-3 clone in the pBluscript SK™ vector (Stratagene) was deposited with the American Type Culture Collection (ATCC) of Rockville, Md., USA, on Jun. 28, 1996, and was given ATCC designation number 97643.

Applicant's assignee, President and Fellows of Harvard College, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

II. Results

A. Construction and Screening Of an Unsubtracted sW8 cDNA Library

This library was constructed for the purpose of isolating genes that are specifically expressed or overexpressed during aging.

A Werner syndrome (WS) cDNA library was first constructed in the Okayama-Berg eukaryotic expression vector. Differential screening of this library revealed eighteen distinct cDNAs whose cognate RNA transcripts were abundantly overexpressed in WS and normal sHDF, compared to yHDF (Murano, et al. 1991). Among the 18 cDNAs, nine clones encoded known proteins including α1(I) procollagen, α2(I) procollagen, fibronectin (FN), ferritin heavy chain, osteonectin (or SPARC), IGF binding protein-3 (IGFBP-3), thrombospondin, αB-crystallin and plasminogen activator inhibitor-1 (PAI-1). Some of them (e.g. IGFBP-3, SPARC, PAI-1 and FN) can inhibit DNA synthesis by modulating extracellular signals (Symington 1992; Grigoriev, et al. 1994). Overproduction of FN and PAI-1 can interfere with normal regulation of blood clotting and predispose to atherogenesis (Rasoamanantena, et al. 1994; Goldstein, et al. 1994). Excessive accumulations of SPARC and thrombospondin, by virtue of their $Ca^{2+}$-binding properties, could predispose to osteopenia and the tendency to develop osteoporosis (Thweatt, et al. 1993; Termin 1990).

Among the nine previously unknown clones, WS3-10 CDNA codes for a cystolic smooth muscle protein that putatively binds intracellular $Ca^{2+}$ and whose forced expression leads to suppression of $Ca^{2+}$-mediated membrane currents, similar to the suppressed currents that arise spontaneously in sHDF (Thweatt, et al. 1992; Liu, et al. 1994). The remaining seven clones contain the highly repetitive family of Alu elements, whose functional significance is unknown, but when introduced into HeLa cells appear to have an inhibitory effect on DNA synthesis (Sakamoto, et al. 1991).

It is noteworthy, that all of the cDNA clones isolated as overexpressed in WS HDF are also overexpressed in normal sHDF. In other words, once normal HDFs become senescent, they appear to generate the same downstream changes in genetic expression as prematurely senescent WS HDF. This bolsters the argument that a causal connection exists between senescence of HDF in vitro and biological aging in vivo.

B. Construction and Differential Screening of a Subtracted sW8 cDNA Library

Figure 13:
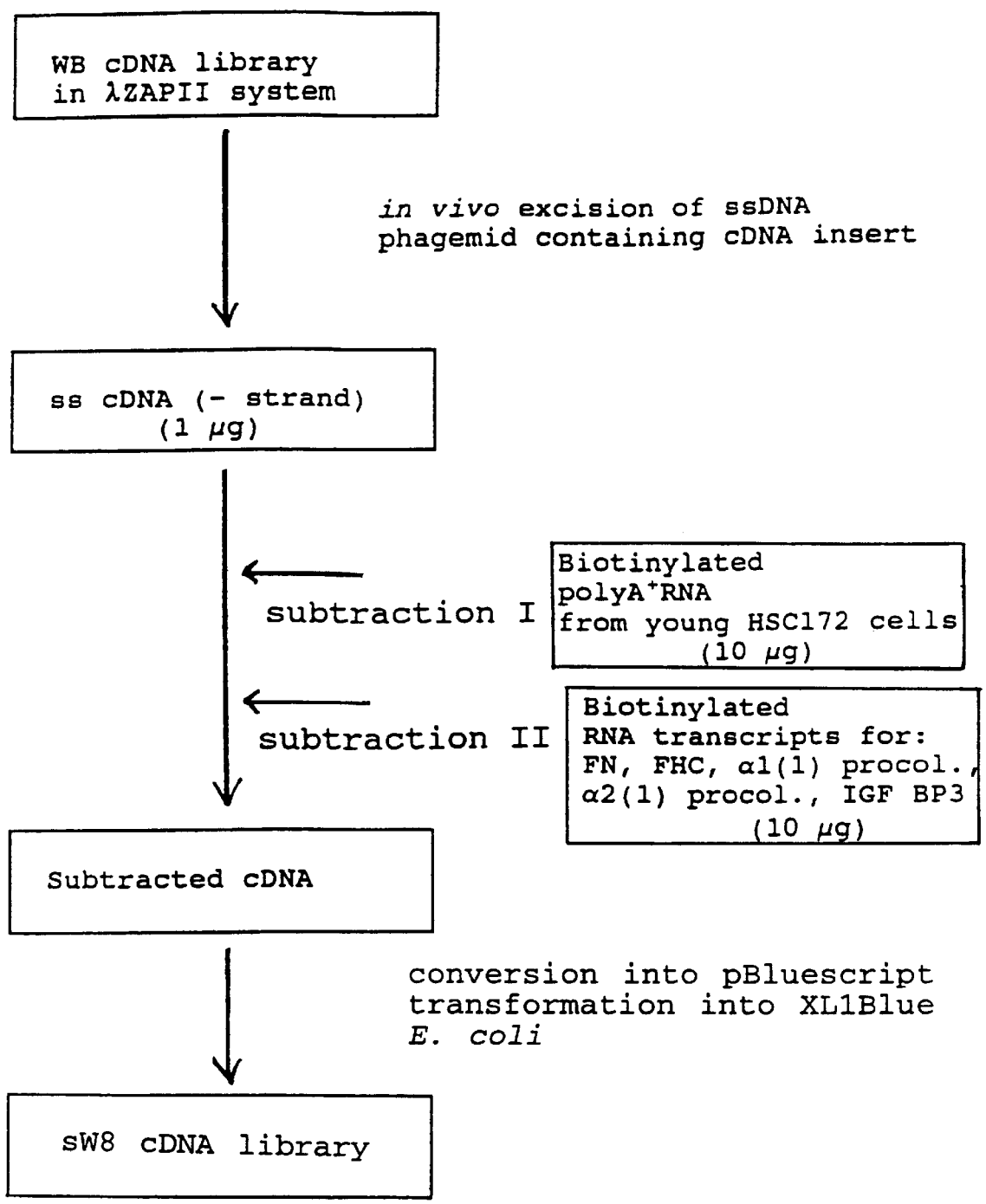
FIG. 13 is an outline of scheme representing construction of subtracted WS cDNA library.

To uncover transcripts of very low abundance coding for protein with a possible regulatory function, a second, subtracted WS CDNA library (W8) was constructed in the XZAPII phage system (Stratagene). This enabled the gene inserts to be converted into single-stranded antisense cDNAs complementary to polyA$^+$RNA, which facilitates efficiency of subsequent annealing and subtraction. Below two sequential steps of subtraction were performed on this cDNA library (see FIG. 13): Step (1) to deplete cDNAs corresponding to mRNAs common to young and senescent cells such as housekeeping gene transcripts; and then Step (2) to deplete cDNAs that represented relatively abundant mRNAs, predominantly encoding proteins secreted into the extracellular matrix (ECM) and ECM-associated proteins, which had been identified earlier in the first WS cDNA library.

In total, these two steps served to deplete cDNAs that represented mRNAs common to young and senescent cells, such as housekeeping gene transcripts, and sequences representing relatively abundant mRNAs, predominantly encoding secreted proteins that had been identified earlier as overexpressed in the first WS cDNA library (Murano et al., 1991).

First, antisense cDNAs were subtracted with biotinylated polyA$^+$RNAs obtained from vigorously growing, normal fetal fibroblasts (HSC172) followed by removal of duplexes and unannealed single-stranded RNA by avidin binding. Hybridization was done under high stringency conditions with a 10 fold excess of biotinylated polyA$^+$RNA. Hybrids between biotinylated MRNA and CDNA and unannealed mRNA were removed by avidin binding and phenol extraction (Schweinfest, et al. 1990).

In the second step, the remaining cDNAs were subtracted with biotinylated mRNAs transcribed in vitro from CDNA clones for FN, ferritin heavy chain, α1(I) procollagen, α2(I) procollagen and IGFBP-3, all of which were previously found to be overexpressed in the first WS library (Murano, et al. 1991). After subtraction, antisense single-stranded DNAs were converted to double-stranded DNA using the Klenow fragment of E.coli polymerase I, and this DNA was transfected into XL1Blue E.coli cells. This enabled the transformants to be screened for their possession of cDNA inserts in the presence of IPTG and X-gal, as inducer and indicator of β-galactosidase expression, respectively (Lecka-Czernik, et al. 1995 (in press)).

C. Differential Screening of the Subtracted WS cDNA Library

After these two subtraction steps, we obtained 31 different clones were obtained differentially screened on five replicate dot blots (FIG. 1). FIG. 1 is a photograph of an immunoblot representing a subtracted WS fibroblast cDNA library. $^{32}$P-labeled cDNAs derived from the following polyA$^+$RNAs were used as probes: (1) early-passage, vigorously growing fetal HDF; (2) early passage, postfetal normal HDF; (3) the same strain of normal postfetal cells nearing the end of their replicative lifespan ("old" or senescent HDF); (4) a second strain of normal postfetal late-passage HDF; and (5) prematurely senescent WS HDF. Five µg of plasmid DNA containing 31 specific CDNA inserts from the subtracted library identified in two stages (S1 and S2) and one CDNA from the previous unsubtracted library (ref. 41) for comparative purposes (WS19-9 indicated by x) were loaded on five replicate filters. Probes were prepared using 1 µg of polyA$^+$RNA derived from several cell types, primer extension by reverse transcriptase, dNTPs and 50 µCi[a-$^{32}$P]dCTP, followed by digestion of the remaining RNA with 1.5 U RNaseH and purification of probes on G-50 Columns. Hybridization was carried out at high stringency using $1 \times 10^7$ CPM/ml of each probe. Left panel, scheme depicting replicate dot blot arrays probed with $^{32}$p CDNA derived from: F-E, normal early-passage fetal fibroblasts (strain HSC172)MPD level 9 (MPD$_{max}$62); N1-E, normal early passage A2 skin fibroblasts at MPD 23 (11 year old donor, MPD$_{max}$=54); N1-L, A2 fibroblasts at late passage (MPD 51); N2-L, normal late-passage A25 skin fibroblasts at MPD (9 year old donor, MPD$_{max}$ 48); WS8 skin fibroblasts from a 46 year old WS subject at MPD 12 (MPD$_{max}$=18) (ref. 44).

As a result of this probing, the 31 clones were classified into four groups according to their levels of RNA expression. Clone S1-3, which is the subject of the instant invention, falls into Group I, but Groups II, III, and IV will also be briefly described.

Group I: Clones not expressed in fetal HDF, but overexpressed in Old HDF and WS HDF.

This group contains 9 distinct clones; one known (S1-9) and eight novel showing no homologies to known proteins. See Table 2 below. S1-9 encodes the enzyme acid sphingomyelinase whose MRNA accumulates in HDF in direct proportion to donor age (Lecka-Czernik, et al. 1995 (in press)). This enzyme is of interest since its catalytic cleavage of sphingomyelin generates ceramide, whose elevated level is implicated in senescence of HDF by its ability to promote growth arrest and repression of AP-1 transcription factor activity (Obeid 1994). Other well documented studies have shown that ceramide can trigger signal transduction pathways leading to activation of NFKB and the MAP kinase phosphorylation cascade, processes which can induce cell apoptosis in some experimental systems (Obeid, et al. 1993; Jarvis, et al. 1994; reviewed in Kolesnick, et al. 1994). S1-5 encodes a member of the EGF-like protein family with an EGF-like domain consensus sequence highly homologous to those present in several known extracellular proteins which play a role in cell growth, development and cell signaling, such as TGF-β1 binding protein (Kanzaki, et al. 1990), Notch multifunctional receptor (Wharton, et al. 1985) and nidogen (Mann, et al. 1989). S1-5 mRNA is overexpressed in normal SHDF and WS HDF, is induced by growth arrest in young normal cells, but is significantly decreased by high concentrations of serum, conditions which promote cellular proliferation (Lecka-Czernik, et al. 1995). Paradoxically, microinjection of S1-5 mRNA into yHDF stimulated DNA synthesis by an apparent autocrine/paracrine mechanism. Thus the S1-5 gene product may represent a negative and/or positive factor whose ultimate activity is modulated by the cell environment, a similarity it shares with other members of the EGF-like protein family. S1-3, the subject of this invention, encodes a hitherto unknown protein that contains three "zinc finger" domains, suggesting that it is a DNA binding protein (Klug, et al. 1987). S2-6 and S2-7 encode a new member of the LIM protein family (Sanchez-Garcia, et al. 1994). S1-15 shows a 70% similarity to human α2-chimerin (Hall, et al. 1993). The remaining 3 clones have no significant homology to known proteins.

(Fett, et al. 1991) and S2-3 has a 90% similarity and 69t identity to glycyl-tRNA synthetase from Bombyx mori (Nada, et al. 1993).

Group IV: Clones expressed at a similar level in all four cell types examined.

This group contains 3 clones, indicating incomplete subtraction.

Thus, the strategy to construct and screen a subtracted senescent cDNA library provided an approach to identity genes causally involved in the senescence of HDF. The subtractive strategy, in contradistinction to the nonsubtractive procedure applied in the first library, would more likely reveal relatively nonabundant gene sequences that play a regulatory role in cell proliferation. Because even ostensibly young cultures contain an admixture of senescent cells, housekeeping gene transcripts, common for young and old cells, were subtracted out using mRNA from normal, fetal lung fibroblasts (Harley and Goldstein, 1978). This resulted in isolation of 12 clones that seemed to be specific for skin, in contrast to lung fibroblasts and were equally expressed in young and old skin fibroblasts. Despite this, from the

TABLE 2

GROUP I CLONES mRNA OVEREXPRESSED IN OLD AND WS HDF AND NOT EXPRESSED IN FETAL CELLS

| cDNA CLONE | Levels of RNA Expression | | | | | mRNA (kb) | cDNA Sequenced (kb) | Identity/ Similarity | References |
|---|---|---|---|---|---|---|---|---|---|
| | F-E | N1-E | N1-L | N2-L | WS | | | | |
| S1-3 | − | + | ++ | ++ | ++ | 2.8; 1.8 | 1.2 | "Zinc Finger" protein | Klug and Rhodes, 1987 |
| S1-5 | − | ++ | +++ | +++ | +++ | 3.0; 2.2 | 3.0 | EGF-Like Family | Lecka-Czernik et al., 1995 |
| S1-7 | − | − | + | + | + | smear | 0.2 | None | |
| S1-8 | − | − | + | + | + | 5.4; 2.3; 1.3 | 0.2 | None | |
| S1-9 | + | + | ++ | ++ | ++ | 2.7 | 0.5 | Acid sphingomyelinase | Schuchman et al., 1991 |
| S1-15 | − | + | ++ | ++ | +++ | 2.3; 1.9 | 0.2 | α2-chimerin | Hall et al., 1993 |
| S1-28 | − | ++ | +++ | +++ | +++ | >20 | 0.2 | None | |
| S2-2 | − | + | ++ | ++ | ++ | 2.0 | 0.5 | None | |
| S2-6/ S2-7 | − | + | ++ | +++ | +++ | 2.0 | 1.4 | LIM Family | Sadler et al., 1992 |

− = Not detectable on dot-blot.

Group II: Clones expressed in fetal HDF and yHDF, but overexpressed in SHDF and WS HDF.

This group consists of 6 clones, five of which encode known proteins including fibronectin (FN) (Kornblihtt, et al. 1983), osteonectin (SPARC) (Swaroop, et al. 1988), two translation factors: eukaryotic initiation factor-2β (eIF-2β) (Pathak, et al. 1988) and elongation factor-1α (EF-1α) (Uetsuki, et al. 1989) and protein associated with low tumor metastatic potential nm23 (Steeg, et al. 1988). FN and SPARC were previously isolated as overexpressed clones from the unsubtracted WS cDNA library (Murano, et al. 1991). Therefore it is evident, that not all FN gene sequences were removed completely by our subtraction procedure. The S1-4 cDNA clone shows no identity or homology to known sequences.

Group III: Clones not expressed in fetal HDF but expressed in yHDF, sHDF and WS HDF.

This group contains 12 clones which are specific for postnatal HDF. Four of them: S1-18, S1-19, S1-21 and S2-4, represent the gene sequence for human pregnancy-specific β-1 glycoprotein known also as carcinoembryonic antigen SG5 (Rooney, et al. 1988). S1-14 has a 91% similarity but only 36% identity to human glutaminyl-tRNA synthetase subtraction protocol, among the 31 isolated clones, 15 of them were overexpressed in senescent and WS HDF, compared to early passage HDF, e.g., S1-3 which is the subject of the instant invention.

In contrast to the first unsubtracted WS cDNA library, the sW8 library consisted mainly of clones representing transcripts of very low abundance for both nuclear and cytoplasmic proteins, e.g., S1-3, the subject of this invention. As will be demonstrated below, S1-3 contains "zinc finger" domains which may play an important regulatory role in cell proliferation and DNA synthesis.

C. Characterization of Clone S1-3 mRNA Overexpressed in Normal Senescent and WS HDF The following studies were performed on S1-3 to more fully understand the structure and function of clone S1-3.

(1) S1-3 DNA Sequence Analysis

The originally isolated S1-3 clone was sequenced and shown to contain a 1.2 kb CDNA insert (See FIGS. 2A, 2B, and 2C; 1161 nucleotides, 224 amino acids). FIGS. 2A, 2B and 2C shows the nucleotide and deduced amino acid sequence of the largest insert obtained for S1-3. The nucleotides and amino acids are numbered in relation to the first nucleotide of the clone. As is evident, S1-3 insert is 1161 nucleotides in length and encodes for 224 amino acids (nucleotides 2 through 673 of SEQ ID NO:1).

Figure 3A:
FIG. 3A is a schematic diagram of S1-3 cDNA sequence and its putative protein. Dotted line represents the missing 5' fragment; Open box—a putative open reading frame; Solid boxes—three "zinc finger" domains; Shadowed box—putative transactivation domain.

The CDNA insert (FIGS. 2A, 2B and 2C) corresponding to S1-3 was sequenced by computer analysis using GenBank/EMBL databases. Sequence analysis of the entire original clone revealed a 224 amino-acid putative protein with three "zinc finger" domains that fit the consensus: C—$X_{2\text{-}4}$—C—$X_{12}$—H—$X_{35}$—H (Klug, et al. 1987) with a coiled-coil hydrophobic structure between them, which can serve as a transactivation domain (Inoue, et al. 1993; Ptashne, 1988). See shadowed box in FIG. 3A representing the transactivation domain with the coiled-coil structure as observed between the zinc finger domains (transactivation domain corresponds to amino acids 221 to 391 of FIG. 2 (SEQ ID NO:2).

Zinc finger domain #1 consists of nucleotides 50 to 133 of SEQ ID NO:1. These nucleotides code for the amino acid sequence of SEQ ID NO. 3.

SEQ ID NO:3
V F R C D K C T F T C S S D E S L Q Q H I E K H N E L K

Zinc finger domain #2 consists of nucleotides 134 to 220 of SEQ ID NO:1. These nucleotides code for the amino acid sequence of SEQ ID NO:4.

SEQ ID NO:4
P Y K C Q L C Y Y E T K H T E E L D S H L R N E H K V S R

Zinc finger domain #3 consists of nucleotides 392 to 475 of SEQ ID NO:1. These nucleotides code for the amino acid sequence of SEQ ID NO:5.

SEQ ID NO:5
R F P C E F C G R A F S Q G S E W E R H V L R H G M A L.

The $C_2H_2$ type of "zinc finger" domain is present in many transcription factors which plays a role in cell growth and differentiation, e.g., transcription factor Sp1 (Kadonaga, et al. 1987), Wilms' tumor protein (Call, et al. 1990), early growth response genes EGR1 and EGR2 (Sukhatme, et al. 1988; Joseph, et al. 1988), as well as *D. melanogaster*'s hunchback (Tautz, et al. 1987) and Kruppel-like murine and chicken homologs (Chowdhury, et al. 1988; Benn, et al. 1991), proteins with the highest homologies to S1-3 (FIG. 3B). FIG. 3B (a), (b) and (c) represent zinc finger domains #1, #2 and #3, respectively. Thus, it was established that clone S1-3 codes for a "zinc finger" protein with homologies to known "zinc finger" transcription factors (Klug, et al. 1987).

Due to the very low abundance of S1-3 cognate transcripts, which is also reflected by the low abundance of these cDNA clones in the library, it was found that conventional screening of the cDNA library would be ineffective and laborious in attempting to obtain the full length CDNA for S1-3. Therefore PCR analysis of the λZAP II unsubtracted CDNA library was performed to isolate the missing fragments representing the 5' end of the S1-3. This procedure was successfully used in isolating the full-length, very low frequency, c-myb CDNA clone (Amaravadi, et al. 1990). Briefly, subpools of λZAP II library were screened in phage form using PCR amplification, with one primer (right) specific for the 5' end of the cDNA and the second (left) non-specific primer corresponding to a vector sequence. Positive pools were detected by Southern analysis of PCR products followed by dilution and screening again by the same method until single clones were isolated. As opposed to conventional methods, this method allows screening of a larger number of clones and simultaneously identifies pools that contain clones with the longest cDNA inserts.

Primers specific for the analyzed clones and the corresponding vector primers were designed. To avoid nonspecific PCR amplification, each pair of primers had the same melting temperature ($T_m$), length and GC content, and no homologies on their 3' ends to other known sequences as established by searching Genbank/EMBL databases.

First, $1.5\times10^6$ clones which were divided into 30 subpools containing 50,000 pfu (plaque forming units) were screened. PCR amplification of each subpool was followed by DNA agarose gel electrophoresis and Southern analysis. Positive pools containing the PCR product of appropriate length were diluted to 10 subpools of 500 pfu each, and the amplification reaction was performed again followed by Southern analysis. Positive pools were plated at 100 pfu/plate and screened by the conventional method of plaque hybridization.

For S1-3 clone, of specific interest were the subpools which contained fragments of approximately 0.6 and 1.6 kb in length corresponding to the missing 5' ends of the two recognized transcripts, 1.8 and 2.8 kb respectively. However, no such subpools were found. PCR analysis and screening of subpools by colony hybridization technique revealed that the majority of S1-3 clones present in this WS cDNA library had the same length as the originally isolated clone. This was confirmed by DNA sequencing analysis. Minor bands with a size larger than 200 nucleotides, the fragment size expected to be generated from the original, partial clone, were also detected in some subpools, but due to their low abundance they were lost in subsequent dilutions and amplifications. This suggests that a very strong secondary structure exists at the 5' end of the S1-3 transcript and prevented cDNA synthesis beyond this point during construction of the WS cDNA library. Taking this into consideration, the 5' Rapid Amplification of cDNA Ends, "15' RACE method" (provided by Gibco BRL) was chosen as an alternate strategy for isolation of full length S1-3 clone. As a template for a specific reverse transcription step, poly($A^+$)RNA from senescent normal and WS HDF was used.

Figure 4:
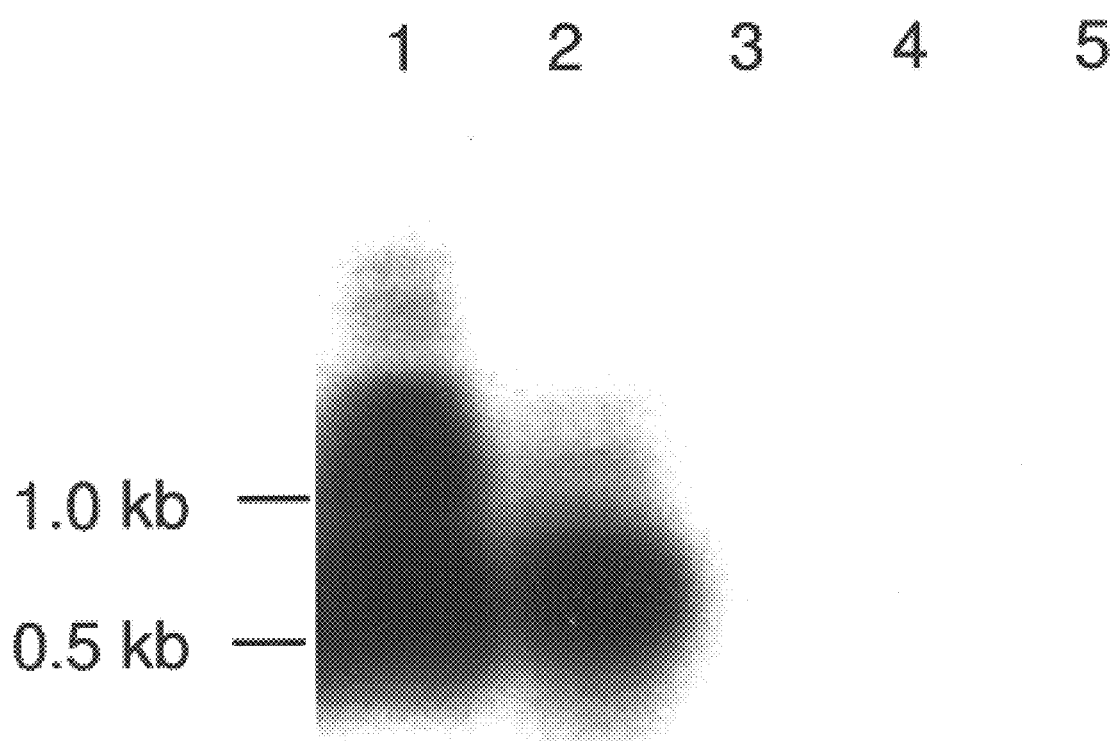
FIG. 4 is a photograph of a Southern gel showing DNA fragments generated by 5' PACE method. PCR amplified DNA fragments corresponding to the 5' end of S1-3 mRNA transcript were transferred to the filter and probed by $^{32}$p labeled S1-3 cDNA insert originally isolated from subtracted library. As a template polyA$^+$ RNA from senescent A25 and WS8 HDF was used (lanes 1 and 2, respectively). As controls the same reaction was performed in the absence of template (lane 3) and absence of one of the two required primers (lanes 4 and 5).

As shown in FIG. 4, fragments close in size to those expected (0.6 and 1.6 kb) were generated and reconstruction of the full length S1-3 cDNA by ligating those fragments into the originally isolated partial-length clone is currently in progress. See Section 6 "Sequencing the Full Length S1-3 Protein" on page 78.

(2) S1-3 Northern Analysis

All known clones in Group I were carefully examined by Northern analysis, for transcript size and their relative expression levels in yHDF, sHDF and WS HDF. For the majority of these clones, abundance levels of mRNA were relatively low such that our initial Northern analysis performed on total RNA (10 μg) and poly$A^+$RNA (1 μg) failed to reveal distinct bands. Therefore, Northern analysis was repeated using 3 μg of poly$A^+$RNA obtained from larger expansions of these cell cultures. Poly$A^+$RNA was isolated with the FastTrack kit (Invitrogen), which yielded high quality MRNA at approximately 1% of total RNA. Relative differences in expression in young and senescent cells was observed with four different cDNA clones (S1-3, S1-4, S1-15 and S2-6). See FIGS. 5 and 6.

Figure 5:
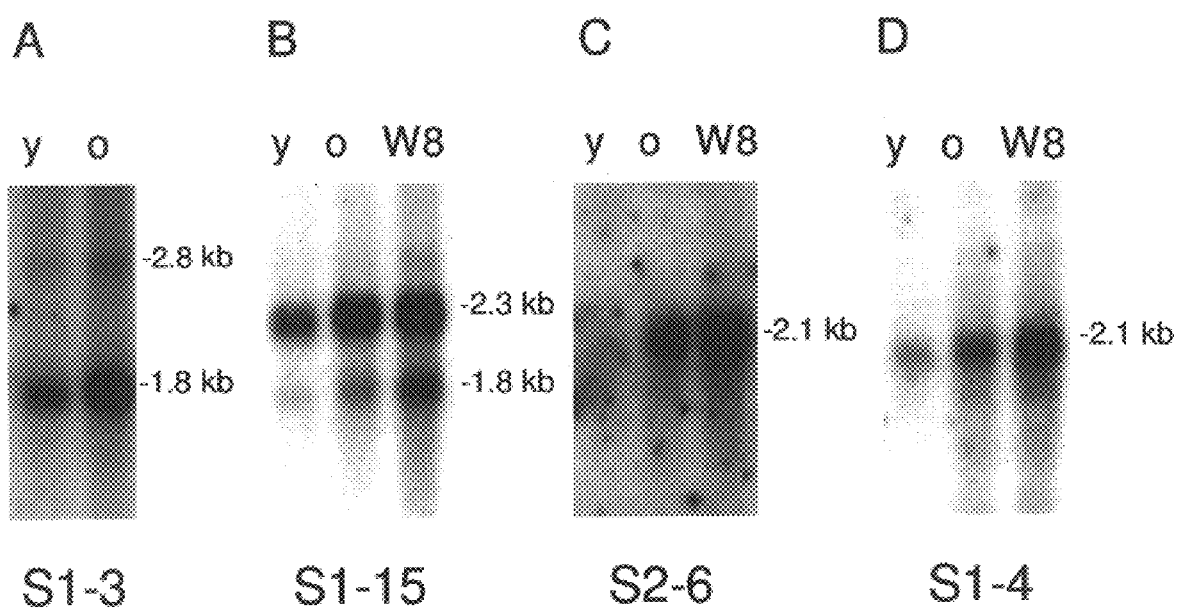
FIG. 5 is a photograph of a Northern gel showing RNA expression in four different cDNA clones. Panel A:clone S1-3; B:clone S1-15; C:clone S2-6; and D:clone S1-4. Each contained 3 $\mu$g of polyA$^+$ RNA. "y"—early passage A25 skin HDF at MPD 15; "o"—late passage A25 cells at MPD 44; "W8"—Werner syndrome (WS8) skin DF at MPD 12. PolyA$^+$ RNA equality of loading and evenness of transfer to ZETA Probe nylon membranes were assessed by control hybridization with 32p end-labeled oligo-dT probe.

FIG. 5 is a photograph of a Northern gel showing RNA expression in four different cDNA clones. Panel A: Clone S1-3; Panel B: Clone S1-15; Panel C: Clone S2-6; and Panel D: Clone S1-4. Each contained 3 μg of poly$A^+$RNA. "y": early passage A25 skin HDF at MPD 15; "o": late passage A25 cells at MPD 44; W8: Werner syndrome (WS8) skin DF at MPD 12. Poly$A^+$RNA equality of loading and evenness of transfer to ZETA Probe nylon membranes were assessed by control hybridization with $^{32}$p end-labeled oligo-dT probe.

Figure 6:
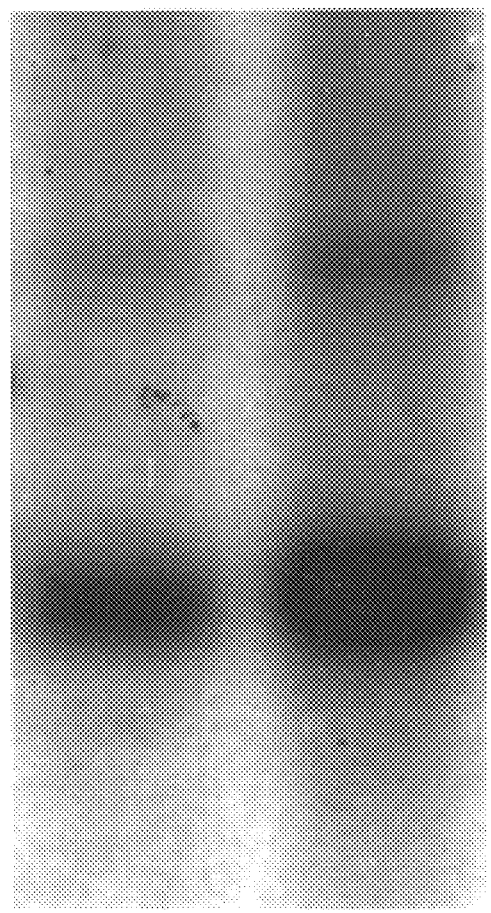
FIG. 6 is a photograph of a Northern gel showing S1- 3 mRNA expression in young (y) and old (o) senescent human fibroblast cells. Each lane contained 3 $\mu$g of polyA$^+$RNA, "y"-young, early passage A25 human skin fibroblasts; "o"-old, late passage A25 human skin fibroblasts. PolyA$^+$ RNA equality of loading and evenness of transfer to ZETA Probe nylon membrane were assessed by control hybridization with $^{32}$p end-labeled oligo-dT probe.

FIG. 6 is a photograph of a Northern gel showing clone S1-3 mRNA expression in young (y) and old (o) senescent human fibroblast cells. Each lane contained 3 μg of polyA+ RNA, "y"-young, early passage A25 human skin fibroblasts; "o"-old, late passage A25 human skin fibroblasts. PolyA+ RNA equality of loading and evenness of transfer to ZETA Probe nylon membrane were assessed by control hybridization with $^{32}$p end-labeled oligo-dT probe.

These Northern analyses demonstrated that the S1-3 1.2 kb cDNA insert hybridized to two transcripts, a prominent band at 1.8 kb and a less abundant transcript at 2.8 kb (FIG. 5A, FIG. 6). Also, these data show that both bands, 1.8 kb and 2.8 kb, are overexpressed in sHDF.

Preliminary experiments showed that S1-3 RNA expression is not changed under quiescent (arrested) conditions of cell growth such as serum depletion or contact inhibition. However, due to the very low abundance of S1-3 transcript this data must be confirmed using a more sensitive a s say such as quantitative RT-PCR.

(3) In vitro expression of S1-3 partial protein

Figure 7A:
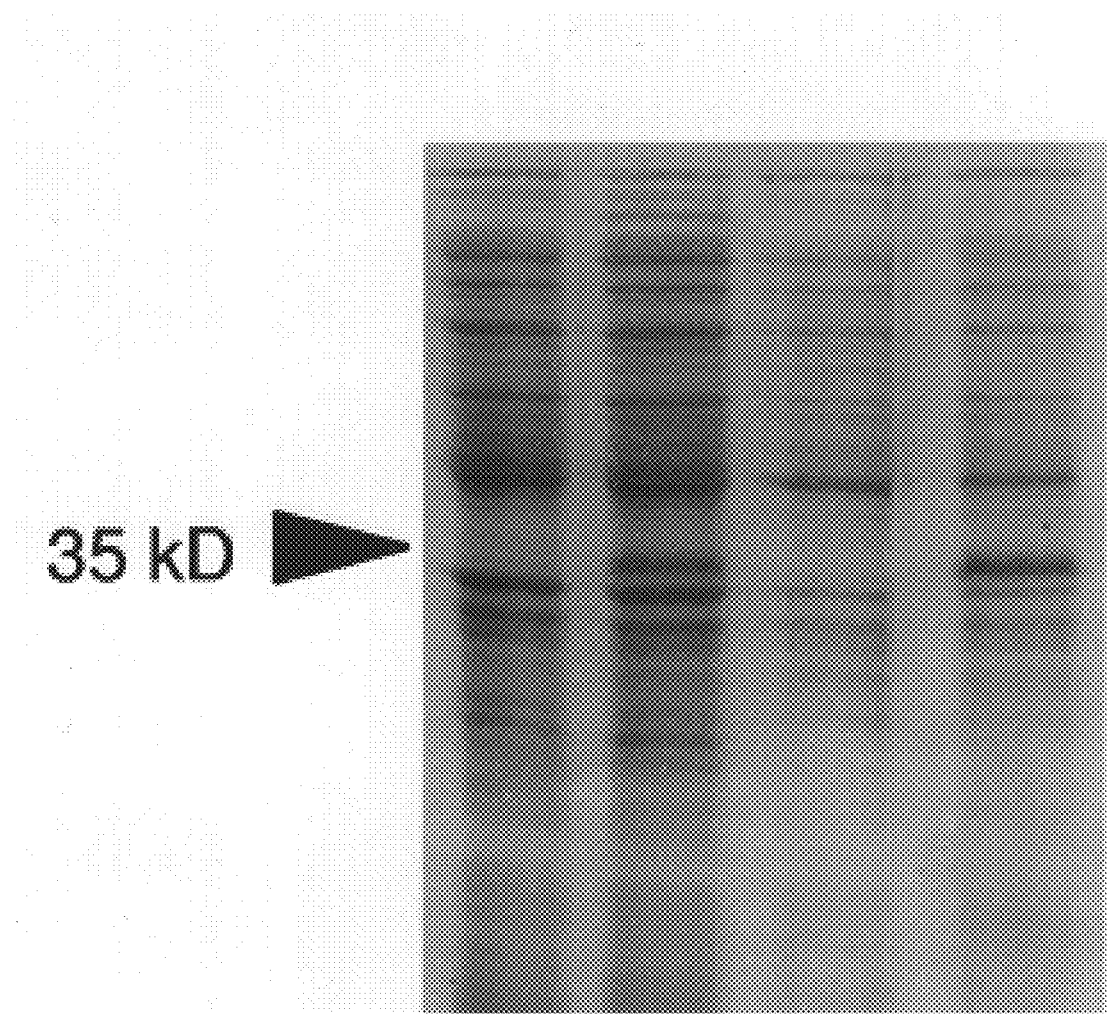
FIG. 7A is a photograph of a Coomassie stained SDSPAGE gel showing expression of S1-3 recombinant protein. BL21(DE3)plysS E.coli cells were transformed by S1 3/pET30a construct and grown at 24° C. to ODG50:0.6; induced by 1 mM IPTG in the presence or absence of rifampicin. Protein extracts were isolated 4hr later, analyzed on 10% SDS-PAGE and stained by Coomassie blue. Lane 1: uninduced cells; Lane 2: 1 mM IPTG; Lane 3: uninduced cells+20 $\mu$g/ml rifampicin; Lane 4: 1 mM IPTG+20 $\mu$g/ml rifampicin.

In order to characterize the nucleic acid binding properties of this protein, a partial S1-3 CDNA clone coding for the majority of its putative amino acid sequence, that includes three "zinc finger" domains and its transactivating domain, was expressed as a fusion protein in *E. coli* pET30 system (Novagen). In this system, the target gene was placed under the control of strong bacteriophage T7 transcription and translation signals and on induction yields the desired peptide in large quantities. The short oligohistidine (His-Tag) stretch on the N-terminus of the fusion protein binds to divalent cations allowing one step affinity purification on Ni-bound agarose. S1-3 cDNA insert was cloned into the multicloning region, downstream of the T7 promoter sequence, AUG transcription initiation codon and His-Tag coding sequence. DNA sequencing analysis showed that the proper open reading frame (ORF) was correctly aligned in the S1-3/pET30 construct. Chimeric protein was expressed in BL21(DE3)pLysS *E. coli* strain after IPTG induction of the lacUV5 promoter that controls the expression of T7 polymerase, the enzyme responsible for the expression of fusion protein. The preliminary results showed that the new protein (approximately 35 kD Mg) was produced after induction of T7 polymerase-dependent transcription (FIG. 7A). The MW of the new protein is roughly consistent with the expected 30 kD comprising the His/S1-3 fusion protein. Since expression was not very efficient (S1-3 protein consisted of approximately 20% of total proteins), conditions for optimal induction of expression for large scale production of this protein were tested. It was observed that *E. coli* cultivation at room temperature and the presence of rifampicin (inhibitor of the # subunit of *E. coli* RNA polymerase, but not T7 polymerase) during induction increased the relative abundance of S1-3 protein production to 70% of total bacterial proteins (FIG. 7A).

Figure 7B:
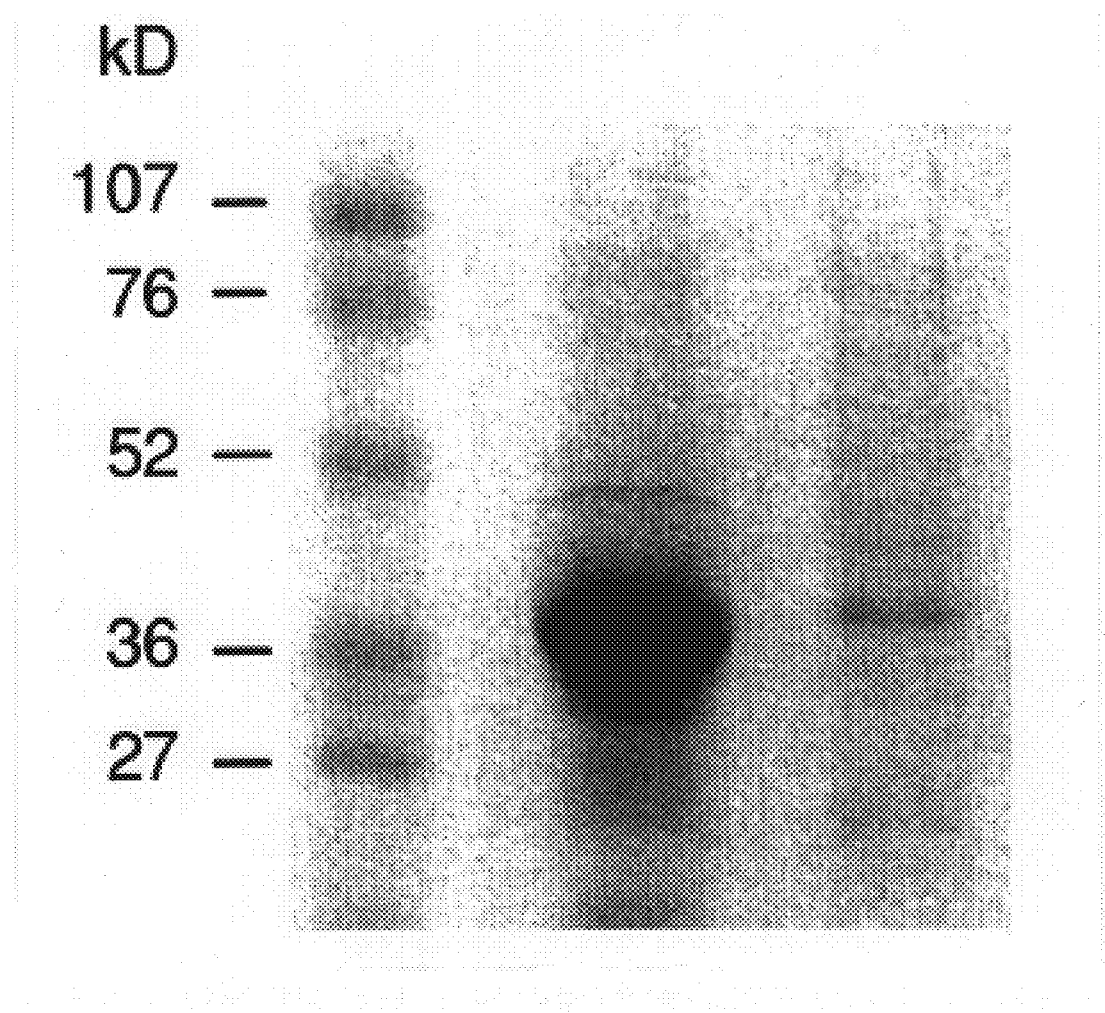
FIG. 7B is a photograph of a Coomassie stained SDSPAGE gel showing expression S1-3/pET30a protein on a large scale. Lanes "S"—MW standard; "I"—cells induced for 4hr with 1 mM IPTG in the presence of 20 $\mu$g/ml rifampicin; "U" uninduced cells.

This protein has been expressed on a large scale (FIG. 7B) and an appropriate amount has been isolated (6 mg) for production of polyclonal antisera in rabbits and for experiments to characterize the nucleic acid binding properties of S1-3 protein as described below.

(4) Specificity of S1-3 protein binding to DNA

In order to test that S1-3 protein can function as a DNA binding protein and to characterize its DNA binding site, pilot experiments (described below) were performed revealing that:

1. in vitro expressed S1-3 protein carries DNA binding activity which depends on the presence of divalent cations such as $Zn^{2+}$;

2. a degenerative oligonucleotide library, which was used to determine the DNA binding site, contained sequences that are specifically bound by S1-3 protein; and 3. the binding selection methods based on consecutive rounds of binding a pool of random oligonucleotides to immobilized S1-3, protein followed by DNA amplification was chosen appropriately and is working.

(a) Construction of a degenerative oligonucleotide library

A library of degenerative oligonucleotides was constructed according to Morris, et al. (Morris, et al. 1994). Such a library was used for determination of a DNA consensus sequence for MZF1, a member of the $C_2H_2$ "zinc finger" protein family, that plays a central role in regulation of hematopoiesis. A 45-mer oligonucleotide library that contained a 14-base random sequence flanked by EcoRI and BamHI linkers (FIG. 8) was synthesized by the Molecular Biology Core facility in the Department of Biochemistry and Molecular Biology at University of Arkansas Medical Sciences. Two primers were also synthesized, one complementary to the 3' linker and the other identical to the 5' linker. The synthetic template and 3' primer were radiolabelled with T4 polynucleotide kinase and [γ-$^{32}$P]ATP and used in a primer extension reaction with Ven polymerase (New England Biolabs). Gel purified double-stranded radioactively labeled DNA molecules were used to test S1-3 protein-DNA binding activity in electrophoretic mobility shift assay and in the functional selection of S1-3 protein DNA binding site.

(b) Electrophoretic Mobility Shift Assay

Figure 9:
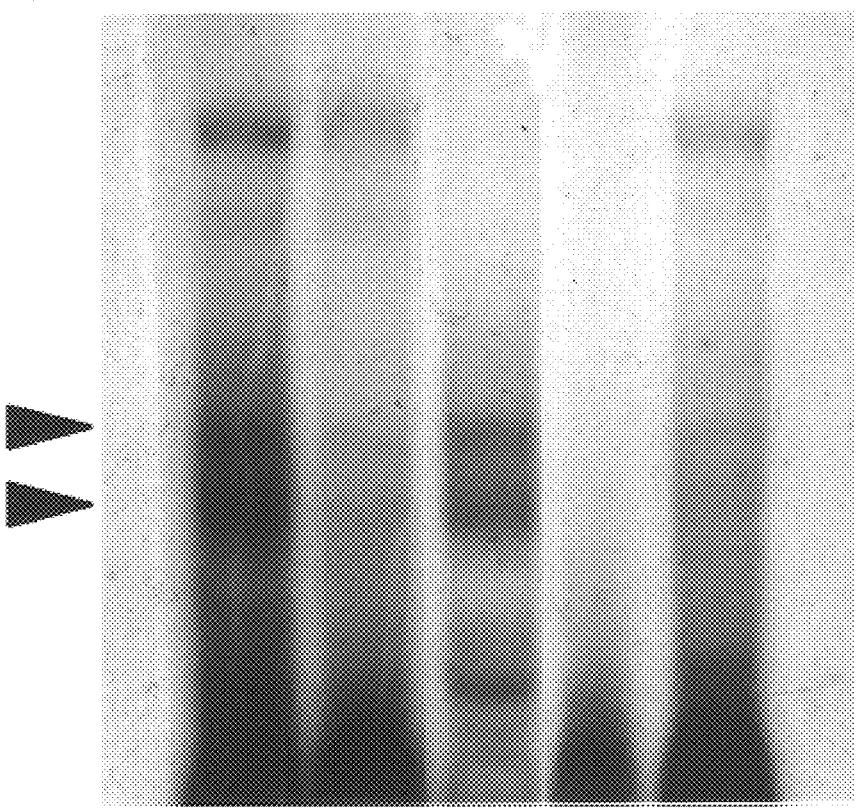
FIG. 9 is a photograph of an acrylamide gel showing the results from an electrophoretic mobility shift assay (EMSA). Concentrations of recombinant S1-3 protein, random synthetic oligonucleotides and EDTA present in analyzed binding reactions are shown above lanes. Solid arrows indicate retarded DNA bands that contain protein/DNA complexes.

To test DNA binding activity of in vitro expressed S1-3 protein in the electrophoretic mobility shift assay, several sets of binding reactions that contained various amounts of S1-3 protein and DNA were prepared. Each reaction was carried out in "zinc finger" (ZF) Binding Buffer (25 mM HEPES pH 7.5, 50 mM KCl, 0.01 mM $ZnSO_4$, 1mM DTT, 0.1 Tween 20 and 5% glycerol). After one hour of equilibration, one set of reactions was treated with 50 mM EDTA and all the reactions were analyzed on a 5% native acrylamide gel (50:1 acrylamide to bisacrylamide ratio) in TBE electrophoresis buffer. Autoradiography of the dried gel revealed the existence of two retarded DNA bands and their intensity strongly depended on the concentration of S1-3 protein present in the reaction. In the sample where protein/DNA complexes were subjected to EDTA chelating activity, a significant reduction in the DNA amounts in shifted bands were observed (FIG. 9). Therefore, one can conclude that S1-3 protein was capable of binding to DNA and this reaction was $Zn^{2+}$+dependent.

(c) Selection of Consensus Sequence

The S1-3 protein affinity column was prepared to select DNA molecules specific for binding to S1-3 protein from the random pool of synthesized double-stranded oligonucleotide library. One mg of purified S1-3 protein in 0.1 M sodium phosphate buffer (pH 7.5) was coupled to 1.2 ml agarose using AminoLink coupling gel according to the manufacturer's instructions (Pierce Chemical Co.). The AminoLink agarose is activated to form aldehydes that form Shiff's bases with primary amines of the protein. Under the applied pH conditions, it is expected that mainly N-terminal amino acids would be engaged in reductive amination with sodium cyanoborohydride added during the coupling procedure and would result in stable covalent linkage of the protein to the agarose support. The efficiency of coupling was 80% (20% of applied protein was detected in the filtrate and wash as determined by Bradford protein determination). After protein coupling, the column was washed with 2M sodium chloride to remove free protein molecules that could form oligomers with linked protein. Finally, the affinity column was washed with ZF Binding Buffer and stored at 4° C. For the initial selection of binding sites, 3 μg of randomized radiolabelled double-stranded DNA was applied to the affinity column in zinc containing buffer. This amount of DNA represents $6 \times 10^{13}$ molecules of synthetic 45-mer which is 23,000-fold more than the possible combinations of 4 bases at 14 positions in the randomized part of the template ($4^{14} = 2.7 \times 10^8$). The calculated number of DNA molecules with the same nucleotide sequence is equivalent to 0.05% of the total DNA amount used in the experiment allowing detection by liquid scintillation counting of DNA molecules specifically retained by the immobilized protein.

Figure 10A:
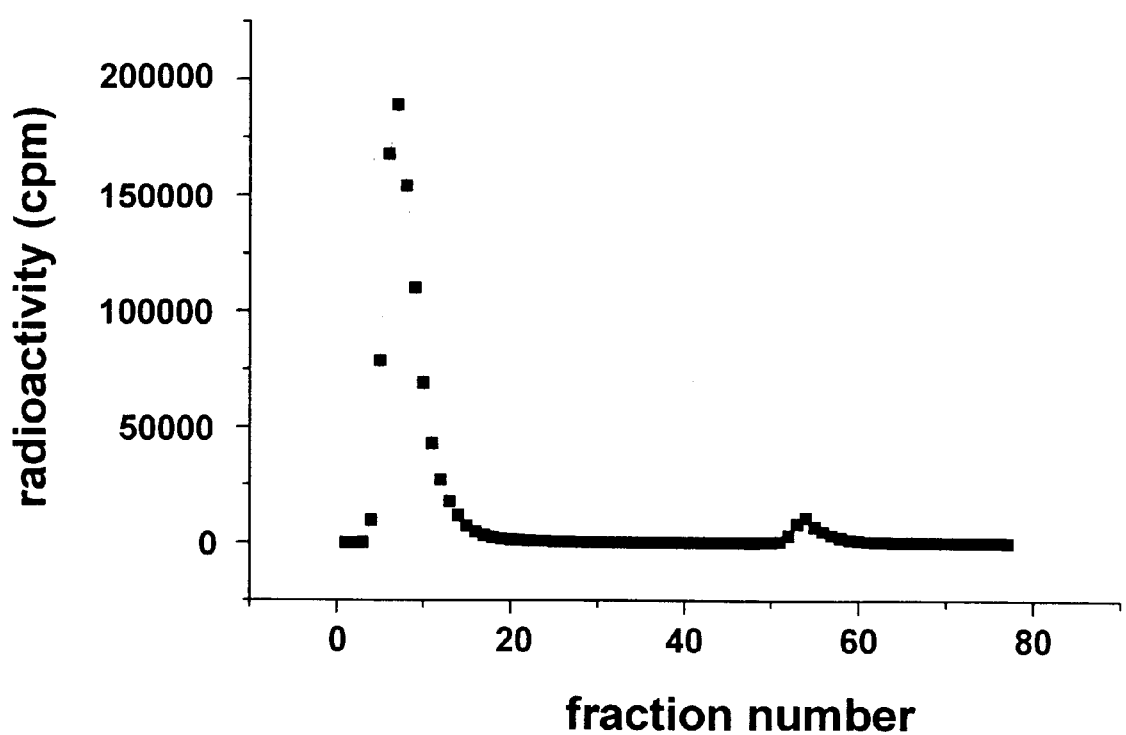
FIG. 10A is a graph showing S1-3 affinity chromatography of random synthetic DNA oligonucleotides for the initial round of S1-3 DNA binding site selection. Fractions 1–45 contain unbound radioactive DNA found in the wash. Fractions 46–77 contain DNA molecules specifically retained by immobilization S1-3 protein and recovered in the elution step with buffer containing 50 mM EDTA and 1 M NaCl.
Figure 10B:
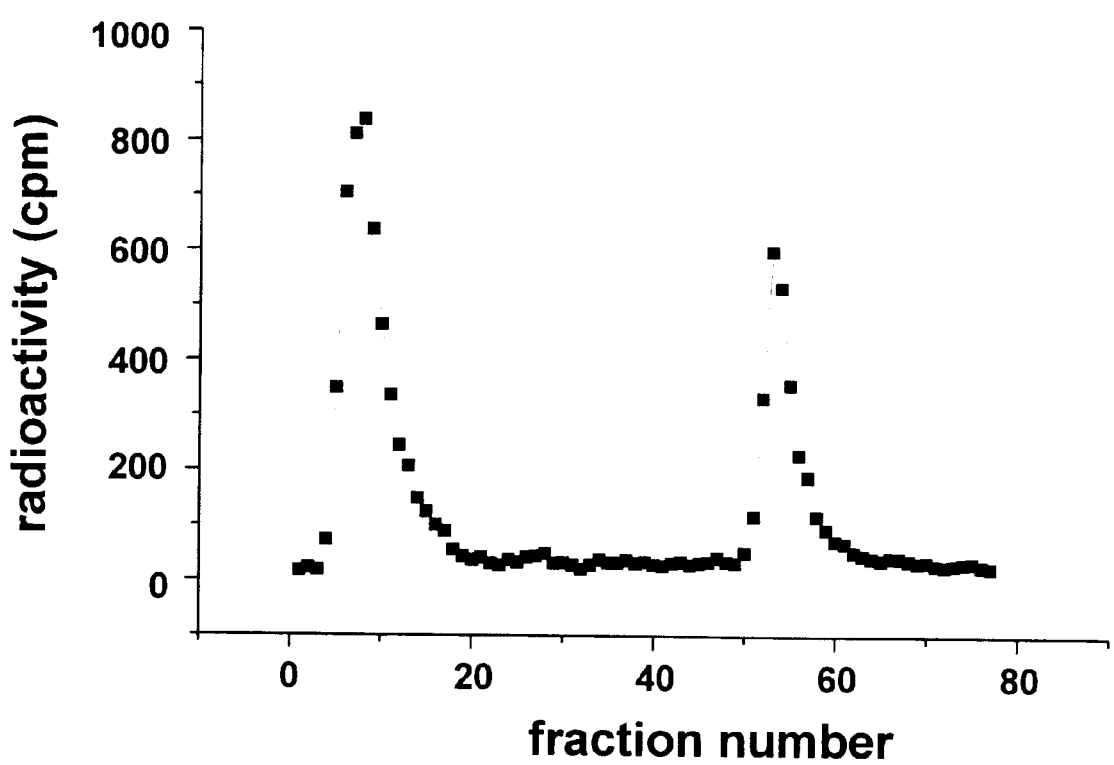
FIG. 10B is a graph showing S1-3 affinity chromatography of DNA molecules specifically retained in the initial round of S1-3 binding site selection. Fractions 1–45 contain unbound DNA molecules and fractions 46–77 contain DNA retained by the column.

Following one hour of incubation at room temperature the column was washed with 5 void volumes of ZF Binding Buffer to elute unbound DNA molecules. In doing so, essentially all unbound DNA was removed from the column since no radioactivity was detected in the last fractions of the wash. DNA molecules specifically retained by the column were eluted with ZF Binding Buffer supplemented with 50 mM EDTA and 1 M NaCl. Approximately 2% of the total amount of radioactively labeled DNA was found in eluted fractions (FIG. 10A). Such high DNA recovery could indicate either nonspecific binding to agarose beads or a short DNA recognition site for S1-3 protein. To answer this question, eluted fractions containing recovered DNA molecules were pooled and applied to the affinity column without additional labeling or PCR amplification. It was assumed that nonspecific binding would result in the same percentage of DNA retained by the column as in the first chromatography, while specific protein/DNA interactions should result in retention of a significant fraction of applied DNA. Under the same fractionation conditions 50% of the applied DNA molecules were found in EDTA/NaCl eluted fractions (FIG. 10B). This result indicates that S1-3 protein specifically selected oligonucleotide sequences in the first round of selection and that probably only a small number of bases are required to form the protein/DNA complex(es).

(5) Determination of consensus sequence for S1-3 binding

To further understand the structure and function of S1-3 protein zinc finger protein, the DNA consensus sequence specific for binding S1-3 protein was identified using an affinity selection of DNA sequences from a library of synthetic random oligonucleotides.

For this study, the protocol described in Section 4 (a) below on page 71 entitled "Determination of Consensus Sequences for S1-3 Binding" was followed. A population of random DNA sequences which specifically bound to S1-3 was enriched by four rounds of affinity selection. After the fourth round of selection, no further enrichment was observed in the fraction specifically bound to S1-3 protein. Selected oligonucleotides were cloned into pUC 118 plasmid and their sequences were analyzed for the presence of common DNA motifs. Initially, 27 DNA sequences were aligned using the Pileup program resident in the Wisconsin Sequences Analysis Package. An alignment was then refined manually. The analyzed DNA sequences fell into four categories: Group I with a consensus: Pu G A T G Py; Group II with a consensus: Pu G A T A Py; Group III with a consensus: A T A G; and Group IV with a consensus: which included those DNA molecules that contained partial consensus sequences found in Groups I, II, and III. See FIG. 11 which is a comparison of the aligned S1-3 DNA binding site consensus sequence Groups I, II, III, and IV observed in different clones. Lower case letters indicate nucleotides that belong nucleotides that belong to linkers. Bold characters in Group IV indicate conserved bases. These alignments only showed perfect homologies along a 4 base pair stretch. Statistical occupance of a tetranucleotide was compared ($4^4$—bases randomized at four positions) that should be found in the 27 DNA sequences (total number of bases was 440) with the experimental occupance of consensus tetranucleotides. A random tetranucleotide should be statistically found 1.7 times in the analyzed sequences, whereas GATG (Group I) was found 9 times, GATA (Group II) occurred 7 times and ATAG (Group III) was found 4 times. The above comparison indicated non-random distribution of analyzed tetranucleotides. Isolated sequences were specifically selected by three "zinc finger" domains present in S1-3 protein. Based on this preliminary data, the following consensus sequence has been identified which is specific for S1-3 DNA binding site:

GATRRWWG where "R" represents a purine and where "W" represents either an adenine or thymidine. At least 60 additional DNA sequences will be identified in order to confirm the accuracy of above predicted consensus sequence (G A T R R W W G).

Homologies of S1-3 DNA binding consensus sequence to known regulatory regions for transcription and DNA replication were analyzed (FIG. 12). FIG. 12 shows a comparison of S1-3 DNA binding site consensus sequences to various origins of replication and DNA binding sites for transcription factors. The presence of the following two S1-3 consensus sequences, G A T A G A T G and G A T G A T A G, were identified in different origins of DNA replication included those derived from ColA, *R. meliloti, C. crescentus, S. pombe*, Monkey ORS 24, Monkey ORS8, Hum ARS1. Significant sequence homology to DNA binding sites for several known transcription factors was also found. S1-3 consensus binding sites overlap a number of defined DNA binding sites for major transcription factors (GATA-1, NF-E1, AP1 and E2A) that have established function in cell proliferation and differentiation. These data, together with results from the microinjection of antisense RNA (see next paragraph), suggest that S1-3 protein is an inhibitor of cell growth either as a regulator of DNA replication or as a regulator (by competition for the same binding site) of transcriptional activity of other transcription factors.

(6) Role S1-3 Plays in Inhibition of DNA Synthesis— Assay for Inhibition of DNA Synthesis This study was designed to determine the role S1-3 gene played in inhibition of DNA synthesis and/or cell growth. This was accomplished by microinjection of in vitro-synthesized antisense RNAs into young HDF and assessment of the level of DNA synthesis.

The protocol for assaying inhibition of DNA synthesis is as follows. Clones were selected based on their possible role in inhibition of DNA synthesis. Since clones isolated from the subtracted library contained only a partial sequence of their corresponding transcript, an indirect assay, e.g., microinjection of antisense RNA, was used to evaluate its possible effect on DNA synthesis. Thus, genes having a role in the inhibition of DNA synthesis would be expected to stimulate DNA synthesis. Based on the inventor's previous experience with other clones which appeared to stimulate DNA synthesis despite its overexpression in senescent and quiescent cells, the inventor performed parallel experiments to monitor inhibition of DNA synthesis after microinjection of antisense RNA. This study would indicate a stimulatory role of the cognate gene.

For this study, A25 normal skin HDFs approaching the end of their in vitro lifespan as measured by accumulated population doublings (56 from MPD$_{max}$=58, [$^3$H]-thymidine labeling index in the presence of 15% fetal bovine serum less than 15%), were grown in medium without serum for 5 days before microinjection. Thymidine labeling index at this time was less than 5t. Cells were microinjected with approximately 6000 copies of antisense RNA. Each sense RNA, hydrolyzed antisense RNA and water served as negative controls. Immediately after microinjection [$^3$H]-thymidine was added to the medium. In the assay for stimulation of DNA synthesis, cells remained in the conditioned serum-free medium, while in the assay for inhibition of DNA synthesis, cells were refed with medium supplemented with 15% FBS. Twenty four hours after microinjection cells were fixed and the number of labeled nuclei was counted in injected and noninjected cells.

In repeated experiments, S1-3 partial antisense mRNA showed stimulation of DNA synthesis after microinjection of antisense RNA, suggesting its possible function as an inhibitor of DNA synthesis (Table 3). As seen in Table 3, antisense and sense S1-3 MRNA were synthesized and capped in vitro using cDNA from partial S1-3 clone as a template. A25 skin fibroblast at the end of their replicative lifespan were incubated for 5 days in Minimal Essential Medium (MEM) in the absence of Fetal Bovine Serum (FBS) and microinjected with approximately 6000 molecules of RNA per cell, [$^3$H]thymidine was added to the medium, and incubation continued for 24 hrs; the cells were then fixed and stained, and the percentage of radiolabelled nuclei determined. As a negative control, cells were microinjected with pure water.

The results demonstrated that antisense RNA for clone S1-3 stimulated DNA synthesis approximately three fold in injected cells, when compared to uninjected cells. Moreover, by comparing the numbers of labeled nuclei present in the adjacent area to injected squares with those from a distant area, it was concluded that none of these clones had a paracrine effect on neighboring cells. Thus, S1-3 antisense RNAs did not inhibit DNA synthesis after refeeding injected cells by 15% FBS suggesting that neither has a role in stimulation of DNA synthesis. Surprisingly, partial-length sense RNA for clone S1-3 also stimulated DNA synthesis to the same extent as antisense RNA. One explanation for the data is that this is a dominant-negative effect of the partial peptide which can code for the "zinc finger" domain but lacks the transactivating domain, and therefore can suppress the action of full-length S1-3 protein by occupying a specific S1-3 DNA binding site.

Thus, these data for the indirect functional assay, e.g., microinjection of antisense RNA, have shown that S1-3 is probably involved in the inhibition of DNA synthesis.

TABLE 3

EFFECT OF S1-3 mRNA MICROINJECTION
ON DNA SYNTHESIS IN SENESCENT HUMAN FIBROBLASTS

| RNA | Exp. No. | % labeled nuclei (no. of cells scored) | | Relative Stimulation |
|---|---|---|---|---|
| | | injected | uninjected | |
| antisense | 1. | 13.3 (88) | 4.9 (81) | 2.7 |
| | 2. | 7.4 (107) | 3.4 (87) | 2.2 |
| | 3. | 8.9 (123) | 2.9 (103) | 4.5 |
| | 4. | 8.5 (211) | 2.0 (151) | 4.3 |
| sense | 5. | 21.4 (112) | 4.0 (100) | 5.4 |
| | 6. | 8.3 (167) | 3.6 (140) | 2.3 |
| | 7. | 10.9 (137) | 3.6 (140) | 2.2 |
| water | 8. | 2.4 (85) | 2.1 (95) | 1.1 |

The role S1-3 gene plays in inhibition of DNA synthesis and/or cell growth will also be studied by transfection of young HDFs with an expression vector containing cDNA under the control of a strong constitutive promoter, such as the human cytomegalovirus promoter (CMV) followed by determination of the level of DNA synthesis in an assay for transient expression, and evaluation of colony formation and in vitro replicative lifespan as determined by Mean Population Doublings (MPD) in stable transformants.

3. SUMMARY

The phenotype of replicative senescence is a dominant trait in human diploid fibroblasts (HDF). Therefore, overexpressed and/or newly expressed causal genes were identified by constructing and screening a subtracted CDNA library derived from polyA$^+$RNA of prematurely senescent Werner syndrome (WS) HDF. Many different cDNA clones were identified that are overexpressed in senescent and WS HDF. Among them are six known sequences coding for: acid sphingomyelinase, fibronectin, SPARC, nm23-metastasis suppressor protein, and two translation factors, eIF-2β and EF-1a. Among the unknown clones is S1-3, which encodes a protein containing "zinc finger" domains, suggesting nucleic acid binding properties. The other identified clones do not have significant homology to known sequences. Steady-state mRNA levels of S1-3 are elevated in both WS and senescent normal HDF when compared to young HDF, which suggests that senescent and WS HDF enter a final common pathway where multiple gene overexpression may generate diverse antiproliferative mechanisms and pathogenic sequences.

4. CONCLUSIONS

Replicative senescence of human diploid fibroblasts (HDF) is a dominant trait, which predicts that overexpressed and/or newly expressed mRNAs, encoding negative growth regulatory functions, will be present in senescent compared to early-passage vigorously growing ("young") cells. The analysis of clones isolated from a subtracted WS cDNA library led to the identification of a novel cDNA, S1-3 that codes for a "zinc finger" transcription factor. DNA sequence analysis of clone S1-3 cDNA revealed that its 1.2 kb insert codes for a novel protein with three C$_2$H$_2$ type "zinc finger" domains. These zinc finger domains fit the consensus for those "zinc finger" domains present in many DNA binding proteins, for example, transcription factor SPI (Kadonaga, et al. 1987), Wilms' tumor protein (Call, et al. 1990), early growth response genes EGR1 and EGR2 (Joseph, et al. 1988; Sukhatme, et al. 1988), and some differentiation factors such as D, melanogaster hunchback protein (Tautz, et al. 1987), hematopoietic MZF1 (Morris, et al. 1994) and kidney Kid-1 (Witzgall, et al. 1993) proteins.

The above data clearly demonstrated that S1-3 MRNA is overexpressed in senescent cells and codes for zinc-binding protein whose structure and homology to known proteins suggest a regulatory role in gene expression. More importantly, preliminary data suggest it plays a role in inhibition of DNA synthesis, the characteristic inevitably manifested in in vitro senescence.

Further Characterization of S1-3 and Its Zinc Finger Protein

Several experiments are outlined below that are specifically designed to further study the structure and function of the S1-3 protein zinc finger protein.

1. Kinetics of S1-3 Gene Expression Under Different Growth Conditions

To clarify whether the expression of S1-3 is dependent on other events in addition to those that are senescence-specific, steady-state levels of its RNAs under different growth conditions, as well as during the cell cycle, will be determined. Young, normal HDF will be inhibited in their growth and made quiescent in two different ways: (1) Logarithmically growing cells in medium supplemented with 15% fetal bovine serum (FBS) will be made quiescent by depletion of FBS to 0.5%. Total RNA will be isolated at different times after serum depletion as was previously described for S1-5 cDNA clone (Lecka-Czernik, et al. 1995); (2) RNA expression of cognate clones in yHDF inhibited by confluent density growth arrest will also be studied. For this purpose, cells will be grown to high density in the presence of 15% FBS and isolate RNA at confluence and at different time points (days) after confluence is achieved.

For examining gene expression under growth stimulatory conditions, quiescent cells, after 5 days of growth in the presence of 0.5% FBS, will be stimulated with medium containing 15% FBS and RNA samples will be collected at different time points (up to 48 hours) after stimulation. Cells made quiescent through contact inhibition will be related from growth arrest by subculturing to a lower density in the present of 15% FBS. RNA samples will be collected as above at different time points (days) after stimulation. In both experiments DNA synthesis by [3H]-thymidine incorporation into DNA will be monitored and analyzed.

RNA expression of clone S1-3 will be studied during the cell cycle. Cells will be synchronized by a double thymidine block which will arrest them at the G1/S border (Lew, et al. 1991). Cells will be released from the block by refeeding with medium containing no thymidine. Progression through the cell cycle will be measured by the fluorescence-activated cell sorting (FACS) technique and RNA will be isolated every 3 hours after release. Additionally, transition through different phases in the cell cycle will be monitored by Northern analysis to determine the expression of two reference mRNAs (cyclin E and cyclin B1) whose expression is regulated by the cell cycle. Cyclin E MRNA is expressed in late G1 and disappears by late S phase (Lew, et al. 1991), whereas cyclin B1 mRNA is expressed in S phase and no longer seen in M (Pines, et al. 1989; Gyuris, et al. 1993).

Due to the low abundance of transcripts to be studied and the high costs of growing large amounts of cells for polyA+ RNA isolation, RNA samples collected in the above experiments will be analyzed by competitive quantitative RTPCR which is several orders of magnitude more sensitive than traditional Northern blotting and RNase protection techniques (Wang, et al. 1989; Quantitative RT-PCR 1993). Based on sequence data for S1-3 cDNA clone, primers will be designed at a distance of approximately 200–500 nucleotide apart to minimize the difficulties associated with PCR amplification of longer DNA fragments. A region will also be selected, as determined from its cDNA sequence, that does not form strong secondary structures (e.g. palindromic structures) nor consists of a high GC content, and stretches of continuous guanine or cytosine bases will be avoided; these factors can drastically diminish dramatically efficiency of the PCR reaction. To correct for tube-to-tube variations in amplification efficiency, exogenously added internal amplification standard differing slightly in size (approximately 50 nucleotides) from the target sequence will be used, which will enable us to distinguish between the amplified (target and standard) sequences (Wang, et al. 1989). Thus, competitive PCR experiments can be performed where both target and standard sequences are amplified from the same primers to minimize differences in the amplification efficiencies of these sequences. Another advantage of using an exogenous standard instead of an endogenous MRNA, e.g. β-actin, as a standard, is that one can manipulate its concentration in the reaction mixture to obtain concentrations closer to those of the target sequence, thereby minimizing the possibility of interference with amplification of target RNA. Reactions will also be run with and without reverse transcriptase to control for amplification of residual contaminating DNA.

2. Determination of Protein Level and Location: Polyclonal Antibody Production To Determine Location and Level of Protein Expression To characterize the cognate S1-3 protein in yHDF and sHDF, polyclonal antibodies will be produced in rabbits using as antigen a fusion protein expressed in the E. coli pET30 system (Novagen). Thus, polyclonal antibodies will be produced against S1-3 to compare levels of protein expression and cellular location in young and senescent HDF. Previously, a similar system (pET19) was used by the inventor to express WS3-10 protein from a CDNA clone isolated from the unsubtracted WS CDNA library (Grigoriev, et al. 1995 (in press)) followed by protein purification and production of specific WS3-10 polyclonal antibodies in rabbits. Polyclonal antibodies used in Western blotting, immunoprecipitation of $^{35}$S-methionine-labeled proteins (Grigoriev, et al. 1994) and immunocytochemistry (Grigoriev, et al. 1995 (in press)) will enable the quantification and localization of the S1-3 protein in cells, to examine their level in young versus old cells, and to detect the amount of cognate proteins under different growth conditions such as inhibition by serum depletion and stimulation by serum repletion. These will be used to detect possible post-translational modifications by comparing the electrophoretic mobility of the cognate cellular protein from old and young cells with that translated in rabbit reticulocyte lysates (Lecka-Czernik, et al. 1995).

3. Additional Microinjection/Functional Analyses of S1-3

As discussed above, microinjection experiments were performed and antisense RNAs were used to eliminate complementary transcripts of S1-3 overexpressed in senescent HDF. To confirm the inhibitory effect of S1-3 on DNA synthesis and cell growth, "short-term" and "long-term" functional assays will be performed. In the short term assay, in vitro synthesized full-length sense mRNA will be microinjected into fetal HDF (HSC172 strain) that do not express mRNA corresponding to S1-3. Cells will be made quiescent by incubation for five days in medium without fetal bovine serum (FBS), and then injected with approximately 6000 MRNA copies, a standard range used to effect overexpression. Microinjected cells will be refed after injection with fresh medium containing 15% FBS plus $^3$H-thymidine. Twenty four hours after microinjection and exposure to $^3$H-thymidine, cells will be fixed and DNA synthesis determined by scoring labeled nuclei in injected versus uninjected cells (Liu, et al. 1994; Lecka-Czernik, et al. 1995). As negative controls, cells will be microinjected with (1) water, (2) hydrolyzed RNA and (3) full length neutral transcript, such as WS3-10, which is known from previous experiments not to have an effect on DNA synthesis (Goldstein, et al. 1989).

DNA synthesis as reflected by [$^3$H]-thymidine uptake will be studied in cells transfected with the episomal mammalian expression vector pCEP4 (Invitrogen) where expression of the S1-3 cDNA is under the control of a constitutive CMV enhancer-promoter (for the immediate-early gene of the human cytomegalovirus) providing a high-level of protein expression. As a control for DNA synthesis, [$^3$H]thymidine uptake will be monitored and analyzed in cells transfected with "empty" (without cDNA insert) vector.

Cells will be transfected by electroporation which is routinely used and usually yields approximately 40% transfection efficiency. The efficiency of transfection in each experiment will be estimated by cotransfection with pCEP4 vector containing a cDNA insert coding for β-galactosidase. β-galactosidase production will be monitored by cytochemical analysis, using Galacto-Light™ (TROPIX, Inc.) a chemiluminescent detection method, an easy and extremely sensitive assay enabling detection of 2 fg to 20 ng of β-galactosidase. Measurements of β-galactosidase activities in transfectants will be standardized by comparing the level of endogenous enzyme in non-transfected cell extracts from young and old HDF. Light output generated by cleavage of Galacton™ chemiluminescent substrate by β-galactosidase will be quantitatively measured using a luminometer.

In the "long term" assay, by selection to hygromycin resistance, colonies with stable integrants will be isolated to reveal the effects of continuous overexpression of these cDNA clones on DNA synthesis and cell growth in yHDF. If S1-3 has an immediate effect on inhibition of DNA synthesis, then one can expect difficulties in obtaining stable transfectants, which will be reflected by a significant difference in yields of stable transfectants with or without insert. In the case of a delayed inhibitory effect (e.g. an effect on cell proliferation) one can expect a similar number of stable transformants but their rate of cell proliferation and lifespan as determined by Mean Population Doublings (MPD) will be reduced in cells transfected with cDNA clone S1-3 in contrast to those transfected with "empty" plasmid. A parallel experiment will be done where the cDNA sequences will be introduced in antisense direction. In this case one can expect the adverse effect. If these genes have a role in restricting MPDs one can expect an increase in the $MPD_{max}$ of these stable transfectants.

To determine whether the isolated stable transfectants express the RNA and protein of interest, a recently developed method where cognate protein is expressed as a fusion with green fluorescent protein (GFP) will be utilized. GFP is under the control of the cytomegalovirus promoter (CMV) and neomycin is a selection marker for stable transfectants (Clontech). GFP protein expression will be identified in situ upon UV or blue light activation of GFP chromophore which generates green fluorescent light (Chalfie, et al. 1994). This method allows easy and direct detection of colonies expressing the transfected protein. As an additional functional assay, senescent HDF cells will be microinjected with polyclonal antibodies raised against S1-3 protein. Appropriate preimmune globulins will serve as controls. With this assay, the activity of each cognate protein may be blocked and the subsequent effect on DNA synthesis will be monitored and analyzed.

4. Assessment of S1-3 Protein DNA Binding Properties

To understand the function and biological relevance of a new transcription factor it is critical to identify the target DNA-binding site. Analysis of the crystal structure of the "zinc finger" proteins with their cognate DNA-binding sites revealed that "zinc finger" domains recognize a 3nucleotide sequence present on either one or both strands in the major groove of the DNA helix. Currently, the specific DNA consensus binding sites have been determined for few members of the "zinc finger" protein family and these never exceed 9 nucleotides (Morris, et al. 1994; Letovsky, et al. 1989; Christy, et al. 1989; Rauscher, et al.; Kinzler, et al. 1990).

a. Determination of Consensus Sequence for S1-3 Binding

Figure 14:
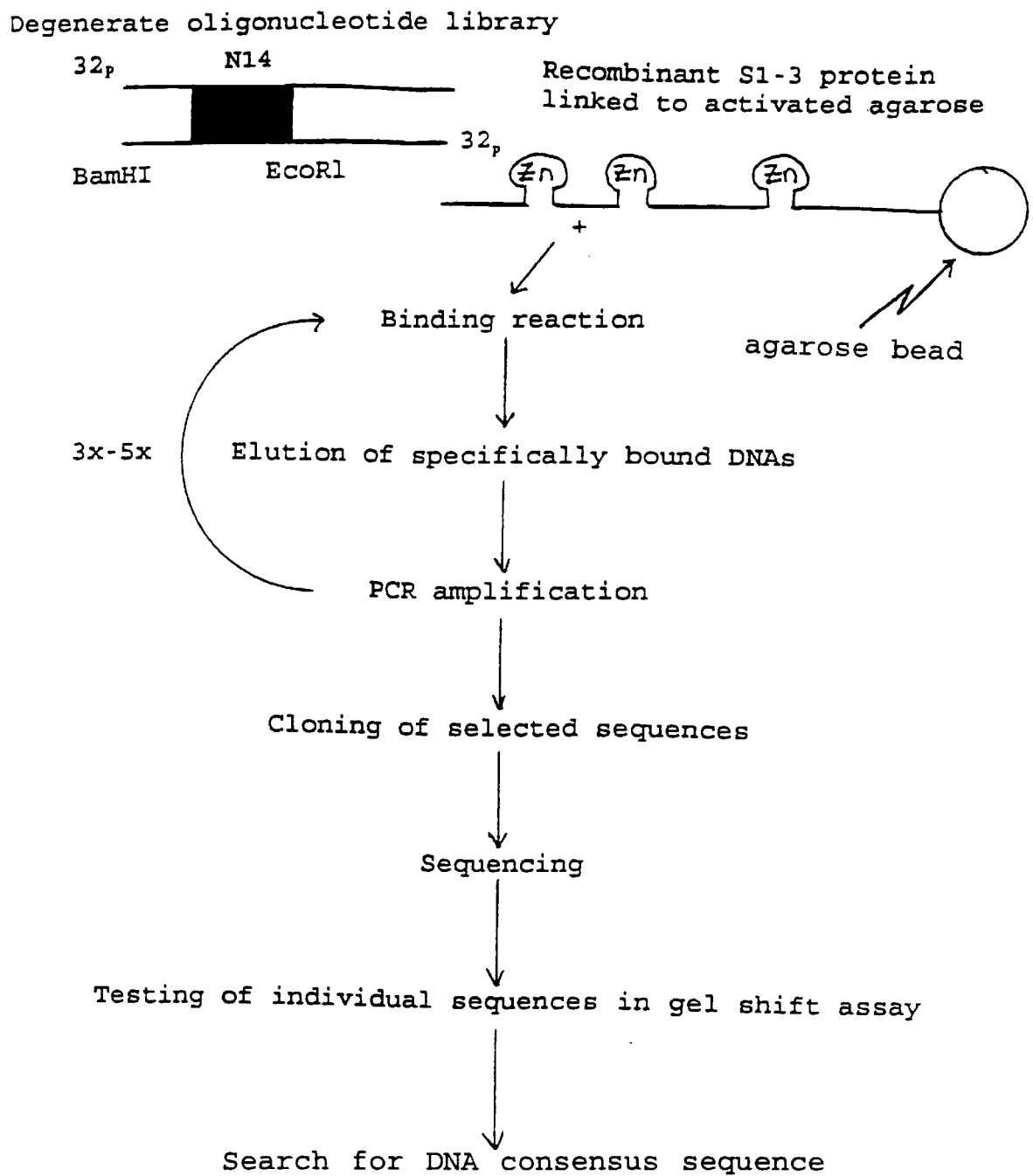
FIG. 14 is an outline of scheme representing experimental design for isolation of S1-3 DNA binding sequences.

Studies on the characterization of the DNA/binding consensus sequence specific for S1-3 protein will be continued. As presented above, four rounds of binding and PCR amplification were performed to enrich a pool of specifically bound sequences. The number of analyzed sequences should be increased to confirm the correctness of derived consensus and will accumulate further data from at least 60 additional DNA sequences to have a statistically relevant number of analyzed DNA molecules. A consensus binding site for S1-3 protein will be determined using University of Wisconsin Genetics Computer Group's (GCG) DNA sequence analysis programs running locally on a VAX. The experimental protocol is shown below in FIG. 14.

Determination of binding affinity by the apparent equilibrium dissociation constants Using an electrophoretic mobility shift assay (EMSA), the equilibrium dissociation constant ($K_D$) will be determined describing binding affinity of S1-3 protein to the selected consensus DNA sequences. The apparent equilibrium dissociation constant ($K_D$) will be determined for selected oligonucleotides and in vitro-synthesized consensus sequence using the electrophoretic mobility shift assay— EMSA (Morris, et al. 1994; Czernik, et al. 1994; Ausubel, et al. 1993). This comparison will enable the selection of sequences with the highest binding affinities. A limiting amount of DNA will be titrated with various concentrations of S1-3 protein and DNA-protein complexes will be analyzed by native polyacrylamide gel electrophoresis. The $K_D$ value, equal to the concentration of the analyzed protein required to bind half of the available DNA (Riggs, et al. 1970; Hurlburt, et al. 1992), will be determined by quantitative densitometric analysis of the autoradiograms and will be considered as the $K_D$ as described in Czernik, et al. 1994.

5. Assessment of S1-3 Protein as a Transcription Factor

Experiments presented below will define the function of S1-3 as a transcription factor and will lead to the isolation of "downstream" gene sequences regulated by it.

a. Searching for genomic elements interacting with S1-3 protein

To study S1-3 as a transcription factor, genomic elements that interact with S1-3 protein will be identified and characterized. Genes which may be regulated by the S1-3 protein will be studied by searching for homologies between established S1-3 DNA-binding sequence and sequences in DNA computer databases known to bind transcription factors. DNA will also be isolated from a genomic library of DNA ("cisacting") fragments which specifically bind to S1-3 ("transacting") protein and their role as transcription regulatory elements will be studied using a luciferase promoter/enhancer reporter system. This system will also be used to look for differences in regulation of transcription between young and senescent HDF.

Thus, more specifically, the Genbank/EMBL databases will be searched for homologies of established consensus and selected sequences with the highest $K_D$ values to DNA sequences known to bind transcription factors. The natural DNA sequences that specifically bind the S1-3 protein will also be studied. Human genomic DNA will be digested into small fragments and linkers harboring specific primer sequences to enable PCR will be ligated to their ends. DNA fragments which will specifically bind S1-3 protein will be selected using methods described above. Selected fragments will be cloned, sequenced, and S1-3 protein binding affinity determined.

Those selected sequences with the highest binding affinity will be analyzed for their potential to function as transcriptional regulatory elements using the luciferase promoter-enhancer reporter system (GeneLight™, Promega). With different types of GeneLight plasmids, each carrying the coding region for firefly (*Photinus pyralis*) luciferase which is used to monitor transcriptional activity in transfected eucaryotic cells, selected DNA fragments will be examined for their possible function as a promoter, enhancer or attenuator of transcription. Isolated genomic sequences with S1-3 protein binding affinity will be introduced into different types of GeneLight plasmids, and the luciferase activity in transfected young and senescent fibroblasts will be determined by a specific assay (Promega). This assay is 100 times more sensitive than the CAT assay and is very suitable, especially for weak promoters. Sequences regulated differently in sHDF versus yHDF will be identified and studied (this system has been used to study the enolase gene enhancer region (Taylor, et al. 1995).

b. Isolation of "Downstream" Gene Sequences Regulated by S1-3 Protein

Gene sequences regulated by S1-3 protein will be isolated by comparing the pool of transcripts from cells induced to express S1-3 protein with the pool of transcripts from uninduced cells. Once S1-3 protein is identified as a potential transcription factor and genomic DNA sequences specifically interacting with this protein are isolated, experiments leading to the isolation of "downstream" genes regulated by S1-3 protein will be performed. Depending on the role of genomic regulatory elements (promoter/enhancers or attenuators, determined in above experiments) routes described below will be pursued.

In general, the pool of RNA transcripts isolated from cells forced to overexpress S1-3 protein will be compared with the pool of transcripts isolated from uninduced cells which represent the basal level of naturally occurring messages. S1-3 cDNA will be cloned into the LacSwitch Inducible Mammalian Expression System (provided by Stratagene), where transcription of the inserted gene sequence is blocked by binding of Lac-repressor protein to Lac-operator sequences located upstream of the inserted gene. Transcription and expression of S1-3 protein will be triggered by IPTG which decreases binding affinity of the Lac-repressor protein to operator sequences. The LacSwitch System seems to be especially useful for induction of a gene sequence whose transcript is expressed at a very low level and its tight regulation is extremely important. This experiment will use HSC172 cells which lack S1-3 expression. Transfected fibroblasts will be selected by their hygromycin and G418 resistance. The fraction of transformants able to express S1-3 protein after IPTG induction will be determined by immunocytochemistry using polyclonal antibodies against S1-3 protein. Two pools of poly($A^+$) RNA will be isolated: (1) from transfected cells induced by IPTG to express S1-3 protein, and (2) from the same uninduced cells. One pool will serve as a template for construction of a cDNA library, the other will be used for subtraction of this library to isolate cDNA sequences which are regulated by S1-3 protein, the procedure previously utilized for construction of the subtracted WS CDNA library (Lecka-Czernik, et al. 1995 (in press)). Should the data obtained from the luciferase assay described above indicate that S1-3 functions as a positive regulator of transcription, a library from induced cells will be constructed and subtracted with poly($A^+$)RNA from uninduced cells. Additionally, the library will be subtracted with in vitro transcribed RNA for S1-3 gene sequence to avoid isolation of the corresponding cDNA clones. If S1-3 is expected to be a negative regulator of gene expression, the cDNA library will be constructed from the uninduced pool of poly($A^+$)RNA and subtracted with an induced pool. Isolation of cDNA clones specifically regulated by S1-3 protein will be followed by their structural analysis.

6. Sequencing the Full Length S1-3 Protein

As shown in FIG. 4 and discussed above, fragments close in size to the expected sizes (0.6 kb and 1.6 kb) have been generated and reconstruction of the 5' end of S1-3 to obtain full length S1-3 cDNA is in progress by ligating those fragments into the originally isolated partial-length 1.2 kb clone.

This reconstruction will include producing the 5' missing end of the 1.2 kb clone by using the 5' Rapid Amplification of cDNA Ends method (the 5' RACE method, commercially available from Gibco/BRL). Briefly, the 5' RACE system is a set of prequalified reagents intended for synthesis of first strand cDNA for subsequent PCR amplification. The method is based on the rapid amplification of cDNA Ends and anchored PCR methods and is suitable for the amplification of rare messages for which little sequence information is available. The 5' RACE system provides a rapid and reliable solution to a technically complex procedure.

The 5' RACE System involves the following: first strand cDNA is synthesized from total or poly($A$)$^+$RNA using a gene-specific primer (GSP1) that the user provides and SuperScripts II, an RNase H derivative of Moloney murine leukemia virus reverse transcriptase (M-MLV RT). After first strand cDNA synthesis, the original MRNA template is destroyed with RNase H, which is specific for RNA:DNA heteroduplex molecules. Unincorporated dNTPs, GSP1, and proteins are separated with cDNA using a GlassMAX® spin cartridge. An anchor sequence is then added to the 3' end of the cDNA using TdT and dCTP. Since the tailing reaction is performed in a PCR-compatible buffer, the entire contents of the reaction may be directly amplified by PCR without intermediate organic extractions, ethanol precipitations, or dilutions. PCR amplification is accomplished using Taq DNA polymerase (Perkin-Elmer), a user-designed, nested gene-specific, primer (GSP2) that anneals to a site located within the CDNA molecule, and a novel deoxyinosine-containing anchor primer (patent pending) provided with the system.

Following amplification, 5' RACE products can be cloned into an appropriate vector for subsequent characterization procedures, which may include sequencing, restriction mapping, preparation of probes to detect the genomic elements associated with the cDNA of interest, or in vitro RNA synthesis.

For obtaining the full length S1-3 clone the following steps will be performed:

(1) Fragments produced by the 5' RACE method as described above will be ligated to the commercially available pGEMT vector which is specifically designed for ligation of PCR products. This protocol does not require blunt or cohesive ends.

(2) Clones containing S1-3 fragments will be identified by employing the well known technique of colony hybridization.

(3) The isolated positive clones identified by the colony hybridization protocol (Step 2 above) will then be examined for their size by restriction analysis using restriction enzymes, e.g., PstI and SphI. The clones will next be sequenced.

(4) The newly identified S1-3 fragments will then be ligated into the originally isolated S1-3 clone (using known blunt end ligation techniques) and correctness of the open reading frame will be determined.

Other embodiments are within the following claims.

REFERENCES

The following references may facilitate the understanding or practice of certain aspects and/or embodiments of this invention. Inclusion of a reference is this list is not intended to and does not constitute an admission that the reference represents prior art with respect to the present invention.

REFERENCES

Amaravadi, L. and King, M. W.; A rapid and efficient nonradioactive method for screening recombinant DNA libraries. *Biotechniques*, 16:98–103 (1990).

Arber, S., Halder, G., and Caroni, P.; Muscle LIM protein, a novel essential regulator of myogenesis, promotes myogenic differentiation. *Cell*, 79:221–231.

Argaves, W. S., Tran, Hl, Burgess, W. H., and Dickerson, K.; Fibulin is an extracellular matrix and plasma glycoprotein with repeated domain structure. *J. Cell Biol.*, 111:31553164 (1990).

Ausubel, F. M., Brent, R., Kingston, R. E., Moore, D. D., Seidman, J. A., Smith, J. A., and Struhl, K., eds. DNA protein interactions. In: *Current Protocols in Molecular Biology, Vol. II*, Greene Publishing Associates and John Wiley and Sones (1993).

Benn, A., Antoine, M., Beug, H., and Niessing, J.; Primary structure and expression of a chicken cDNA encoding a protein with zinc-finger motifs. *Gene*, 106:207–212 (1991). Bernard, O., Ganiatsas, S., Kannourakis, G., and Dringen, R.; Kiz-1, a protein with LIM zinc finger and kinase domains, is expressed mainly in neurons. *Cell Growth Differ.*, 5:1159–1171 (1994).

Bevilacqua, G., Sobel, M. E., Liotta, L. A., and Steeg, P. S.; Association of low nm23 RNA levels in human primary inflitrating ductal breast carcinomas with lymph node involvement and other histopathological indicators of high mestatic potential. *Cancer Res.*, 49:5185–5190 (1989).

Call, K. M., Glaser, T., Ito, C. Y., Buckler, A. J., Pelletier, J., Haber, D. A., Rose, E. A., Kral, A., Yeger, H., Lewis, W. H., Jones, C., and Housman, D. E.; Isolation and characterization of a zinc finger polypeptide gene at the human chromosome 11 Wilms' tumor locus. *Cell*, 60:509–520 (1990).

Chalfie, M., Tu, Y., Euskirchen, G., Ward, W. W., and Prasher, D. C.; Green fluorescent protein as a marker for gene expression. *Science*, 263:802–805 (1994).

Chomczynski, P. and Sacchi, N.; Single-step method of RNA isolation by acid guanidinium thiocyanate-phenolchloroform extraction. *Anal. Biochem.*, 162:156–159 (1987).

Chowdhury, K., Rohdewohld, H., and Gruss P.; Specific and ubiquitous expression of different Zn finger protein genes in the mouse. *Nucleic Acids Res.*, 16:9995–10011 (1988).

Christy, B. and Nathans, D.; DNA binding site of the growth factor-inducible protein Zif268. *Proc. Nat'l. Acad. Sci, U.S.A.*, 6:8737–8741 (1989).

Church, G. M. and Gilbert, W.; Genomic sequencing. *Proc. Natl. Acad. Sci. USA*, 81:1991–1995 (1984).

Cristofalo, V. J. and Pignolo, R. J.; Replicative senescence of human fibroblast-like cells in culture. *Physiol. Rev.*, 73:617–638 (1993).

Czernik P. J., Shin D. S. and Hurlburt B. K. Functional selection and characterization of DNA-binding sites for trp repressor of *E.coli J. Biol. Chem.* 269:27869–27875, 1994.

DeTata, V., Patasznik, A., and Cristofalo, V. J.; Effect of the tumor promoter phorbol 12-myristate 13-acetate (PMA) on proliferation of young and senescent W1-38 human diploid fibroblasts. Exp. Cell Res., 205:261-269 (1993).

Dice, F. J.; Cellular and molecular mechanisms of aging. *Physiol. Rev.*, 73:149–159 (1993).

Dimri, G. P. and Campisi, J.; Altered profile of transcription factor-binding activities in senescent human fibroblasts. *Exp. Cell Res.*, 212:132–140 (1994).

Dimri, G. P., Hara, E., and Campisi, J.; Regulation of two E2F-related genes in presenescent and senescent human fibroblasts. *J. Biol. Chem.*, 269:16180–16186 (1994).

Dje, K. J., Mazabraud, A., Viel, A. L., le Maire, M., Denis, H. I., Crawford, E., and Brown, D. D.; Three genes under different development control encode elongation factor 1-αin *Xenopus laevis. Nucleic Acid Res.*, 18:3489–3493 (1990).

Doolittle, R. F., Feng, D. F., and Johnson, M. S.; Computer based characterization of epidermal growth factor precursor. Nature, 307:558–560 (1984).

Duguid, J. R., Rohwer, R. G., and Seed, B.; Isolation of cDNAs of scrapic-modulated RNAs by subtractive hybridization of a cDNA library. *Proc. Natl. Acad. Sci. USA,* 85:5738–5742 (1988).

Dulic, V., Drullinger, L. F., Lees, E., Reed, S. I., and Stein, G. H.; Altered regulation of G1 cyclins in senescent human diploid fibroblasts: accumulation of inactive cyclin E-Cdk2 and cyclin D1-Cdk2 complexes. *Proc. Natl. Acad. Sci. USA* 90:11034–11038 (1993).

Dulic, V., Kaufmann, W. K., Wilson, S. J., Tisty, T. D., Lees, E., Harper, J. W., Elledge, S. J., and Reed, S. I.; p53dependent inhibition of cyclin-dependent kinase activities in human fibroblasts during radiation-induced G1 arrest. *Cell,* 76:1013–1023 (1994).

El-Deiry, W. S., Tokino, T., Velculescu, V. E., Levy, D. B., Parson, R., Trent, J. M., Lin, D., Mercer, W. E., Kinzler, K. W., and Vogelstein, B.; WAF1, a potential mediator of p53 tumor suppression. *Cell,* 75:817–825 (1993).

Epstein, C. J., Martin, G. M., Schultz, A. L., and Motulski, A. G.; Werner syndrome: A review of its symptomatology, natural history, pathologic features, genetics and relationship to the natural aging process. *Medicine,* 45:177–221 (1966).

Fett, R. and Knippers, R.; The primary structure of human glutaminyl-tRNA synthetase: a highly conserved core, amino acid repeat regions, and homologies with translation elongation factors. *J. Biol. Chem.,* 266:1448–1455 (1991).

Flemington, E. K., Speck, S. H., and Kaelin, W. G., Jr.; E2F-1-mediated transactivation is inhibited by complex formation with the retinoblastoma susceptibility gene product. *Proc. Natl. Acad. Sci. USA,* 90:6914–6918 (1993).

Freyd, G., Kim, S. K., and Horvitz, H. R.; Novel cysteine-rich motif and homeodomain in the product of the Caenorhabditis elegans cell linage gene lin-11. *Nature,* 344:876–879 (1990).

Funk, S. E. and Sage, H.; The $Ca^{2+}$-binding glycoprotein SPARC modulates cell cycle progression in boxing aortic endothelial cells. *Pro. Natl. Acad. Sci. USA,* 88:2648–2652 (1991).

Gilles, A. M., Presecan, E., Vonica, A., and Lascu, I.; Nucleoside diphosphate kinase from human erythrocytes. *J. Biol. Chem.,* 266:8784–8789 (1991).

Goldstein S.; The Biology of Aging, in Textbook of Internal Medicine, Section Editor, W. R. Hazzard. Editor-in-Chief, W. N. Kelly, J.B. Lippincott, Philadelphia, 2nd edition, pp. 2336–2342 (1992).

Goldstein S.; Replicative senescence: The human fibroblast comes of age. *Science,* 249:1129–1133 (1990).

Goldstein S.; Cellular senescence. In: Endocrinology, 2nd Ed., L. J. DeGroot, F. G. Cahill, Jr., W. D. Odell, L. Martini, J. T. Potts Jr., D. H. Nelson, E. Steinberger and A. I. Winegrad, eds. Grune and Stratton, New York, pp. 2525–2549 (1989).

Goldstein S. and Lin C. C.; Rescue of senescent human fibroblasts by hybridization with hamster cells in vitro. *Exp. Cell Res.* 70:436–439 (1971).

Goldtein, S.; Human genetic disorders which feature accelerated aging. In: *The Genetics of Aging*, E. L. Schneider, ed., Plenum Press, New York, pp. 171–224 (1978).

Goldstein, S., Murano, S., Benes, H., Moerman, E. J., Jones, R. A., Thweatt, R., Shmookler Reis, R. J., and Howard, B. H.; Studies on the molecular genetic basis of replicative senescence in Werner syndrome and normal fibroblasts. *Exp. Gerontol,* 24:461–468 (1989).

Goldstein, S., Moerman, E. J., Fujii, S., and Sobel, B. E.; Overexpression of plasminogen activator inhibitor type-1 in senescent fibroblasts from normal subjects and those with Werner syndrome. *J. Cell Physiol.*, in press (1994).

Goldstein, S., Moerman, E. J., and Baxter, R. C.; Accumulation of insulin-like growth factor binding protein-3 in conditioned medium of human fibroblasts increases with chronological age of donor and senescence in vitro. *J. Cell Physiol.,* 156:294–302 (1993).

Goto, J., Rubenstein, J., Weber, J., Woods, K., and Drayna, D.; Genetic linkage of Werner's syndrome to file markers on chromosome. 8. *Nature,* 355:735–738 (1992).

Grigoriev, V. G., Moerman, E. J., and Goldstein, S.; Overexpression of insulin-like growth factor binding protein-3 by senescent human fibroblasts: Attenuation of the mitogenic response to IGF-1. *Exp. Cell Biol.,* 219:315–321 (1995).

Grigoriev, V. G., Moerman, E. J., and Goldstein, S., Senescence and cell density of human diploid fibroblasts influence metabolism of insulin-like growth factor binding proteins. *J. Cell Physiol.* 160:203–211 (1994).

Grigoriev, V. G., Tweatt, R., Moerman, E. J., and Goldstein, S.; Expression of senescence-induced protein WS3-10 in vivo and in vitro. *Exp. Gerontol, in press* (1995).

Gyuris, J., Golemis, E., Chertkov, H., and Brent, R.; Cdil, a human G1 and S phase protein phosphatase that associates with Cdk2. *Cell,* 75:791–803 (1993).

Hall, C., Sin, W. C., Teo, M., Michel, P., Smith, P., Dong, J.M., Lim, H. H., Manser, E., Spurr, N. K., Jones, T. A., and Lim, L.; α2-chimerin, an SH2-containing GTYPase-activating protein for the ras-related protein p21$^{rac}$ derived by alternative splicing of the human n-chimerin gene, is selectively expressed in brain regions and testes. *Mol. Cell Biol.,* 13:4986–4998 (1993).

Hara, E., Yamaguchi, T., Nojima, H., Ide, T., Campisi, J., Okayama, H., and Oda, K.; Id-related genes encoding helix-loop-helix proteins are required for G$_1$ progression and are repressed in senescent human fibroblasts. *J. Biol. Chem.* 269:2139–2145 (1994).

Harley, C. V., and Goldstein, S.; Cultured human fibroblasts: Distribution of cell generations and a critical limit. *J. Cell. Physiol.,* 97:509–516 (1978).

Harper, J. W., Adami, G. R., Wei, N., Keyomarsi, K., and Elledge, S. J.; The p21 Cdk-interacting protein Cipl is a potent inhibitor of G1 cyclin-dependent kinases. *Cell,* 75:805–816 (1993).

Hayflick L.; The limited in vitro lifetime of human diploid cell strains. *Exp. Cell Res.,* 37:614–636 (1965).

Hirsch-Behnam, A., Delius, H., and de Villiers, E. M.; A comparative sequence analysis of two papillomavirus (HPV) types 2a and 57. *Virus Res.* 18:81–97 (1990).

Hunter T.; Braking the cycle. *Cell,* 75:839–841 (1993).

Hurlburt, B. K. and Yanofsky, C.; trp repressor/trp operator interaction. Equilibrium and kinetic analysis of complex formation and stability. *J. Biol. Chem.,* 267:16783–16789 (1992).

Inoue, S., Orimo, A., Hosoi, T., Kondo, S., Toyoshima, E., Kondo, T., Ikegami, A., Ouchi, Y, Orimo, H., and Maramatsu, M.; Genomic binding-site cloning reveals an estrogen-responsive gene that encodes a RING finger protein. *Proc. Natl. Acad. Sci.,* 90:11117–11121 (1993).

Jarvis, W. D., Kolesnick, R. N., Fornari, F. A., Traylor, R. S., Gerwirtz, D. A., and Grant, S.; Induction of apoptotic DNA damage and cell death by activation of the sphingomyelin pathway. *Proc. Natl. Acad. Sci. USA,* 91:73–77 (1994).

Jelinek, W. R. and Schmid, C. W.; Repetitive sequences in eukaryotic DNA and their expression. *Annu. Rev. Biochem.,* 51:813–844 (1982).

Joseph, L. J., Le Beau, M. M., Jamieson, Jr., G. A., Acharya, S., Shows, T. B., Rowley, J. D., and Sukhatme, V. P.; Molecular cloning, sequencing, and mapping of EGR2, a human early growth response gene encoding a protein with "zinc-binding finger" structure. *Proc. Nat'l. Acad. Sci., U.S. A.,* 85:7164–7168 (1988).

Kadonaga, J. T., Carner, K. R., Masiarz, F. R., and Tijan, R.; Isolation of CDNA encoding transcription factor Sp1 and functional analysis of the DNA binding domain. *Cell,* 51:1079–1090 (1987).

Kanzaki, T., Olofsson, A., Moren, A., Wernstedt, C., Hellman, U., Miyazono, K., Claesson-Welsh, L., and Heldin, C.; TGF-β1 binding protein: a component of the large latent complex of TGF-β1 with multiple repeat sequences. *Cell,* 61:1051–1061 (1990).

Karlsson, O., Thor, S., Norberg, T., Ohlsson, H., and Edlund, T.; Insli gene enhancer binding protein IS1-1 is a member of a novel class of proteins containing both homeo- and Cys-His domain. *Nature,* 344:879–882 (1990).

Kaziro, Y.; Replication sequences in eukaryotic DNA and their expression. *Biochim. Biophys. Acta,* 505:95–127 (1978).

Kenyon, K., Contente, S., Trackman, P. C., Tang, J., Kagan, H. M., and Friedman, R. M.; Lysyl oxidase and rrg messenger RNA. *Science,* 253:802 (1991).

Kenyon, K., Modi, W. S., Contente, S., and Friedman, R. M.; A novel human cDNA with a predicted protein similar to lysyl oxidase maps to chromosome 15q24-q25. *J. Biol. Chem.,* 268:18437 (1993).

Kiess, M., Scharm, B., Aguzzi, A., Hajnal, A., Klementz, R., Schwarte-Waldhoff, I., and Schafer, R.; Expression of ril, a novel LIM domain gene, is down-regulated in HRAS-transformed cells and restored in phenotypic revertants. *Oncogene,* 10:61–68 (1995).

Kinzler, K. W. and Vogelstein, B. The GLI gene encodes a nuclear protein which binds specific sequences in the human genome. *Mol. Cell Biol.* 10:634–642 (1990).

Klug, A. and Rhodes, D.; Zinc fingers: a novel protein fold for nucleic acid recognition. Cold Spring Harbor Symposia on Quantitative Biology, 52:473–482 (1987).

Koff, A., Ohtsuki, M., Polyak, K., Roberts, J. M., and Massague, J.; Negative regulation of G1 in mammalian cells: inhibition of cyclin E-dependent kinase by TGF-beta. *Science,* 260:536–539 (1993).

Kolesnick, R. and Golde, D. W.; The sphingomyelin pathway in tumor necrosis factor and interleukin-1 signaling. *Cell,* 77:325–328 (1994).

Kornblihtt, A. R., Vibe-Pedersen, K., and Baralle, F. E.; Isolation and characterization of cDNA clones for human and bovine fibronectins. *Proc. Natl. Acad. Sci. USA,* 80:3218–3222 (1983).

Koths, K., Taylor, E., Halenbeck, R., Casipit, C., and Wang, A.; Cloning and characterization of a human Mac-2-binding protein a new member of the superfamily defined by the macrophage scavenger receptor cysteine-rich domain. *J. Biol. Chem.*, 268:14245–14249 (1993).

Kozak, M.; An analysis of vertebrate MRNA sequences: Intimations of translational control. *J. Cell Biol.*, 115:887–903 (1991).

Krieg, P. A. and Meelton, D. A.; Functional messenger RNAs are produced by SP6 in vitro transcription of cloned cDNAs. *Nucleic Acid Res.*, 12:7057–7070 (1984).

Lecka-Czernik, B., Lumpkin, C. K., and Goldstein, S.; An overexpressed gene transcript in senescent and quiescent human fibroblasts encoding a novel protein in the EGF-like repeat family stimulates DNA synthesis. *Mol. Cell Biol.*, 15:120–128 (1995).

Lecka-Czernik, B., Moerman, E. J., Jones, R. A., and Goldstein, S.; Identification of gene sequences overexpressed in senescent and Werner syndrome fibroblasts. *Exp. Gerontol*, in press (1995).

Lee, S., Wolfraim, L. A., and Wang, E.; Differential expression of S1 and elongation factor-1 alpha during rat development. *J. Biol. Chem.*, 268:24453–24459 (1993).

Letovsky, J. and Dynan, W.; Measurement of the binding of transcription factor SP1 to a single GS box recognition sequence. *Nucleic Acids Res.*, 17:2639–2652 (1989).

Lew, D. J., Dulic, V., and Reed, S. I.; Isolation of three novel human cyclins by rescue of G1 cyclin (Cln) function in yeast. *Cell*, 66:1197–1206 (1991).

Liotta, L. A. and Steeg, P. S.; Clues to the function of Nm23 and Awd proteins in development, signal transduction, and tumor metastasis provided by studies of *Dicryostelium discoideum*. *J. Natl. Cancer Instit.*, 82:1170–1173 (1990).

Liu, S., Thweatt, R., Lumpkin, C. K., and Goldstein, S.; Suppression of calcium-dependent membrane currents in human fibroblasts by senescence and forced expression of a novel gene sequence. *Proc. Natl. Acad. Sci. USA*, 91:2186–2190 (1994).

Lumpkin, C. K., Jr., McClung, J. K., Pereira-Smith, O. M., and Smith, J. R.; Existence of high abundance antiproliferative mRNAs in senescent human diploid fibroblasts. *Science*, 232:393–395 (1986).

Maniatis, T., Sambrook, J., and Fritsch, E. F.; *Molecular Cloning: A laboratory Manual*, 2nd ed. Cold Spring Harbor Laboratory, Cold Spring Harbor, N.Y. (1989).

Mann, K., Deutzman, R., Aumailley, M., Timpl, R., Raimondi, L., Yamada, Y., Pan, T., Conway, D., and Chu, M.; Amino acid sequence of mouse nidogen, a multidomain basement membrane protein with binding activity for laminin, collagen IV and cells. *EMBO J*, 8:65–72 (1989).

Maslen, C. L., Corson, G. M., Maddox, B. K., Glanville, R. W., and Sakai, L. Y.; Partial sequence of a candidate gene for the Marfan syndrome. *Nature*, 352:334–337 (1991).

Moerman, E. J., Thweatt, R., Moerman, A. M., Jones, R. A., and Goldstein, S.; Insulin-like growth factor binding protein-3 is overexpressed in senescent and quiescent human fibroblasts. *Exp. Gerontal*, 28:361–370 (1993).

Moldave, K.; Eukaryotic protein synthesis. *Annu. Rev. Biochem.*, 54:1109–1149 (1985).

Morris, J. F., Hromas, R., and Rauscher, F. J., III; Characterization of the DNA-binding properties of the myeloid zinc finger protein MZF1: Two independent DNA-binding domains recognize two DNA consensus sequences with a common G-rich core. *Mol. Cell. Biol.*, 14:1786–1795 (1994).

Moses, H. L., Yang, E. Y., and Pietenpol, J. A.; TGFβ stimulation and inhibition in cell proliferation: new mechanistic insights. *Cell*, 63:245–247 (1990).

Murano, S., Thweatt, R., Shmookler Reis, R. J., Jones, R. A., Moerman, E. J., and Goldstein S.; Diverse gene sequences are overexpressed in Werner syndrome fibroblasts undergoing premature replicative senescence. *Mol. Cell Biol.*, 11:3905–3914 (1991).

Nada, S., Chang, P. K. K., and Digman, J. D.; Primary structure of the gene for glycyl-tRNA synthetase from Bombyx mori. *J. Biol. Chem.*, 268:7660–7667 (1993).

Nevins, J. R.; A closer look at E2F. *Nature*, 358:375–376 (1992).

Noda, A., Ning, Y., Venable, S. F., Pereira-Smith, O. M., and Smith, J. R.; Cloning of senescent cell-derived inhibitors of DNA synthesis using an expression screen. *Exp. Cell Res.*, 211:90–98 (1994).

Norwood, T. H., Pendergrass, W. R., Sprague, C. A., and Martin, G. M.; Dominance of the senscent phenotype in heterokaryons between replicative and post-replicative human fibroblastlike cells. *Proc. Natl. Acad. Sci. USA*, 71:2231–2235 (1974).

Norwood, T. H., Smith, J. R., and Stein, G. H.; Aging at the cellular level: the human fibroblastlike cell model. In: Handbook of Biology of Aging, E. L. Schneider and J. W. Rowe, eds., 3rd ed., pp. 131–154, (1990).

Obeid, L. M.; Ceramide: an endogenous inducer of cellular senescence. *Clin. Res.*, 42:114 (1994).

Obeid, L. M., Linardic, C. M., Karolak, L. A., and Hannun, Y. A.; Programmed cell death induced by ceramide. *Science*, 259:1769–1771 (1993).

Ohaski, K., Toshima, J., Tajinda, K., Nakamura, T., and Mizuno, K.; Molecular cloning of a chicken lung cDNA encoding a novel protein kinase with N-terminal two LIM/double zinc finger motifs. *J. Biochem., (Tokyo)* 116:636–642.

Okayama, H., Kawaichi, M., Brownstein, J., Lee, F., Yokota, T., and Arai, K.; High-efficiency cloning of full-length cDNA: Construction and screening of cDNA expression libraries for mammalian cells. *Methods Enzymol.*, 154:3–28 (1987).

Panayotou, G., End, E., Aumailley, M., Timple, R., and Engel, J.; Domains of laminin with growth-factor activity. *Cell*, 56:93–101 (1989).

Pathak, V. K., Nielsen, P. J., Trachsel, H., and Hershey, J. W.; Strcuture of the β subunit of translation initiation factor eIF-2. *Cell*, 54:633–639 (1988).

Penttinen, R. P., Kobayashi, S., and Bornstein, P.; Transforming growth factor β increases mRNA for matrix proteins both in the presence and in the absence of changes in MRNA stability. *Proc. Natl. Acad. Sci. USA*, 85:1105–1108 (1988).

Peters, M. and Herskowitz, I.; Joining the complex: cyclin-dependent kinase inhibitory proteins and the cell cycle. *Cell*, 79:181–184 (1994).

Pines, J. and Hunter, T.; Isolation of human cyclin cDNA: evidence for cyclin MRNA and protein regulation in the cell cycle and for interaction with p34cdc2. *Cell*, 58:833–846 (1989).

Polyak, K., Kato, J. Y., Solomon, M. J., Sherr, C. J., Messague, J., Roberts, J. M., and Koff A.; p27Kip1, a cyclin-Cdk inhibitor, links transforming growth factor-beta and contact inhibition to cell cycle arrest. *Genes & Development*, 8:9–22 (1994).

Polyak, K., Lee, M. H., Erdjument-Bromage, H., Koff, A., Roberts, J. M., Tempst, P. and Massague, J.; Cloning of p27Kip1, a cyclin-dependent kinase inhibitor and a potential mediator of extracellular antimitogenic signals. *Cell*, 78:59–66 (1994).

Ponte, P., Ng, S. Y., Engel, J., Gunning, P., and Kedes, L.; Evolutionary conservation in the untranslated regions of actin mRNAs: DNA sequence of human beta-actin cDNA. *Nucleic Acids Res.,* 12:1687–1689 (1984).

Ptashne, M.; How eukaryotic transcriptional activators work. *Nature,* 335:683–689 (1988).

Quantitative RT-PCR. *In: Methods and Application, Book 3,* ed., CLONTECH Laboratories, Inc. (1993).

Rasoamanantena, P., Thweatt, R., Labat-Robert, J., and Goldstein, S.; Overproduction of fibronectin in Werner syndrome fibroblasts. *Exp. Cell Res.* 213:121–127 (1994).

Rauscher, F. J., III, Morris, J. F., Tournay, O. E., Cook, D. M., and Curran, T.; Binding of the Wilms' tumor locus zinc finger protein to the EGR-1 consensus sequence. *Science,* 250:1259–1262.

Reed, M. J., Vernon, R. B., Abrass, I. B., and Sage, E. H.; TGF-beta 1 induces the expression of type I collagen and SPARC, and enhances contraction of collagen gels, by fibroblasts from young and aged donors. *J. Cell Physiol.,* 158:169–179 (1994).

Riabowol, K., Schiff, J., and Gilman, M.Z.; Transcription factor AP-1 activity is required for inhibition of DNA synthesis and is lost during cellular aging. *Proc. Natl. Sci. Acad. USA,* 89:157–161 (1992).

Richter, K. H., Afshari, C. A., Annab, L. A., Burkhart, B. A., Owen, R. D., Boyd, J., and Barrett, J. C.; Down-regulation of cdc2 in senescent human and hamster cells. *Cancer Res.,* 51:6010–6013 (1991).

Ridley, A. J., Paterson, H. F., Johnston, C. L., Dickmann, D., and Hall, A.; The small GTP-binding protein rac regulates growth factor induced membrane ruffling. *Cell,* 70:401–411 (1992).

Riggs, A. D., Suzuki, H., and Bourgeois, S.; Lac repressor-operator interaction I. Equilibrium studies. *J. Mol. Biol.,* 48:67–83 (1970).

Roberts, C. J., Birkenmeier, T. M., McQuillan, J. J., Akiyama, S. K., Yamada, S. S., Chen, W. T., Yamada, K. M., and McDonald, J. A.; Transforming growth factor 6 stimulates the expression of fibronectin and of both subunits of the human fibronectin receptor by cultured human lung fibroblasts. *J. Biol. Chem.,* 263:4586–4592 (1988).

Rooney, B. C., Horne, C. H., and Hardman, N.; Molecular cloning of a cDNA for human pregnancy-specific β-1-glycoprotein: homology with human carcinoembryonic antigen and related proteins. *Gene,* 71:439–449 (1988).

Ruoslahti, E. and Yamaguchi, Y.; Protcoglycans as modulators of growth factor activities. *Cell,* 64:867–869 (1991).

Sadler, I., Crawford, A. W., Michelsen, J. W., and Beckerle, M. C.; Zyxin and cCRP: Two interactive LIM domain proteins associated with the cytoskeleton. *J. Cell Biol.,* 119:1573–1587 (1992).

Sakamoto, K., Fordis, C. M., Corsico, C. D., Howard, T. H., and Howard, B. H.; Modulation of HeLa cell growth by transfected 7SL RNA and Alu gene sequences. *J. Biol. Chem.,* 266:3031–3038 (1991).

Salk, D.; Werner's syndrome: a review of recent research with an analysis of connective tissue metabolism, growth control of cultured cells and chromosomal aberrations. *Hum. Genet.,* 62:1–5 (1982).

Sanchez-Garcia, I. and Rabbits, T. H.; The LIM domain: a new structural motif found in zinc-finger-like proteins. *Trends Genet.,* 10:315–320 (1994).

Sanger, F., Nickel, S., and Coulson, A. R.; DNA sequencing with chain terminating inhibitors. *Proc. Natl. Acad. Sci. USA,* 74:5463–5467 (1977).

Schellenberg, G. D., Martin, G. M., Wijsman, E. M., Nakura, J., Miki, T., and Ogihara, T.; Homozygosity mapping and Werner's syndrome. *Lancet,* 339:1002 (1992).

Schmeichel, K. L. and Beckerle, M. C.; The LIM domain is a modular protein-binding interface. *Cell,* 79:211–219 (1994).

Schweinfest, C. W., Henderson, K. W., Gu, J., Kottardis, S. D., Besbeas, S., Panotopoulou, E., and Papas, T. S.; Subtraction hybridization cDNA libraries from colon carcinoma and hepatitic cancer. *Genet Annal. Techn. Appl.,* 7:64–70 (1990).

Schuchman, E. H., Suchi, M., Takahashi, T., Sandhoff, K., and Desnick, R. J.; Human acid sphingomyelinase. Isolation, nucleotide sequence and expression of the full-length and alternatively spliced cDNAs. *J. Biol. Chem.,* 266:8531–8539 (1991).

Serrano, M., Hannon, G. J., and Beach, D.; A new regulatory motif in cell-cycle control causing specific inhibition of cyclin D/CDK4. *Nature* 366:704–707 (1993).

Seshadri, T. and Campisi, J.; Repression of c-fos transcription and an altered genetic program in senescent human fibroblasts. *Science,* 247:205–209 (1990).

Shibanuma, M., Mashimo, J., Koroki, T., and Nose, K.; Characterization of the TGFβ1-inducible hic-5 gene that encodes a putative novel zinc finger protein and its possible involvement in cellular senescence. *J. Biol. Chem.,* 269:26767–26774 (1994).

Shina, N., Gotoh, Y., Kubomura, N., Iwamatsu, A., and Nishida, B.; Microtubule severing by elongation factor la. *Science,* 266:282–285 (1994).

Show, G. and Kamen, R.; A conserved AU sequence from the 3' untranslated region of GM-CSF MRNA mediates selective mRNA degradation. *Cell,* 46:659–667 (1986).

Shutze, S., Potthoff, K., Machleidt, T., Berkovic, D., Wiegmann, K., and Kronke, M.; TNF activates Nf-kB by phophatidylcholine-specific phospholipase C-induced "acidic" sphingomyelin breakdown. *Cell,* 71:765–776 (1992).

Sive, H. L. and St. John, T.; A simple subtractive hybridization technique employing photactivatable biotin and phenol extaction. *Nucleic Acid Res.,* 16:10937 (1988).

Stahl, J. A., Leone, A. Rosengard, A. M., Porter, L., King, C. R. and Steeg, P. S.; Identification of a second human nm23-H2, *Cancer Res.,* 52:445–449 (1991).

Steeg, P.S., Bevilacqua, G., Kopper, L., Thorgeirsson, U. P., Talmadge, J. E., Liotta, L. A., and Sobel, M. E.; Evidence for a novel gene associated with low tumor metastatic potential. *J. Natl. Cancer Inst.,* 80:200–204 (1988).

Stein, G. H., Beeson, M., and Gordon, L.; Failure to phosphorylate the retinoblastoma gene product in senescent human fibroblasts. Science, 249:666–669 (1990).

Stein, G. H., Drullinger, L. F., Robetorye, R. S., Pereira-Smith, O. M., and Smith, J.; Senescent cells fail to express cdc2, cycA and cycB in response to mitogen stimulation. *Proc. Natl. Acad. Sci. USA* 88:11012–11016 (1991).

Stein, G. H. and Yanishevsky, R. M.; Quiescent human diploid cells can inhibit entry into S phase in replicative nuclei in heterodikaryons. *Proc. Natl. Acad. Sci. USA,* 78:3025–3029 (1981).

Sukhatme, VP., Cao, X., Chang, L. C., Tsai-Morris, C., Stamenkowich, D., Ferreira, P. C. P., Cohen, D. R., Edwards, S. A., Shows, T. B., Curran, T., Le Bau, M. M., and Adamson, E.D.; A zinc finger-encoding gene coregulated with c-fos during growth and differentiation, and after cellular differentiation. *Cell,* 56:337–343 (1988).

Swaroop, A., Hogan, B. L. M., and Francke, U.; Molecular analysis of the cDNA for human SPARC/osteonectin/BM-40: sequence, expression and localization of the gene to chromosome 5q31-q33. *Genomics,* 2:37–47 (1988).

Symington, B. E.; Fibronectin receptor modulates cyclin-dependent kinase activity. *J. Biol. Chem.,* 267:25744–25747 (1992).

Tanaka, K., Nakazawa, T., Okada, Y., and Kumahara, Y.; Roles of nuclear and cytoplasmic environments in the retarded DNA synthesis of Werner syndrome cells *Exp. Cell Res.*, 127:185–190 (1980).

Tatsuka, M., Mitsui, H., Wada, M., Nagata, A., Nojima, H., and Okayama, H.; Elongation factor-1α gene determines susceptibility to transformation. *Nature*, 359:333–336 (1992).

Tautz, D., Lehmann, R., Schnurch, H., Schuh, R., Seifert, E., Kienlin, A., Jones, K., and Jackle, H.; Finger protein of novel structure encoded by hunchback, a second member of the gap class of Drosophila segmentation genes. *Nature*, 327:383–389 (1987).

Taylor, J. M., Davies, J. D., and Peterson, C. A.; Regulation of the myoblast-specific expression of the human 6-enolase gene. *J. Biol. Chem.*, 270:2535–2540 (1995).

Termin, J. D.; Cellular activity, matrix proteins, and aging bone. *Exp. Gerontol*, 25:217–221 (1990).

Thweatt, R., Lumpkin, C. K., and Goldstein, S.; A novel gene encoding a smooth muscle protein is overexpressed in senescent human fibroblasts. *Biochem. Biophys. Res. Commun.*, 187:1–7 (1992).

Thweatt R. and Goldstein S.; Werner syndrome and biological aging: a molecular genetic hypothesis. BioEssays, 15:421426 (1993).

Toyoshima, H. and Humter, T.; p27, a novel inhibitor of G1 cyclin-Cdk protein kinase activity, is related to p21. *Cell*, 78:67–74 (1994).

Uetsuki, T., Naito, A., Nagata, S., and Kaziro, Y.; Isolation and characterization of the human chromosomal gene for polypeptide chain elongation factor 1-α. *J. Biol. Chem.*, 264:5791–5798 (1989).

Walldorf, U., Fleig, R., and Gehring, W. J.; Comparision of homeobox-containing genes of the honeybee and Drosophila. *Proc. Nat'l. Acad. Sci., U.S.A.*, 86:9971–9975 (1990).

Wang, A. M., Doyle, M. V., and Mark, D. F.; Quantitation of mRNA by the polymerase chain reaction. *Proc. Nat'l. Acad. Sci., U.S.A.*, 86:9717–9721 (1989).

Wang, L., Patel, U., Ghosh., L., Chen, H. C., and Banerjee, S.; Mutation in the nm23 gene is associated with metastasis in colorectal cancer. *Cancer Res.*, 53:717–720 (1993).

Wang, X., Lee., G., Liebhaber, S. A., and Cooke, N. E.; Human cysteine-rich protein: A member of the LIM/double-finger family displaying coordinate serum induction with c-myc. *J. Biol. Chem.*, 267:9176–9184 (1992).

Way, G. C. and Chalfie, M.; mec-3, a homeobox-containing gene that specifies differentiation of the touch receptor eurons in C. elegans. *Cell*, 54:5–16 (1988).

Wharton, K. A., Johansen, K. M., Xu T., and Artavanis-Tsakonas, S.; Nucleotide sequence from the neurogenic locus Notch implies a gene product that shares homology with proteins containing EGF-like repeats. *Cell*, 43:567–581 (1985).

Witzgall, R., O'Leary, E., Gessner, R., Ouellette, A. J., and Bonventre, J. V.; Kid-1, a putative renal transcription factor. Regulation during ontogeny and in response to ischemia and toxic injury. *Mol. Cell. Biol.*, 13:1933–1942 (1993).

Xiong, Y., Hannon, G. J., Zhang, H., Casso, D., Kobayashi, R. and Beach, D.; p21 is a universal inhibitor of cyclin kinases. *Nature*, 366:701–704 (1993).

Yanishevsky, R. M. and Stein, G.; Ongoing DNA synthesis continues in young human diploid cells (HDC) fused to senescent HDC, but entry into S phase is inhibited. *Exp. Cell Res.*, 126:469–472 (1980).

Other embodiments are within the following claims.

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1161 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 2..674

(xi) SEQUENCE DESCRIPTION: SEQ ID NO:1:

```
C CCC ATT GAA GTT TGC CGG TCC AAA CTG TCC AAA TAC TTG CAG GGA         46
  Pro Ile Glu Val Cys Arg Ser Lys Leu Ser Lys Tyr Leu Gln Gly
    1               5                  10                  15

GTA GTT TTC CGC TGT GAT AAG TGT ACC TTC ACC TGC TCC AGT GAT GAG       94
Val Val Phe Arg Cys Asp Lys Cys Thr Phe Thr Cys Ser Ser Asp Glu
                 20                  25                  30

AGC CTC CAG CAA CAT ATA GAA AAG CAC AAT GAA CTG AAA CCT TAC AAA      142
Ser Leu Gln Gln His Ile Glu Lys His Asn Glu Leu Lys Pro Tyr Lys
             35                  40                  45

TGC CAG CTC TGC TAC TAT GAG ACC AAG CAC ACG GAG GAA CTG GAC AGC      190
```

```
                                                                              -continued Cys Gln Leu Cys Tyr Tyr Glu Thr Lys His Thr Glu Leu Asp Ser
         50                  55                  60

CAC CTT CGG AAT GAG CAT AAG GTA AGC CGT AAC TTT GAG CTG GTT GGA              238
His Leu Arg Asn Glu His Lys Val Ser Arg Asn Phe Glu Leu Val Gly
         65                  70                  75

CGA GTT AAC TTG GAT CAG CTG GAA CAG ATG AAG GAG AAA ATG GAG AGC              286
Arg Val Asn Leu Asp Gln Leu Glu Gln Met Lys Glu Lys Met Glu Ser
 80                  85                  90                  95

TCC AGC AGC GAT GAT GAG GAC AAG GAA GAA GAA ATG AAC AGC AAG GCT              334
Ser Ser Ser Asp Asp Glu Asp Lys Glu Glu Glu Met Asn Ser Lys Ala
                100                 105                 110

GAA GAC AGA GAG CTG ATG AGA TTT TCT GAC CAC GGG GCT GCT CTT AAC              382
Glu Asp Arg Glu Leu Met Arg Phe Ser Asp His Gly Ala Ala Leu Asn
            115                 120                 125

ACT GAG AAG CGT TTT CCA TGT GAA TTT TGT GGA CGG GCG TTT TCA CAG              430
Thr Glu Lys Arg Phe Pro Cys Glu Phe Cys Gly Arg Ala Phe Ser Gln
            130                 135                 140

GCC TCT GAG TGG GAA AGA CAT GTG CTG AGA CAC GGC ATG GCA TTG AAT              478
Ala Ser Glu Trp Glu Arg His Val Leu Arg His Gly Met Ala Leu Asn
145                 150                 155

GAC ACC AAG CAG GTG AGC AGA GAA GAA ATC CAC CCA AAA GAG ATC ATG              526
Asp Thr Lys Gln Val Ser Arg Glu Glu Ile His Pro Lys Glu Ile Met
160                 165                 170                 175

GAG AAC AGT GTT AAA ATG CCC TCC ATA GAG GAA AAG GAA GAT GAC GAG              574
Glu Asn Ser Val Lys Met Pro Ser Ile Glu Glu Lys Glu Asp Asp Glu
                180                 185                 190

GCC ATT GGG ATA GAC TTT TCC CTA AAG AAT GAA ACA GTA GCC ATC TGT              622
Ala Ile Gly Ile Asp Phe Ser Leu Lys Asn Glu Thr Val Ala Ile Cys
            195                 200                 205

GTA GTA ACT GCC GAC AAA TCT CTC CTG GAG AAT GCA GAG GCC AAA AAA              670
Val Val Thr Ala Asp Lys Ser Leu Leu Glu Asn Ala Glu Ala Lys Lys
            210                 215                 220

GAA T GAGCGTTTGG TGAAATTCTT AATCAAACCT TACTTGAACA GTGATGAAAA                 724
Glu

AGTGGGAGGG CTGGCTTGGG CTGAGAAGGG AGGGACAGAA AAGAGAAGAC AGAACAAAGC            784

TGCTTTTTAG GACTGAACAA TCTATTTTCA AAGCACTGGT ACCTGTGTGA GTGAGTATGT            844

AAATTAAAGT TATTTAAATG GTTGGAATAT GTGGCTCCTT TTCCATCACT ACATCTTTTC            904

TTCCGGATCT TCATCATGGA AGTTTCATTT GTTGCGGAAT ATGGAAGCAC CTCCCAATGG            964

TACGGTGCAC CCTGTGGTGG TCTTGGACAG TATGTGAAAA CAGAAGCTCC ATGACGGTAG           1024

AAGACTTCTC ATTGGGGGAG CAACTTTTTG ACGCACAACT TTTGGTGCGT TTTTTCTAGT           1084

TTTAATACCT TAAGCTTTTT CAAGACCTAA CTGCAGCCGC TTTGGGAAAA AAAAACAAAA           1144

AACAAAAAAC AGAAAAC                                                         1161

(2) INFORMATION FOR SEQ ID NO:2:

(i) SEQUENCE CHARACTERISTICS:
        (A) LENGTH: 224 amino acids
        (B) TYPE: amino acid
        (D) TOPOLOGY: linear (ii) MOLECULE TYPE: protein (xi) SEQUENCE DESCRIPTION: SEQ ID NO:2:

Pro Ile Glu Val Cys Arg Ser Lys Leu Ser Lys Tyr Leu Gln Gly Val
 1               5                  10                  15

Val Phe Arg Cys Asp Lys Cys Thr Phe Thr Cys Ser Ser Asp Glu Ser
            20                  25                  30
```

-continued

```
Leu Gln Gln His Ile Glu Lys His Asn Glu Leu Lys Pro Tyr Lys Cys
        35                  40                  45

Gln Leu Cys Tyr Tyr Glu Thr Lys His Thr Glu Glu Leu Asp Ser His
    50                  55                  60

Leu Arg Asn Glu His Lys Val Ser Arg Asn Phe Glu Leu Val Gly Arg
65                  70                  75                  80

Val Asn Leu Asp Gln Leu Glu Gln Met Lys Glu Lys Met Glu Ser Ser
                85                  90                  95

Ser Ser Asp Asp Glu Asp Lys Glu Glu Glu Met Asn Ser Lys Ala Glu
            100                 105                 110

Asp Arg Glu Leu Met Arg Phe Ser Asp His Gly Ala Ala Leu Asn Thr
            115                 120                 125

Glu Lys Arg Phe Pro Cys Glu Phe Cys Gly Arg Ala Phe Ser Gln Ala
        130                 135                 140

Ser Glu Trp Glu Arg His Val Leu Arg His Gly Met Ala Leu Asn Asp
145                 150                 155                 160

Thr Lys Gln Val Ser Arg Glu Glu Ile His Pro Lys Glu Ile Met Glu
                165                 170                 175

Asn Ser Val Lys Met Pro Ser Ile Glu Lys Glu Asp Asp Glu Ala
            180                 185                 190

Ile Gly Ile Asp Phe Ser Leu Lys Asn Glu Thr Val Ala Ile Cys Val
        195                 200                 205

Val Thr Ala Asp Lys Ser Leu Leu Glu Asn Ala Glu Ala Lys Lys Glu
    210                 215                 220
```

(2) INFORMATION FOR SEQ ID NO:3:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

```
Val Phe Arg Cys Asp Lys Cys Thr Phe Thr Cys Ser Ser Asp Glu Ser
1               5                   10                  15

Leu Gln Gln His Ile Glu Lys His Asn Glu Leu Lys
            20                  25
```

(2) INFORMATION FOR SEQ ID NO:4:

(i) SEQUENCE CHARACTERISTICS:
        (A) LENGTH: 29 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

```
Pro Tyr Lys Cys Gln Leu Cys Tyr Tyr Glu Thr Lys His Thr Glu Glu
1               5                   10                  15

Leu Asp Ser His Leu Arg Asn Glu His Lys Val Ser Arg
            20                  25
```

(2) INFORMATION FOR SEQ ID NO:5:

(i) SEQUENCE CHARACTERISTICS:
        (A) LENGTH: 28 amino acids
        (B) TYPE: amino acid

```
        (C) STRANDEDNESS: Not Relevant
        (D) TOPOLOGY: linear (ii) MOLECULE TYPE: protein (xi) SEQUENCE DESCRIPTION: SEQ ID NO:5:

Arg Phe Pro Cys Glu Phe Cys Gly Arg Ala Phe Ser Gln Gly Ser Glu
1               5                   10                  15

Trp Glu Arg His Val Leu Arg His Gly Met Ala Leu
            20                  25

(2) INFORMATION FOR SEQ ID NO:6:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GATAGATG                                                                 8

(2) INFORMATION FOR SEQ ID NO:7:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GATGATAG                                                                 8
```

What is claimed is:

1. An isolated DNA encoding a human DNA binding protein or polypeptide comprising the amino acid sequence of SEQ ID NO:2.

2. The DNA of claim 1 comprising the nucleic acid sequence of SEQ ID NO:1.

3. A vector comprising the DNA of claim 2.

4. The DNA of claim 2, wherein said DNA is operably linked to regulatory sequences for expression of said protein, said regulatory sequences comprising a promoter.

5. A cell comprising the DNA of claim 4.

6. A population of cells wherein each cell comprises the DNA of claim 4.

7. An isolated DNA consisting of at least 20 contiguous nucleotides of SEQ ID NO:1 from nucleotides 2 to 673.

8. The isolated DNA of claim 7 consisting of at least 20 contiguous nucleotides encoding a portion of SEQ ID NO:3, zinc finger domain #1.

9. The isolated DNA of claim 7 consisting of at least 20 contiguous nucleotides encoding a portion of SEQ ID NO:4, zinc finger domain #2.

10. The isolated DNA of claim 7 consisting of at least 20 contiguous nucleotides encoding a portion of SEQ ID NO:5, zinc finger domain #3.

* * * * *